United States Patent [19]
Hubele et al.

[11] Patent Number: 5,266,585
[45] Date of Patent: Nov. 30, 1993

[54] ARYLPHENYL ETHER DERIVATIVES, COMPOSITIONS CONTAINING THESE COMPOUNDS AND USE THEREOF

[75] Inventors: Adolf Hubele, Magden; Peter Riebli, Buckten, both of Switzerland

[73] Assignee: Ciba-Geigy Corporation, Ardsley, N.Y.

[21] Appl. No.: 540,261

[22] Filed: Oct. 11, 1983

Related U.S. Application Data

[63] Continuation-in-part of Ser. No. 442,062, Nov. 16, 1982, abandoned, which is a continuation-in-part of Ser. No. 375,613, May 6, 1982, abandoned.

[30] Foreign Application Priority Data

May 12, 1981 [CH] Switzerland .................. 3066/81
Apr. 21, 1982 [CH] Switzerland .................. 2428/82

[51] Int. Cl.$^5$ .............. A01N 43/653; A01N 43/54; A61K 31/41; A61K 31/415
[52] U.S. Cl. .................... 514/383; 514/397; 514/400; 548/268.6; 548/268.8; 548/311.1; 548/311.7; 548/341.1
[58] Field of Search ............ 548/101, 262, 336, 341, 548/268.6, 268.8, 311.1, 311.7, 341.1; 424/245, 269, 273 R; 514/383, 397, 400

[56] References Cited

U.S. PATENT DOCUMENTS

| | | | |
|---|---|---|---|
| 4,101,665 | 7/1978 | Heeres | 548/341 |
| 4,101,666 | 7/1978 | Heeres | 548/336 |
| 4,156,008 | 5/1979 | Heeres | 548/336 |
| 4,160,838 | 7/1979 | Van Reet et al. | 548/262 |
| 4,329,342 | 5/1982 | Heeres et al. | 548/262 |
| 4,349,556 | 9/1982 | Timmler et al. | 424/273 R |
| 4,366,152 | 12/1982 | Kramer et al. | 548/101 |
| 4,479,004 | 10/1984 | Hubele et al. | 548/262 |

FOREIGN PATENT DOCUMENTS

| | | | |
|---|---|---|---|
| 0026990 | 4/1981 | European Pat. Off. | 548/262 |
| 0029355 | 5/1981 | European Pat. Off. | 548/262 |
| 0043419 | 1/1982 | European Pat. Off. | 548/262 |
| 1533705 | 11/1978 | United Kingdom | 548/262 |
| 1533706 | 11/1978 | United Kingdom | |
| 2027701 | 2/1980 | United Kingdom | 548/262 |

Primary Examiner—Richard L. Raymond
Attorney, Agent, or Firm—Edward McC. Roberts

[57] ABSTRACT

Arylphenyl ether derivatives of the formula

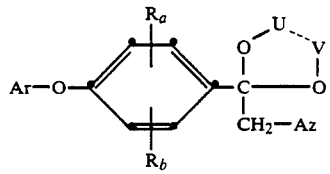

wherein

Az is 1H-(1,2,4-triazolyl) or is 1-imidazolyl optionally substituted by alkyl, each of $R_a$ and $R_b$ is hydrogen, halogen, alkyl, alkoxy or nitro, Ar is phenyl or naphthyl, optionally substituted by halogen, alkyl, alkoxy, nitro or $CF_3$, each of U and V, is alkyl optionally substituted by halogen or alkoxy, or together form an alkylene bridge

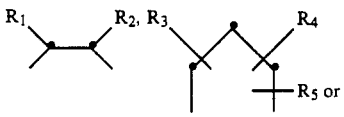

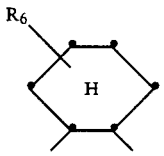

wherein each of $R_1$ and $R_2$ is hydrogen, or alkyl optionally substituted by halogen; phenyl optionally substituted by halogen or alkyl; or —$CH_2$—Z—$R_7$ in which Z is oxygen or sulfur, and $R_7$ is hydrogen, alkyl optionally substituted by alkoxy, alkenyl, prop-2-ynyl, 3-haloprop-2-ynyl, phenyl optionally substituted by halo- (Abstract continued on next page.)

gen, alkyl, alkoxy, nitro or by $CF_3$, benzyl optionally substituted by halogen, alkyl or by alkoxy, each of $R_3$, $R_4$ and $R_5$ is hydrogen or alkyl, the total number of carbon atoms in $R_3$, $R_4$ and $R_5$ not exceeding 6, and $R_6$ is hydrogen or alkyl, together with the acid addition salts and metal complexes thereof. They may be used in agriculture for controlling phytopathogenic microorganisms and as antimycotic and/or anticonvulsive and anxiolytic agents in the pharmaceutical field.

57 Claims, No Drawings

ARYLPHENYL ETHER DERIVATIVES, COMPOSITIONS CONTAINING THESE COMPOUNDS AND USE THEREOF

CROSS REFERENCE TO RELATED APPLICATONS

This is a continuation-in-part of co-pending application Ser. No. 442,062 filed on Nov. 16, 1982, now abandoned, which itself is a continuation-in-part of co-pending application Ser. No. 375,613 filed on May 6, 1982, now abandoned.

The present invention relates to substituted arylphenyl ether derivatives of the formula I below, and to the acid addition salts and metal complexes thereof. The invention also relates to the production of these compounds as well as to agrochemical compositions and pharmaceutical preparations which contain at least one compound of the formula I as active ingredient, to the production of these compositions and preparations and to the use thereof, and further to a method of treating plants for controlling or preventing attack by phytopathogenic microorganisms.

The arylphenyl ether derivatives of this invention have the formula

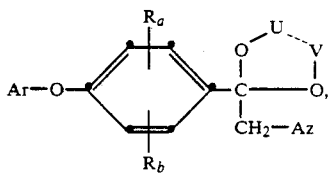

wherein

Az is 1H-1,2,4-triazolyl or the group

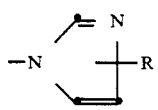

in which

R is hydrogen or $C_1$-$C_6$alkyl, $R_a$ and $R_b$, each independently of the other, are hydrogen, halogen, $C_1$-$C_3$alkyl, $C_1$-$C_3$alkoxy or nitro, Ar is phenyl or naphthyl, each unsubstituted or mono-or polysubstituted by halogen, $C_1$-$C_7$alkyl, $C_1$-$C_7$alkoxy, nitro and/or $CF_3$, U and V each independently of the other, are $C_1$-$C_{12}$alkyl which is unsubstituted or substituted by halogen or $C_1$-$C_6$alkoxy, or together form one of the following alkylene bridges

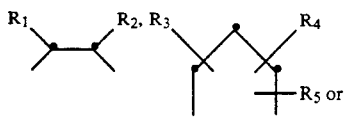

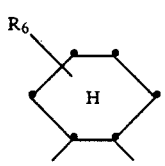

in which $R_1$ and $R_2$, each independently of the other, are hydrogen, $C_1$-$C_{12}$alkyl or $C_1$-$C_{12}$alkyl which is mono- or poly-substituted by halogen; phenyl or phenyl which is mono- or polysubstituted by halogen and/or $C_1$-$C_3$alkyl; or is the —$CH_2$—Z—$R_7$ group, wherein Z is oxygen or sulfur and $R_7$ is hydrogen, $C_1$-$C_8$alkyl or $C_1$-$C_8$alkyl which is substituted by $C_1$-$C_2$alkoxy; $C_3$-$C_4$alkenyl, prop-2-ynyl, 3-haloprop-2-ynyl, phenyl or phenyl which is mono-or polysubstituted by halogen $C_1$-$C_3$alkyl, $C_1$-$C_3$ alkoxy, nitro and/or $CF_3$; benzyl or benzyl which is mono-or polysubstituted by halogen, $C_1$-$C_3$alkyl and/or $C_1$-$C_3$alkoxy, $R_3$, $R_4$ and $R_5$ each independently of the other, are hydrogen or $C_1$-$C_4$alkyl, the total number of carbon atoms in $R_3$, $R_4$ and $R_5$ not exceeding 6, and $R_6$ is hydrogen or $C_1$-$C_3$alkyl, together with the acid addition salts and metal complexes thereof.

This invention relates within narrower limits to compounds of the above defined formula I which are characterized by a triazole or an unsubstituted imidazole ring.

As unsubstituted or substituted phenyl or naphthyl, the substituent Ar has e.g. the formula

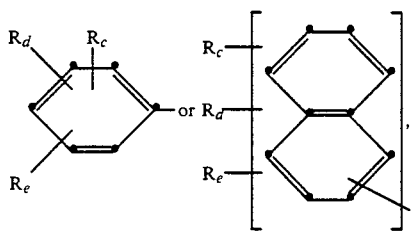

wherein $R_c$, $R_d$ and $R_e$, each independently of the other, are hydrogen, halogen, $C_1$-$C_7$alkyl, $C_1$-$C_7$alkoxy, nitro or $CF_3$.

Depending on the number of indicated carbon atoms, the term "alkyl" by itself or as moiety of another substituent will be understood as meaning e.g. the following groups: methyl, ethyl, propyl, butyl, pentyl, hexyl, heptyl, octyl, nonyl, decyl, undecyl or dodecyl, and the isomers thereof, e.g. isopropyl, isobutyl, tertbutyl, sec-butyl, isopentyl etc. Alkenyl denotes e.g. propen-1-yl, allyl, buten-1-yl, buten-2-yl or buten-3-yl. Throughout this specification, halogen denotes fluorine, chlorine, bromine or iodine, with chlorine or bromine being preferred.

The invention relates both to the free compounds of the formula I and to the acid addition salts thereof with inorganic and organic acids, and likewise to their complexes with metal salts.

Salts of this invention are in particular addition salts with inorganic or organic acids which are physiologically tolerable with respect to the envisaged utility.

Examples of inorganic and organic acids which are physiologically tolerable with respect to the utility as microbicides in plant protection, are hydrohalic acids, e.g. hydrochloric, hydrobromic or hydriodic acid, sulfuric acid, phosphoric acid, phosphorous acid, nitric acid, unsubstituted or halogenated fatty acids such as acetic acid, trichloroacetic acid and oxalic acid, or sulfonic acids such as benzenesulfonic acid and methanesulfonic acid.

Acids which are physiologically tolerable in respect of the utility as medicament, i.e. pharmaceutically acceptable acids, are e.g. pharmaceutically acceptable mineral acids such as hydrohalic acids, e.g. hydrochloric, hydrobromic or hydriodic acid, nitric acid, sulfuric acid or phosphoric acid, pharmaceutically acceptable carboxylic and sulfonic acids such as aliphatic monocarboxylic acids and optionally hydroxylated dicarboxylated acids, e.g. acetic acid, fumaric acid, maleic acid, malic acid or tartaric acid, and also aliphatic or aromatic sulfonic acids such as lower alkanesulfonic acid or unsubstituted or substituted benzenesulfonic acid, e.g. methanesulfonic acid, ethanesulfonic acid, benzenesulfonic acid, p-toluenesulfonic acid and p-bromobenzenesulfonic acid, as well as sulfamic acids, e.g. N-cyclohexylsulfamic acid.

Metal complexes of formula I consist of the basic organic molecule and an inorganic or organic metal salt, e.g. the halides, nitrates, sulfates, phosphates, tartrates etc. of copper, manganese, iron, zinc and other metals. The metal cations may exist in different valence states.

The compounds of formula I are oils, resins or solids which are stable at room temperature and which possess very valuable physiological properties, such as microbicidal, e.g. phytofungicidal and pharmacological properties, in particular antimycotic as well as anticonvulsive, antidepressive and anxiolytic properties. They may therefore may be used, on the one hand, in agriculture or related fields for controlling phytopathogenic microorganisms and, on the other, as antimycotic and/or anticonvulsive, antidepressive and anxiolytic agents in the pharmaceutical field, for example for controlling parasitic fungi in warm-blooded animals and/or for treating different forms of epilepsy, states of anxiety, tension and excitation, manic and/or depressive states of mind.

An important group of microbicides for use in plant protection comprises compounds of the formula I, wherein Az is 1H-1,2,4-triazolyl or optionally substituted imidazolyl, each of $R_a$ and $R_b$ independently of the other is hydrogen, halogen, $C_1-C_3$alkyl, $C_1-C_3$alkoxy or nitro; Ar is the group

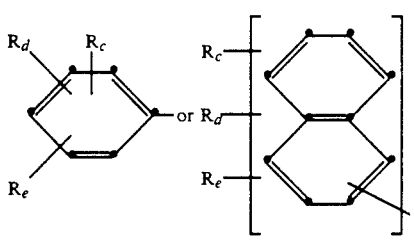

wherein
$R_c$, $R_d$ and $R_e$, each independently of the other, are hydrogen, halogen, $C_1-C_3$alkyl, $C_1-C_3$alkoxy, nitro or $CF_3$,
U and V, each independently of the other, are $C_1-C_{12}$alkyl or together form one of the following alkylene bridges

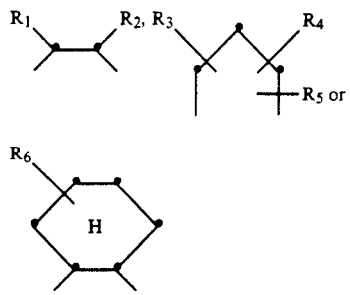

wherein
$R_1$ and $R_2$, each independently of the other, are hydrogen, $C_1-C_3$alkyl or $C_1-C_{12}$alkyl which is mono or poly-substituted by halogen, or are phenyl or phenyl which is mono- or polysubstituted by halogen and/or $C_1-C_3$alkyl, or are the —$CH_2$—Z—$R_7$ group, in which
Z is oxygen or sulfur and
$R_7$ is hydrogen, $C_1-C_8$alkyl or $C_1-C_8$alkyl which is substituted by $C_1-C_2$alkoxy, or is $C_3-C_4$ alkenyl, prop-2-ynyl, 3-haloprop-2-ynyl, phenyl or phenyl which is mono- or polysubstituted by halogen, $C_1-C_3$alkyl, $C_1-C_3$alkoxy, nitro and/or $CF_3$, or is benzyl or benzyl which is mono- or polysubstituted by halogen, $C_1-C_3$alkyl and/or $C_1-C_3$akoxy,
$R_3$, $R_4$ and $R_5$, each independently of the other, are hydrogen or $C_1-C_4$alkyl, the total number of carbon atoms in $R_3$, $R_4$ and $R_5$ not exceeding 6, and
$R_6$ is hydrogen or $C_1-C_3$alkyl,
and the acid addition salts and metal complexes thereof. This subgroup will be designated group Ia.

A preferred group of agriculturally useful microbicides comprises compounds of the formula I, including their salts and metal complexes, wherein each of $R_a$ and $R_b$ independently of the other is hydrogen, halogen or $C_1-C_3$alkyl, Ar is the group

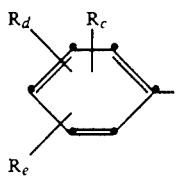

wherein each of $R_c$, $R_d$ and $R_e$ independently of the other is hydrogen, $CF_3$ or $C_1-C_3$alkyl, and Az, U and V are as defined for formula I. This group will be designated group Ib.

Preferred microbicides within subgroup Ib are those compounds of the formula I, wherein each of U and V independently of the other is $C_1-C_3$alkyl or together form one of the following alkylene groups

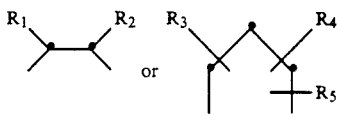

wherein each of $R_1$, $R_2$, $R_3$, $R_4$ and $R_5$ independently of the other is hydrogen or $C_1-C_4$alkyl, the total number of carbon atoms in $R_3$, $R_4$ and $R_5$ not exceeding 6. This group will be designated group Ic.

A further preferred group of agriculturally useful microbicides comprises compounds of the formula I, wherein Az and Ar are as defined for formula I, each of $R_a$, $R_b$, $R_c$, $R_d$ and $R_e$ independently of the other is chlorine, bromine, fluorine, methyl, methoxy or nitro; each of U and V independently of the other is $C_1$–$C_3$ alkyl or together form one of the alkylene groups as defined for formula I, wherein each of $R_1$, $R_2$, $R_3$, $R_4$, $R_5$ and $R_6$ independently of the other is hydrogen or $C_1$–$C_3$alkyl, or $R_1$ is —$CH_2$—O—$R_7$, in which $R_7$ is $C_1$–$C_3$alkyl, $C_2$–$C_4$alkyl which is substituted by $C_1$–$C_3$alkoxy, or is $C_3$–$C_4$alkenyl or phenyl. This group will be designated group Id.

Particularly preferred microbicides within group Id are those in which U and V together form an unsubstituted or a simply substituted ethylene or propylene bridge. This roup will be designated group Ie.

Accordingly, the following individual compounds may be cited as exemplifying particularly preferred compounds for use in agriculture:

2-[p-(phenoxy)phenyl]-2-[1-(1H-1,2,4-triazolyl)methyl]-4-methyl-1,3-dioxane,

2-[p-(phenoxy)phenyl]-2-[1-(1H-1,2,4-triazolyl)methyl]-4-ethyl-1,3-dioxane,

2-[p-(phenoxy)phenyl]-2-[1-(1H-1,2,4-triazolyl)methyl]-4-methyl-1,3-dioxolane,

2-[p-(phenoxy)phenyll-2-[1-(1H-1,2,4-triazolyl)methyl]-4-ethyl-1,3-dioxolane.

2-[p-(4'-bromophenoxy)phenyl]-2-[1-(1H-1,2,4-triazolyl)-methyl]- 4-ethyl-1,3-dioxolane;

2-[p-(phenoxy)-2'-methylphenyl]-2-[1-(1H-1,2,4-triazolyl)-methyl]-4-ethyl-1,3-dioxolane;

2-[p-(3',4'-dichlorophenoxy)phenyl]-2-[1-(1H-1,2,4-triazolyl)methyll-4-methoxymethyl-1,3-dioxolane;

2-[p-(3',4'-dichlorophenoxy)phenyl]-2-[1-(1H-1,2,4triazolyl)methyl]- 4-ethyl-1,3-dioxolane;

2-[p-(4'-chlorophenoxy)phenyl]-2-[1-(1H-1,2,4-triazolyl)methyl]-4-ethyl-1,3-dioxolane copper sulphate complex;

2-[p-(4'-chlorophenoxy)-2'-methylphenyl]-2-[1-(1H-1,2,4-triazolyl)methyl]-4-methyl-1,3-dioxolane;

2-[p-(phenoxy)-2'-methylphenyl]-2-[1-(1H-1,2,4-triazolyl)methyl]-4-ethyl-1,3-dioxolane nitric acid salt;

2-[p-(4'-chlorophenoxy)phenyl]-2-[1-(1H-1,2,4-triazolyl)-methyl]-4-ethyl-1,3-dioxolane;

2-[p-(4'-chlorophenoxy)-2'-chloropehnyl]-2-(1H-1,2,4-triazolyl)-methyl-4-ethyl-1,3-dioxolane.

Interesting compounds of the formula I in respect of their antimycotic activity are those belonging to the group If, wherein each of $R_a$ and $R_b$ independently of the other is hydrogen, halogen or $C_1$–$C_3$alkyl, Ar is the group

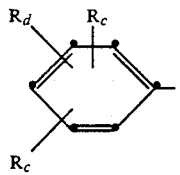

wherein each of $R_c$, $R_d$ and $R_e$ independently of the other is hydrogen, halogen, $CF_3$, $C_1$–$C_3$alkyl, $C_1$–$C_3$alkoxy, and Az, U and V are as defined for formula I.

Within subgroup If, preferred compounds of the formula I in respect of their antimycotic activity are those in which each of U and V independently of the other is $C_1$–$C_6$alkyl, $C_2$–$C_4$alkyl which is unsubstituted or substituted by halogen or $C_1$–$C_2$alkoxy, or together form one of the following alkylene groups

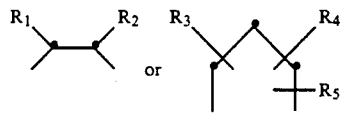

wherein each of $R_1$, $R_2$, $R_3$, $R_4$ and $R_5$ independently of the other is hydrogen or $C_1$–$C_4$alkyl, the total number of carbon atoms in $R_3$, $R_4$ and $R_5$ not exceeding 6. This group will be designated group Ig.

Within subgroup Ig, preferred compounds of the formula I in respect of their antimycotic activity are those in which U and V together are the alicylene group

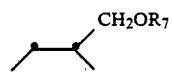

wherein $R_7$ is $C_1$–$C_4$alkyl, $C_2$–$C_4$alkyl which is substituted by $C_1$–$C_2$alkoxy, or is $C_3$–$C_4$alkenyl or prop-2-ynyl. This group will be designated group Ih.

A further preferred group of compounds of the formula I having antimycotic activity comprises those in which Az is imidazolyl, Ar is as defined for formula I, each of $R_a$ and $R_b$ independently of the other is hydrogen, methyl, chlorine or bromine, each of $R_c$, $R_d$ and $R_e$ independently of the other is hydrogen, fluorine, chlorine, bromine, methyl, methoxy, $CF_3$ or nitro, each of U and V independently of the other is $C_1$–$C_3$alkyl which is unsubsituted or substituted by $C_1$–$C_2$alkoxy or chlorine, or together form one of the alkylene groups as defined for formula I, wherein each of $R_1$, $R_2$,$R_3$, $R_4$, $R_5$ and $R_6$ independently of the other is hydrogen or $C_1$–$C_3$alkyl, or $R_1$ is —$CH_2OR_7$, wherein $R_7$ is $C_1$–$C_3$alkyl, $C_2$–$C_3$alkyl which is substituted by $C_1$–$C_2$ alkoxy, or is $C_3$–$C_4$alkenyl. This group will be designated group Ii.

The following individual compounds may be cited as exemplifying particularly preferred compounds having antimycotic activity:

2-[p-(phenoxy)phenyl]-2-[1-(1H-1,2,4-triazolyl)methyl]-4-methyl-5-methyl-1,3-dioxolane;

2-[p-(phenoxy)phenyl]-2-[1-(1H-1,2,4-triazolyl)methyl]-1,3dioxane;

2-[p-(phenoxy)phenyl]-2-(1-imidazolylmethyl)-4-ethyl-1,3dioxolane;

2-[p-(2',4'-dimethylphenoxy)phenyl]-2-(1-imidazolylmethyl)-4-ethyl-1,3-dioxolane;

2-[p-(3'-chlorophenoxy)phenyl]-2-(1-imidazolylmethyl)-4-ethyl-1,3-dioxolane;

2-[p-(4'chlorophenoxy)phenyl]-2-(1-imidazolylmethyl)-4-ethyl-1,3-dioxolane;

2-[p-(3'trifluoromethylphenoxy)phenyl]-2-(1-imidazolylmethyl)-4-ethyl-1,3-dioxolane;

2-[p-(4'-chloro-3'methylphenoxy)phenyl]-2-(1-imidazolylmethyl)-4-ethyl-1,3-dioxolane;

2-[p-(3',4'-dichlorophenoxy)phenyl]-2-(1-imidazolylmethyl)-4-ethyl-1,3-dioxolane;

2-[p-(2',5'-dicihlorophenoxy)phenyl]-2-(1-imidazolylmethyl)-4-ethyl-1,3-dioxolane;

2-[p-(3',4'dichlorophenoxy)phenyl]-2-(1-imidazolylmethyl)-4-methoxymethyl-1,3-dioxolane;

2-[p-(4'-fluorophenoxy)phenyl]-2-(1-imidazolylmethyl)-4-ethyl-1,3-dioxolane;

2-[p-(4'-fluorophenoxy)phenyl]-2-(1-imidazolylmethyl)-4-methyl-5-methyl-1,3-dioxolane;
2-[p-(phenoxy)-2'-methylphenyl]-2-(1-imidazolylmethyl)-4-ethyl-1,3-dioxolane;
2-[p-(4'-chlorophenoxy)-2'-methylphenyl]-2-(1-imidazolylmethyl)-4-methyl-1,3-dioxolane;
2-[p-(4'-fluorophenoxy)-2'-methylphenyl]-2-(1-imidazolylmethyl)-4-methyl-1,3-dioxolane;
including their respective pharmaceutically acceptable acid addition salts, processes for their production, pharmaceutical preparations containina them, and their use as medicaments.

Interesting compounds of the formula I in respect of their anticonvulsive and anxiolytic activity are those belonging to the group Ij, wherein Az is 1H-1,2,4-triazolyl or is imidazolyl optionally substituted by $C_1$-$C_6$-alkyl, each of $R_a$ and $R_b$ independently of the other is hydrogen, halogen or $C_1$-$C_3$alkyl, Ar is phenyl or phenyl which is substituted by $C_1$-$C_3$alkyl, $C_1$-$C_3$alkoxy, $CF_3$ or halogen, and U and V are as defined for formula I. Among the latter group those compounds form a specific sub-group wherein Az is 1H-1,2,4triazolyl or unsubstituted imidazolyl.

Within subgroup Ij, compounds of the formula I having aistinctly useful anticonvulsive ana anxiolytic properties are those in which Az is as defined for formula I, each of $R_a$ and $R_b$ independently of the other is hydrogen, methyl, chlorine or bromine, Ar is phenyl or phenyl which is substituted by halogen, methyl or $CF_3$, and each of U and V independently of the other is $C_1$-$C_3$alkyl, $C_2$-$C_3$alkyl which is unsubstituted or substituted by $C_1$-$C_2$ alkoxy, or together form one of the following alkylene groups

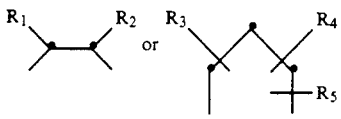

wherein each of $R_1$, $R_2$, $R_3$, $R_4$ and $R_5$ independently of the other is hydrogen or $C_1$-$C_4$alkyl, the total number of carbon atoms in $R_3$, $R_4$ and $R_5$ not exceeding 4. This group will be designated group Ik.

A further preferred group of compounds having pronounced anticonvulsive and anxiolytic properties comprises those in which Az is 1H-1,2,4-triazolyl or is optionally substituted imidazolyl, $R_a$ and $R_b$ are hydrogen, Ar is phenyl or phenyl which is substituted by halogen or methyl, and U and V together are a group of the formula

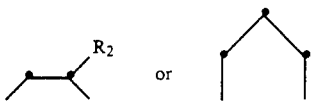

wherein $R_2$ is $C_1$-$C_4$alkyl such as methyl or ethyl, or $C_1$-$C_3$hydroxyalkyl such as hydroxymethyl or 2-hydroxyethyl, or $C_1$-$C_2$alkoxy-$C_1$-$C_2$alkyl such as methoxymethyl or ethoxymethyl. This group will be designated group Il.

The following individual compounds may be cited as exemplifying particularly preferred compounds having anticonvulsive, antidepressive and/or anxiolytic properties:

2-[p-(phenoxy)phenyl]-2-[1-(1H-1,2,4-triazolyl)methyl]-1,3dioxane;
2-[p-(4'chlorophenoxy)phenyl]-2-(1-imidazolylmethyl)-4-ethyl-1,3-dioxolane;
2-[p-(4'chloro-2'methylphenoxy)phenyl]-2-(1-imidazolylmethyl)-4-methoxymethyl-1,3-dioxolane;
2-[p-(phenoxy)phenyl]-2-[1-(1H-1,2,4-triazolyl)methyl]-4-hydroxymethyl-1,3-dioxolane;
2-[p-(4'fluorophenoxy)phenyl]-2-(1-imidazolylmethyl)-4-ethyl-1,3-dioxolane;
2-[p-(4'-fluorophenoxy)phenyl]-2-(1-imidazolylmethyl)-4-hydroxymethyl-1,3-dioxolane;
2-[p-(4'fluorophenoxy)phenyl]-2-[1-(1H-1,2,4-triazolyl)-methyl]-1,3-dioxane
2-[p-(phenoxy)-2'-methylphenyl]-2-(1-imidazolylmethyl)1,3-dioxolane;
2-[p-(4'-chlorophenoxy)phenyl]-2-[1-(1H-1,2,4-triazolyl)methyl]-4-methoxymethyl-1,3-dioxolane;
2-[p-(phenoxy)phenyl]-2-[1-(1H-1,2,4-triazolyl)methyll-4-methyl-1,3-dioxolane;
2-[p-(phenoxy)-2'-chlorophenyl]-2-[1-(1H-1,2,4-triazolyl)-methyl]-4-ethyl-1,3-dioxolane;
2-[p-(4'-chlorophenoxy)-2'-chlorophenyl]-2-[1-(1H-1,2,4triazolyl)methyl]-4-ethyl-1,3-dioxolane;
2-[p-(phenoxy)-2',5'-dimethylphenyl]-2-(1-imidazolylmethyl)4-ethyl-1,3-dioxolane;
2-[p-(4'- chlorophenoxy)phenyl]-2-[1-(1H-1,2,4-triazolyl)methyl]3,4-dimethyl-1,3-dioxolane;
2-[p-(4'fluorophenoxy)-2'-methylphenyl]-2-(1-imidazolylmethyl)-4-ethyl-1,3-dioxolane;
2-[p-(4'-chlorophenoxy)phenyl]-2-(1-imidazolylmethyl)-1,3dioxane;
2-[p-(4'-fluorophenoxy)phenyl]-2-(1-imidazolylmethyl)-1,3dioxane;
2-[p-(4'-chlorophenoxy)phenyl]-2-[1-(2'-methylimidazolyl)methyl]-4-ethyl-1,3-dioxolane;
together with their respective pharmaceutically acceptable acid addition salts, processes for their production, pharmaceutical preparations containing them, and their use as medicaments.

The compounds of formula I may be obtained by A) condensing a compound of the formula II $$Me-Az \qquad (II),$$

wherein Me is hydrogen or a metal cation, with a compound of the formula III

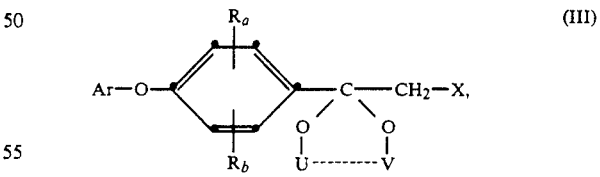

wherein X is a leaving group, or

B) in a compound of the formula IV

converting the carbonyl group into a group of the formula V

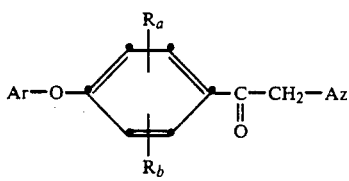 (IV)

or

C) condensing compounds of the formulae VI and VII

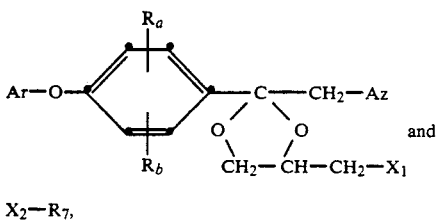 (VI)

and $X_2-R_7$, (VII)

wherein one of the radicals $X_1$ and $X_2$ is hydroxyl or mercapto which may be in salt form, e.g. of the formula —Z—Me, and the other is a leaving group X, or both $X_1$ and $X_2$ are hydroxyl groups, with each other to give compounds of the formula I, wherein U and V together are a group of the formula —CH$_2$—CH(CH$_2$ZR$_7'$)- —and R$_7'$ is a radical which differs from hydrogen, or D) condensing compounds of the formulae VIII and IX Ar—X$_3$ and (VIII)

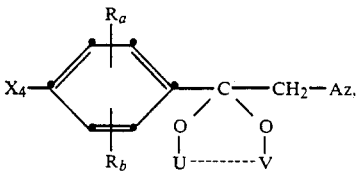 (IX)

wherein one of the radicals $X_3$ and $X_4$ is an O-Me group, in which Me is hydrogen or preferably a metal cation, and the other is a radical which is replaceable by aryloxy, with each other, or E) subjecting a compound of the formula

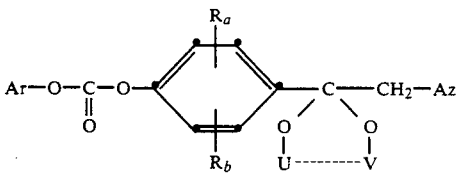 (X)

to intramolecular decarboxylation and, if desired, converting a resultant compound into another compound of the formula I and/or converting a free compound into an acid addition salt, an acid addition salt into the free compound or into another acid addition salt, or convertin, a free compound or acid addition salt into a metal complex.

Examples of metal cations Me are alkali metal cations, e.g. lithium, sodium or potassium cations, or alkaline earth metal cations, e.g. magnesium, strontium or barium cations.

Leaving groups are e.g. reactive esterified hydroxyl groups, such as hydroxyl groups which are esterified with a hydrohalic acid, e.g. with hydrofluoric, hydrochloric, hydrobromic or hydriodic acid, or with a lower alkanesulfonic acid, an unsubstituted or substituted benzenesulfonic or a halosulfonic acid, e.g. with methanesulfonic acid, ethanesulfonic acid, benzenesulfonic acid, p-toluenesulfonic acid or fli-iorosulfonic acid.

The reaction of an azole of the formula II

Me—Az (II), wherein Az is as defined in formula I and Me is preferably a metal atom, especially an alkali metal atom, with a compound of the formula III

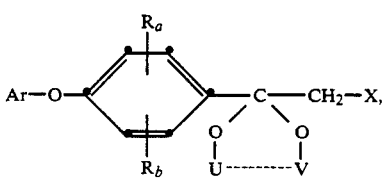 (III)

wherein Ar, $R_a$, $R_b$, U and V are as defined for formula I and X is e.g. halogen, in particular chlorine, bromine or iodine, or benzenesulfonyloxy, p-tosyloxy, trifluoroacetyloxy or, preferably, lower alkylsulfonyloxy, e.g. mesyloxy, is preferably conducted in a relatively polar but inert organic solvent, e.g. N,N-dimethyl formamide, N,N-dimethyl acetamide, dimethyl sulfoxide, acetonitrile, benzonitrile and the like. Such solvents may be employed in combination with other inert solvents such as aliphatic or aromatic hydrocarbons, e.g. benzene, toluene, xylene, hexane, petroleum ether, chlorobenzene, nitrobenzene, etc.

If X is chlorine or bromine, an alkali iodide (such as NaI or KI) may conveniently be added in order to speed up the reaction. Elevated temperatures in the range from 0° to 220° C., preferably from 80° to 170° C., are advantageous. It is advantageous to heat the reaction mixture under reflux.

Where Me in formula II is hydrogen, the process is carried out in the presence of a base. Examples of suitable bases are inorganic bases such as the oxides, hydroxides, hydrides, carbonates and bicarbonates of alkali metals and alkaline earth metals, as well as organic bases e.g. tertiary amines such as triethylamine, triethylenediamine, piperidine, pyridine, 4-dimethylaminopyridine, 4-pyrrolidylpyridine etc.

In this process variant, and in the subsequent ones, the intermediates and final products may be isolated from the reaction medium and, if desired, purified by one of the methods conventionally employed, e.g. by extraction, crystallisation, chromatography, distillation etc.

The conversion of the carbonyl group in compounds of the formula IV into the group of the formula V is carried out by reaction with an orthocarboxylic acid $C_1$-$C_{12}$ trialkyl ester, the $C_1$-$C_{12}$ alkyl groups of which may be substituted by halogen or $C_1$-$C_6$alkoxy, or in the presence of an acid, with at least 2 moles of a monohydric alcohol of the formula U—OH (Va), to give compounds of the formula I in which U and V are identical unsubstituted or substituted $C_1$-$C_{12}$ alkyl groups, or by reaction with a diol of the formula Vb HO—U—V—OH (Vb)

to give compounds of the formula I, wherein U and V together are one of the alkylene bridges defined at the outset. In the foregoing, Ar, Y, $R_a$, $R_b$, U and V are as defined for formula I.

This ketalisation reaction may be carried out in similar manner to already known ketalisation reactions, e.g. in similar manner to the preparation of 2-bromomethyl-2,4-diphenyl-1,3-dioxolane [Synthesis, 1974 (I), 23].

In the preferred embodiment of the ketalisation, both reactants are heated for several hours under reflux together with an azeotrope former in a conventional organic solvent. Examples of suitable azeotrope formers are benzene, toluene, xylene, chloroform or carbon tetrachloride. To hasten the reaction it may be convenient to add a strong acid, e.g. p-toluenesulfonic acid. Examples of organic solvents which may be used are in this case aromatic hydrocarbons such as benzene, toluene, xylene etc., saturated hydrocarbons such as n-hexane, or saturated halogenated hydrocarbons such as 1,1,1-trichloroethane.

The ketalisation may also be carried out by other methods, e.g. by reacting a ketone (IV) which has been ketalised with an alcohol or phenol which differs from the alkanol or diol of the formula Va or Vb respectively, and effecting transketalisation with an excess of alkanol Va or diol Vb to a compound (I). The starting material may be obtained by one of process variants A), D) and E).

Compounds of the formula I, wherein U and V in variant C) are together —CH$_2$—CH(CH$_2$ZR$_7$)-, are obtained e.g. by reaction of a compound of the formula VI with a compound of the formula VII, wherein $X_1$ is a —ZH group and $X_2$ is a group X. The reaction is preferably carried out in an inert organic solvent. Examples of suitable solvents for this reaction are N,N-dimethyl formamide, N,N-dimethyl acetamide, hexamethylphosphoric triamide, dimethyl sulfoxide, 4-methyl-3-pentanone etc. Mixtures with other inert solvents, e.g. with aromatic hydrocarbons such as benzene, toluene, xylene etc., may also be used. In some cases it may be convenient to carry out the reaction in the presence of a base in order to speed up the reaction rate. Examples of suitable bases are alkali metal hydrides or alkali metal carbonates. It may also be advantageous in certain cases to convert the compound of the formula VI first into a suitable metal salt. This is preferably accomplished by reaction of VI with a sodium compound, e.g. sodium hydride, sodium hydroxide etc. This salt of the compound of formula VI is subsequently reacted with the compound of formula VII. In order to increase the reaction rate the process may also be carried out in some cases at elevated temperature, preferably in the range from 80° to 130° C. or at the boiling point of the solvent.

Compounds of the formulae VI and VII, wherein $X_1$ is a group X and $X_2$ is a —ZH group, may also be reacted in similar manner.

In the condensation reaction of compounds of the formulae VI and VII, wherein $X_1$ and $X_2$ are hydroxyl, to give compounds of the formula I in which Z is oxygen, the reactants can be heated under reflux in a suitable solvent, while simultaneously distilling off water from the reaction mixture as an azeotrope. Suitable solvents are aromatic hydrocarbons such as toluene or the alcohol HO—R$_7$ itself. This reaction is conveniently carried out in the presence of a strong acid, e.g. p-toluenesulfonic acid.

In variant D), a start is preferably made from compounds of the formulae VIII and IX, wherein $X_3$ is an —OMe group and $X_4$ is a leaving group, or conversely $X_3$ is the leaving group and $X_4$ is the —OMe group, whilst $R_a$, $R_b$, U, V, Y and Ar are as defined for formula I and Me is preferably hydrogen. It is advantageous to carry out the reaction under the conditions described for variant A).

In variant E), the compound to be decarboxylated of the formula X, which may be obtained by ketalisation of a compound of the formula XI

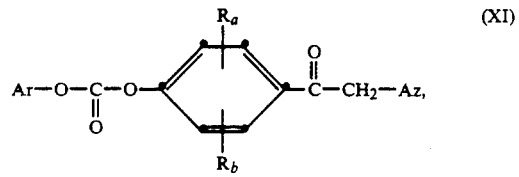

in a manner similar to that described in B), which compound may in turn be obtained by reaction of a compound of the formula AR—OH (XII) with a difunctional derivative of carbonic acid, e.g. with phosgene, a lower alkylester of haloformic acid or with a di-lower allyl or diphenyl carbamate, and further reaction with a compound of the formula XIII

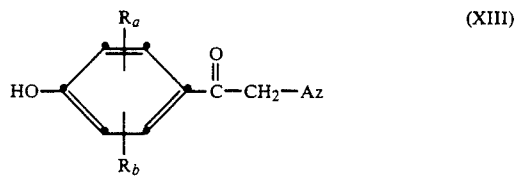

is heated dry or in a high boiling solvent such as a high boiling ether, e.g. diphenyl ether or ethylene glycol dimethyl ether, to about 120° to 220° C.

Compounds obtained by the process of the invention may be converted into other compounds of the formula I by methods which are known per se.

Accordingly, for example, compounds obtained by the process of the invention may be transketalised to other compounds of the formula I. For example, in compounds of the formula I, wherein U and V are identical unsubstituted or substituted $C_1$–$C_{12}$alkyl radicals U, a group U may be replaced by a group V by reaction with 1 mole of another unsubstituted or substituted $C_1$–$C_{12}$alkanol of the formula V—OH (Vc), or both groups U may be replaced by a divalent radical by reaction with a diol of the formula Vb. The transketalisation is carried out in conventional manner, for example in the presence of an acid condensing agent such as a mineral acid, sulfonic acid or strong carboxylic acid, e.g. hydrochloric or hydrobromic acid, sulfuric acid, p-toluenesulfonic acid or trifluoroacetic acid, preferably while removing readily volatile reaction products by distillation or azeotropic distillation.

Further, additional substituents may be introduced, if desired, into the carbocyclic aryl moieties of compounds obtained by the process of the invention. For example, halogen can be introduced by reaction with a halogen in the presence of a Lewis acid, e.g. an iron, zinc, boron or antimony halide, or by treatment with N-chlorosuccinimide.

In addition, nitro groups can be reduced to amines, e.g. by means of suitable complex hydrides, e.g. with lithium aluminium hydride, which amines may then be diazotised, e.g. with nitrous acid, and the diazonium group replaced in customary manner by halogen or alkoxy. Likewise, halogen may be replaced by alkyl by reaction with an alkyl metal compound, e.g. with an alkyl lithium or alkyl magnesium halide.

If the compounds of formula I are obtained as bases, then they can be converted into corresponding salts of the formula I with inorganic or or‚anic acids, or into metal complexes of the formula I by using preferably equimolar amounts of metal salts. Conversely, salts of the formula I can be converted into the.free bases of the formula I by reaction with an alkali carbonate or bicarbonate or an alkali hydroxide.

The starting ketals of the formula III can be obtained from the methyl aryl ketone of the formula XIV

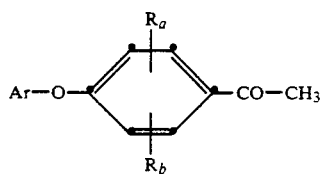

(XIV)

by reaction with the desired diol in an inert solvent, e.g. a halogenated hydrocarbon (such as methylene chloride, ethylene chloride, chloroform, carbon tetrachloride etc.), and simultaneous or subsequent halogenation. It is advantageous to add p-toluenesulfonic acid in order to speed up the reaction.

The ketones of the formula IV can be obtained by halogenation of the starting ketones XIV to XV

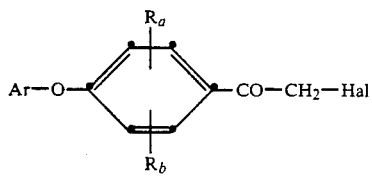

(XV)

and further reaction of XV, in similar manner to variant A), with an azole of the formula II. Hal in formula XV is preferably chlorine or bromine.

The ketals III, VI, IX and X are obtained in similar manner to variant B) by reacting the starting ketone e.g. of the formula IV with a suitable alcohol or diol.

The process variants described above likewise constitute an object of the present invention.

All the above described ketalisation reactions of a ketone with a substituted $\alpha,\beta$- or $\alpha,\gamma$-diol result in the formation primarily of mixtures of diastereoisomers of the resultant ketal. Likewise, mixtures of diastereoisomers of the final products of the formula I are generally obtained from the starting ketones. The compounds of formula I may be obtained e.g. in the two following diastereoisomeric forms:

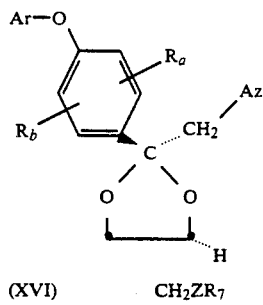

(XVI)  CH$_2$ZR$_7$ type A

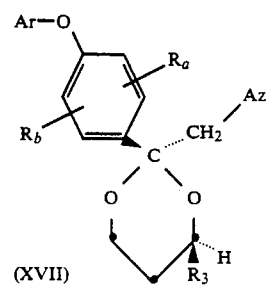

(XVII)

The configuration of type A will be designated here and referred to subsequently as "trans"-isomer.

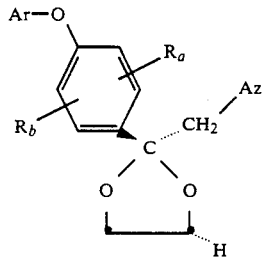

(XVIII)  CH$_2$ZR$_7$ type B

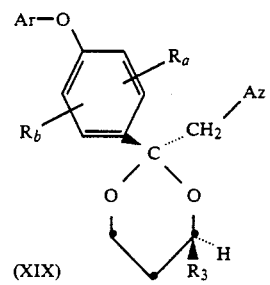

(XIX)

The symbols in the three-dimensional structures reproduced above have the following meanings:
.... = behind
— = in
▬ = in front of the drawing plane.

The configuration of type B will be correspondingly designated as "cis"-isomer. The separation of the two diastereoisomers may be effected e.g. by fractional crystallisation or by chromatography (thin-layer chromatography, column chromatography, liquid high-pressure chromatography etc.). The two isomers have different biological uroperties. Furthermore each of the diastereoisomers is generally obtained as a mixture of two enantiomers. The enantiomers can be separated by methods which are known per se. For practical purposes the mixtures of diastereoisomers will normally be used.

The invention relates to all isomeric compounds of the formula I, and the salts and metal complexes thereof.

The process for obtaining compounds of the formula I as described in variants A, B, C, and E likewise constitutes an object of the invention.

Some of the starting materials and intermediates employed in process variants A, B, C, D and E are known, and others can be prepared by methods which are known per se. Some are novel and their preparation is described herein.

1-($\beta$-Aryl)ethimidazolyl ketals, wherein aryl denotes substituted phenyl or naphthyl, are described as fungicides and bactericides in the following references: U.S. Pat. Nos. 3,575,999, 3,936,470, 4,101,664, 4,101,666 and 4,156,008.

Surprisingly, it has been found that compounds of the formula I have for practical purposes a very advantageous microbicidal spectrum against phytopathogenic fungi and bacteria, as well as antimycotic and/or anticonvulsive properties which indicate their use as medicaments. For example, the compounds of formula I have very advantageous systemic and especially preventive and curative phytotherapeutic properties and can be used for protecting cultivated plants. They are characterized by a very broad microbicidal activity and an exellent crop tolerance up to high application rates. With the compounds of formula I it is possible to inhibit or destroy the microorganisms which occur in plants or parts of plants (fruit, blossoms, leaves, stems, tubers, roots) in different crops of useful plants, while at the same time the parts of plants which grow later are also protected from attack by such microorganisms.

The compounds of formula I are effective in particular against the phytopathogenic fungi belonging to the following groups: Ascomycetes (e.g. Venturia, Podosphaera, Erysiphe, Monilinia, Uncinula); Basidomycetes (e.g. the genera Hemileia, Rhizoctonia, Puccinis); *Fungi imperfecti* (e.g. Botrytis, Helminthosporium, Fusarium, Piricularia, Septoria, Cercospora and Alternaria). In addition, the compounds of formula I are very active against leafspot diseases. They can also be used as seed dressing agents for protecting seeds (fruit, tubers, grains) and plant cuttings against fungus infections as well as against phytopathogenic microorganisms which occur in the soil. The compounds of the invention are also especially well tolerated by plants.

Accordingly, the invention also relates to microbicidal compositions and to the use of compounds of the formula I for controlling phytopathogenic microorganisms, especially harmful fungi, and for the preventive treatment of plants to protect them fron attack by such microorganisms.

In addition, the invention relates to the preparation of agrochemical compositions, comprising intimately mixing a compound of the formula I with one or more substances or groups of substances described herein. The invention further relates to a method of treating plants, which comprises applying thereto compounds of the formula I or novel compositions containing them.

Target crops to be protected within the scope of the present invention comprise e.g. the following species of plants: cereals (wheat, barley, rye,oats, rice, sorghum and related crops), beet (sugar beet and fodder beet), drupes, pomes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefruit, mandarins), vegetable (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (composites).

The compounds of formula I are normally applied in agriculture in the form of compositions and may be applied to the crop area or plant to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these preparations, if desired together with further carriers, surfactants or application-promoting adjuvants customarily employed in the art of formulation. Suitable carriers and adjuvants for all formulations can be solid or liquid and correspond to the useful non-toxic substances ordinarily employed in formulation technology, e.g. natural or regenerated mineral substances, solvents, dispersants, wetting agents, tackifiers, thickeners or binders.

A preferred method in agriculture of applying a compound of the formula I or an agrochemical composition to an infested plant, is foliar (leaf) application. The number of applications and the rate of application depend on the intensity of infestation by the corresponding pathogen (type of fungus). However, the compounds of formula I can also penetrate the plant through the roots via the soil (systemic action) by impregnating the locus of the plant with a liquid composition, or by applying the compounds in solid form to the soil granular form (soil application). The compounds of formula I may also be applied to seeds (coating), by impregnating the seeds either with a liquid formulation containing a compound of the formula I, or coating them with a solid formulation. In special cases, further types of application are also possible, e.g. selective treatment of the plant stems or buds.

The compounds of the formula I are used in unmodified form or, preferably, together with the adjuvants conventionally employed in the art of formulation, and are therefore formulated in known manner to emulsifiable concentrates,, coatable pastes, directly sprayable or dilutable solutions, dilute emulsions, wettable powders, soluble powders, dusts, granulates, and also encapsulations in e.g. polymer substances. Like the nature of the compositions, the methods of application, such as spraying, atomising, dusting, scattering or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The agrochemical formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders,, e.g. solvent, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalates or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers such as calcite, talcumkaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyl taurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and altkylpolypropylene glycol containing 1 to 10 carbon atoms in the alkyl chain, which adducts contain 20 to 250 ethylene glycol ether groups and 10 to 100 prpylene glycol ether groups. These compounds usually contain 1 to 5 ethylene glycol units per propylene glycol unit.

Representative examples of non-ionic surfactants are nonylphenolpolyethoxyethanols, castor oil polyglycol ethers) polypropylene/Polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ringwood, New Jersey, 1979, and Sisely and Wood, "Encyclopedia of Surface Active Agents", Chemical Publishing Co., Inc. New York, 1980.

The agrochemical compositions usually contain 0.1 to 99%, preferably 0.1 to 95%, of a compound of the formula I, 99.9 to 1%, preferably 99.8 to 5%, of a solid or liquid adjuvant, and among the adjuvants 0 to 25%, preferably 0.1 to 25% of a surfactant.

Whereas commercial products are preferably formulated as concentrates, the end user will normally employ dilute formulations.

The compositions may also contain further ingredients, such as stabilisers, antifoams, viscosity regulators, binders, tackifiers as well as fertilisers or other active ingredients in order to obtain special effects.

Such agrochemical compositions also constitute an object of the present invention.

The antimycotic properties which indicate the utility of the compounds of the formula I and their pharmaceutically acceptable acid addition salts for controlling parasitic fungi in warm-blooded animals, may be demonstrated e.g. in vitro by means of conventional microbiological test methods, e.g. by determining their toxic action against fungus strains which are parasites of warm-blooded animals, for example a,ainst Trychophyton mentagryphites, Microsporum canis, Sporotrichum schenkii, Aspergillus fumigatus and Candida albicans; and also in vivo in guinea pigs by determining the curative effect on experimental infestations on the dorsal skin with Trichophyton, e.g. *T. rubrum*, after peroral or local application.

The anticonvulsive properties of the compounds of formula I and their pharmaceutically acceptable acid addition salts may be demonstrated in vivo e.g. in mice by means of the pentatetrazole spasm test in the dose range from about 10 to 100 mg/kg p.o., and also by means of the electroshock test in the dose range from about 10 to 100 mg/kg p.o. The anxiolytic properties can be demonstrated e.g. in mice and other small rodents by means of the Gellert test and the Quatre-Plaque test in the dose range from about 10 to 100 mg/kg p.o. It may also be inferred that the novel compounds have significant antimanic properties.

Accordingly, the present invention also relates to the use of compounds of the formula I and their pharmaceutically acceptable acid addition salts for the topical, local and systemic control of fungi which are parasites of warm-blooded animals, and for the systemic treatment of different forms of epilepsy, of states of anxiety and tension and of manic states of mind, in particular as active ingredients of pharmaceutical preparations, or for the production of pharmaceutical preparations, for enteral or parenteral or topical or local application, and relates also to such pharmaceutical preparations.

The pharmaceutical preparations of this invention which contain compounds of the formula I or pharmaceutically acceptable salts thereof, are accordingly those for enteral, such as oral or rectal, and parenteral, administration, as well as for topical application to warm-blooded animals, which preparations contain the pharmacological active ingredient alone or together with a pharmaceutically acceptable carrier therefor. The dosage of the active ingredient depends on the species of warm-blooded animal, on the age and individual condition of the patient, and on the mode of administration or application.

For oral administration to a warm-blooded animal having a body weight of about 75 kg the approximate daily dose will normally be from 50 to 500 mg, conveniently distributed over several equal partial doses.

The pharmaceutical preparations of this invention contain e.g. from about 10% to 80%, preferably from about 20% to 60%, of active ingredient. Pharmaceutical preparations for enteral or parenteral administration are e.g. those in dosage unit form such as dragées, tablets, capsules or suppositories and also ampoules. These are prepared in a manner known per se, e.g. by conventional mixing, granulating, sugar-coating, dissolving or lyophilising methods. Thus pharmaceutical preparations for oral administration may be obtained by combining the active ingredient with solid carriers, optionally granulating the resultant mixture and, if desired or necessary, after addition of suitable adjuncts, processing the mixture or granulate to tablets or dragée cores.

Suitable carriers for tablets and/or draggées are in particular fillers such as sugar, for example, lactose, saccharose, mannitol or sorbitol, cellulose preparations and/or calcium phosphates, e.g. tricalcium phosphate or calcium hydrogen phosphate, also binders such as starch pastes, for example maize, corn, rice or potato starch paste, gelatin, tragacanth, methyl cellulose, hydroxypropylmethylcellulose, sodium carboxymethylcellulose and/or polyvinylpyrrolidone, and/or, if desired, disintegrators, such as the above starches, also carboxymethyl starch, crosslinked polyvinylpyrrolidone, agar, alginic acid or a salt thereof, such as sodium alginate. Adjuncts are chiefly glidants and lubricants, for example, silicic acid, talc, stearic acid or salts thereof,, such as magnesium stearate or calcium stearate, and/or polyethylene glycol. Sugar-coated tablet cores are provided with suitable coatings that can be resistant to gastric juices, using, inter alia, concentrated sugar solutions which may contain gum arabic, talc, polyvinylpyrrolidone, polyethylene glycol and/or titanium dioxide, shellac solutions in suitable organic solvents or solvent mixtures or, for the preparation of coatings resistant to gastric juices, solutions of suitable cellulose preparations, such as acetylcellulose phthalate or hydroxypropylmethylcellulose phthalate. Dyes or pigments can be added to the tablets or dragées cores, for example to identify or indicate different doses of active ingredient.

Further pharmaceutical preparations for oral administration are dry-filled capsules, and also soft sealed capsules made from gelatin and a plasticiser, such as glycerol or sorbitol. The dry-filled capsules may contain the active ingredient in the form of granules, for example in admixture with fillers such as lactose, binders such as starch and/or lubricants such as talcum or magnesium stearate, and optionally stabilisers. In soft capsules, the active ingredient is preferably dissolved or suspended in suitable liquids, for example in fatty oils, paraffin oil or liquid polyethylene glycols, to which stabilisers can also be added.

Suitable dosage forms for rectal administration are for example suppositories, which consist of a combination of the active ingredient with a suppository base. Examples of suitable suppository bases are natural or synthetic triglycerides, paraffin hydrocarbons, polyethylene glycols or higher alcohols. Gelatin rectal capsules, which consist of a combination of the active components with a base material, can also be employed. Suitable base materials are for example liquid triglycerides, polyethylene glycols or paraffin hydrocarbons.

Particularly suitable for parenteral administration are aqueous solutions of an active ingredient in water-soluble form, e.g. a water-soluble salt, and also suspensions of the active ingredient such as suitable oily injection suspensions for which suitable lipophilic solvents or vehicles such as fatty oils, e.g. sesame oil, or synthetic fatty acid esters, e.g. ethyl oleate or triglycerides, are used, or aqueous injection suspensions which contain substances which increase the viscosity, e.g. sodium carboxymethylcellulose, sorbitol and/or dextrane, and, if desired, also stabilisers.

Pharmaceutical preparations for topical application are e.g. creams, ointments, pastes, foams, tinctures and solutions, which contain the active ingredient in an amount from about 0.5% to about 20%.

Creams are oil-in-water emulsions which contain more than 50% of water. Fatty alcohols are chiefly used as oleaginous base, for example lauryl, cetyl or stearyl alcohol, fatty acids, for example palmitic or stearic acid, liquid to solid waxes, for example isopropyl myristate, wool wax or bees-wax, and/or hydrocarbons, for example petroleum jelly (petrolatum) or paraffin oil. Suitable emulsifiers are surface-active substances with primarily hydrophilic properties, such as corresponding non-ionic emulsifiers, for example fatty acid esters of polyalcohols or ethylene oxide adducts thereof, such as polyglycerol fatty acid esters or polyoxyethylene sorbitan fatty acid esters (Tweens); polyoxyethylene fatty alcohol ethers or esters, or corresponding ionic emulsifiers, such as alkali metal salts of fatty alcohol sulfates, for example sodium lauryl sulfate, sodium cetyl sulfate or sodium stearyl sulfate, which are customarily used in the presence of fatty alcohol, for example cetyl alcohol or stearyl alcohol. Additives to the water phase include agents which reduce water loss through evaporation, for example polyalcohols, such as glycerol, sorbitol, propylene glycol and/or polyethylene glycols, as well as preservatives, perfumes etc.

Ointments are water-in-oil emulsions which contain up to 70%, but preferably from about 20% to 50%, of water or aqueous phase. The oleaginous phase comprises chiefly hydrocarbons, for example petroleum jelly, paraffin oil and/or hard paraffins, which contain preferably hydroxy compounds suitable for improving the water-absorption, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the water phase include humectants, such as polyalcohols, for example glycerol, propylene glycol, sorbitol and/or polyethylene glycol, and preservatives, perfumes etc.

Greasy ointments are anhydrous and contain as base in particular hydrocarbons, for example paraffin, petroleum jelly and/or liquid paraffins, furthermore natural or partially synthetic fat, for example coconut fatty acid triglycerides, or preferably hardened oils, for example hydrated ground nut or castor oil, and also fatty acid partial esters of glycerol, for example glycerol mono- and distearate, and, for example, the fatty alcohols, emulsifiers and/or additives for increasing the water-absorption mentioned in connection with the ointments.

Pastes are creams and ointments containing powdered ingredients which absorb secretions, such as metal oxides, for example titanium oxide or zinc oxide, and talc and/or aluminium silicates whose purpose it is to bind moisture or secretion present.

Foams are administered from pressurised dispensers and are liquid oil-in-water emulsions in aerosol form, with halogenated hydrocarbons such as chlorofluoro-lower alkanes, for example dichlorodifluoromethane and dichlorotetrafluoroethane, being used as propellants. For the oleaginous phase there are used, inter alia, hydrocarbons, for example paraffin oil, fatty alcohols, for example cetyl alcohol, fatty acid esters, for example isopropyl myristate, and/or other waxes. As emulsifiers there are used, inter alia, mixtures of these emulsifiers with primarily hydrophilic properties, such as polyoxyethylene sorbitan fatty acid esters (Tweens), and those with primarily lipophilic properties, such as sorbitan fatty acid esters (Spans). In addition, the conventional additives are used, such as preservatives etc.

Tinctures and solutions generally have an aqueous ethanolic base to which are added, inter alia, polyalcohols, for example glycerol, glycols, and/or polyethylene glycol, as humectants for reducing water loss, and fat-restoring substances, such as fatty acid esters with lower polyethylene glycols, i.e. lipophilic substances which are soluble in the aqueous mixture as substitute for fatty substances which are taken from the skin with the ethanol, and, if necessary, other assistants and additives.

The pharmaceutical conpositions for topical application are obtained in known manner, for example by dissolving or suspending the active ingredient in the base or in a part thereof, if necessary. When processing the active ingredient in the form of a solution, it is usually dissolved in one of the two phases before the emulsification, and when processing the active ingredient in the form of a suspension, it is mixed with a part of the base before the emulsification and then added to the remainder of the formulation.

The following Examples will serve to illustrate the invention in more detail, but without implying any restriction to what is described therein. Parts and percentages are by weight and pressures are in millibars (mbar).

PREPARATORY EXAMPLES

Example 1:

Preparation of

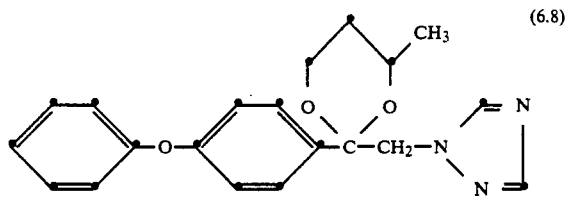

(6.8)

2-lp-(Phenoxy)phenyl]-2-[1-(1H-1,2,4-triazolyl)methyll-4-methyl-1,3-dioxane a) Preparation of the Intermediate

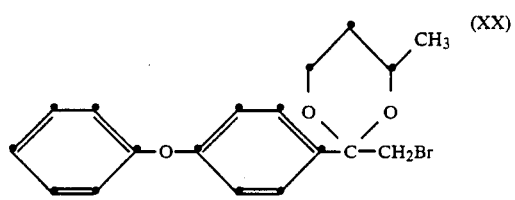

(XX)

2-[p-(Phenoxy)phenyl]-2-bromomethyl-4-methyl-1,3-dioxane 10 parts of 2-[p-(phenoxy)phenyll-2-oxy-l-bromoethane and 4 parts of 1,3-butanediol are heated under reflux for 3 hours in 40 ml of absolute toluene in the presence of 0.2 part of p-toluenesulfonic acid as catalyst, while removing the water of reaction with a water separator. The reaction mixture is cooled to room temperature, then washed with two 20 ml portions of water, dried over sodium sulfate and filtered. The solvent is removed by evaporation and the crude product is recrystallised from isopropanol to give colourless crystals with a melting point of 96°–106° C.

b) Preparation of the Final Product 3.3 parts of the sodium salt of 1,2,4-triazole and a catalytic amount of potassium iodide are stirred in 40 ml of dimethyl sulfoxide together with 10.2 parts of the 2-[p-(phenoxy)phenyl ]-2-bromomethyl-4-methyl-1,3-dioxane obtained in a) for 30 hours at a temperature of 120° C. The reaction mixture is cooled to room temperature, then diluted with 300 ml of water and extracted with three 30 ml portions of ethyl acetate. The combined extracts are washed with two 20 ml portions of water, dried over sodium sulfate, filtered, and the solvent is removed by evaporation. The oily residue is purified by column chromatography over silica gel with ethyl acetate. The eluant is removed by evaporation and the oily residue crystallises from petroleum ether to give brownish crystals with a melting point of 99.5°–101° C.

Example 2

Preparation of

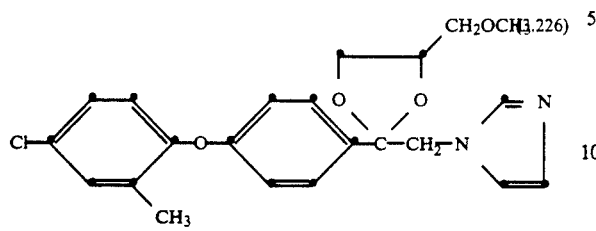

2-[p-(4-Chloro-2-methylphenoxy)phenyl]-2-(1-imidazolyl-methyl)-4-methoxymethyl-1,3-dioxolan 16 parts of 2-[p-(4-chloro-2-methylphenoxy)phenyl]-2-(1-imidazolylmethyl)-4-hydroxymethyl-1,3-dioxolane are dissolved in 150 ml of N,,N-dimethyl formamide and then 1.9 parts of 55% sodium hydride dispersion are stirred in while introducing nitrogen. The mixture is heated for 2 hours to 80° C., then cooled to room temperature, treated dropwise, with stirring, with 6.3 parts of methyl iodide over 1 hour, then heated for 2 hours to 60° C., diluted with 800 ml of ice-water and extracted with three 300 ml portions of ethyl acetate. The combined extracts are washed with two 50 ml portions of water, dried over sodium sulfate, filtered, and the solvent is removed by evaporation. The residue is purified by column chromatography over silica gel with acetone/ethyl acetate (1:1). The eluant is then removed by evaporation and the mixture of diastereoisomers is crystallised by treatment with tiexane, giving beige-coloured crystals with a melting point of 92°-106° C.

Example 3

Preparation of

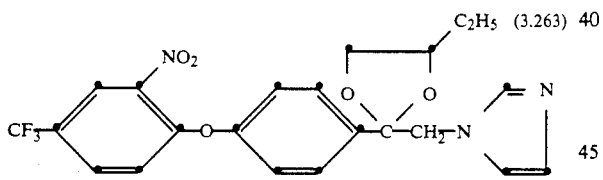

2-[p-(2-Nitro-4-trifluoromethylphenoxy)phenyl]-2-(1-imidazolylmethyl)-4-ethyl-1,3-dioxolane 8.3 parts of 2-[p-(2-nitro-4-trifluoromethylphenoxy)-phenyl]-2-(1-imidazolylmethyl)-4-ethyl-1,3-dioxolane are dissolved in 300 ml of dimethyl sulfoxide and to the solution are added 1.84 parts of ground potassium hydroxide, whereupon the temperature rises from 23° to 36° C. After heating for 2 hours to 70° C., 7.4 parts of 4-chloro-3nitrobenzotrifluoride in 100 ml of dimethyl sulfoxide are added dropwise and stirring is continued for 3 hours at 70° C. The reaction mixture is cooled to room temperature, poured into 2 litres of water and extracted with two 200 ml portions of diethyl ether. The combined extracts are washed with two 70 ml portions of water, dried over sodium sulfate, and the solvent is removed by evaporation. The oily residue is purified by column chromatography over silica gel with ethyl acetate. The eluant is removed by evaporation, leaving as residue a mixture of diastereoisomers in the form of a viscous mass.

Example 4

Synthesis of

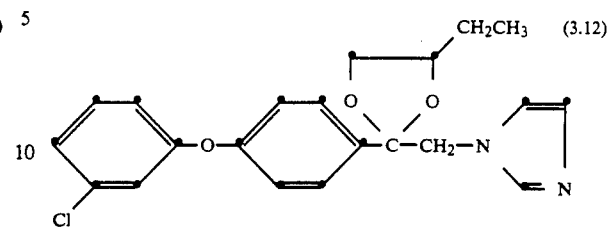

2-[p-(3-Chlorophenoxy)phenyl]-2-(1-imidazolylmethyl)-4-ethyl-1,3-dioxolane 1.2 parts of imidazole sodium salt, 4 parts of 2-[p-(3chlorophenoxy)phenyl]-2-bromomethyl-4-ethyl-1,3-dioxolane and a catalytic amount of potassium iodide are stirred in 50 ml of dimethyl formamide for 17 hours at a temperature of 125° C. The brown reaction mixture is cooled to room temperature, diluted with 150 ml of water and extracted with three 50 ml portions of ethyl acetate. The combined extracts are washed with two 50 ml portions of water, and dried over sodium sulfate. The solvent is removed by evaporation and the crude product is chromatographed over a 35 cm column of silica gel with acetone/ethyl acetate (1:1). The eluant is removed by evaporation and the oily residue is crystallised from petroleum ether in the form of slightly yellowish crystals with a melting point of 69°-71° C.

Example 5

Preparation of

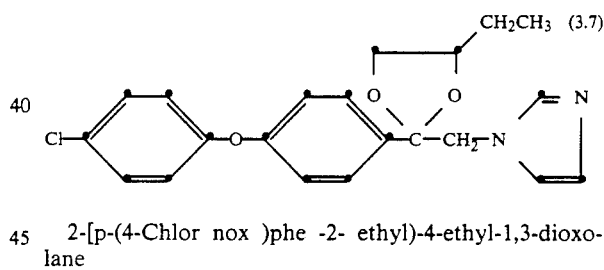

2-[p-(4-Chlor nox )phe -2- ethyl)-4-ethyl-1,3-dioxolane a) Synthesis of the Intermediates α) Preparation of

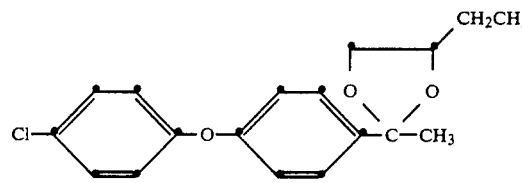

2-fp-(4-Chlorophenoxy)phenyl]-2-methyl-4-ethyl-1,3dioxolane 37 parts of 4-(p-chlorophenoxy)acetophenone, 18 parts of 1,2-butanediol and 2 parts of p-toluenesulfonic acid as catalyst are heated under reflux in 400 ml of absolute toluene for 14 hours on a water separator. The reaction mixture is cooled to room temperature, washed with two 400 ml portions of water, dried over sodium sulfate and filtered. The solvent is removed by evaporation and the crude product is purified over a 1 m column of silica gel with ligroin/hexane/ethyl acetate/toluene (5:3:1:1). The product is obtained in the form of a sli,htly yellowish oil; $n_D^{22}$: 1.5527.

β) Preparation of

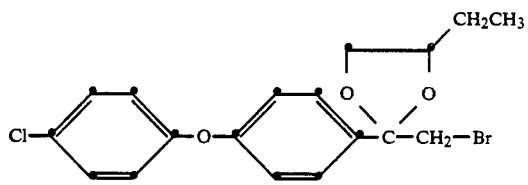

2-[p-(4-Chlorophenoxy)phenyl]-2-bromomethyl-4-ethyl-1,3dioxolane 36.8 parts of 2-[p-(4-chlorophenoxy)phenyll-2-methyl-4-ethyl-1,3-dioxolane obtained in a) are heated to the boil in 350 ml of chloroform. Under irradiation with a 150 watt spot lamp, a solution of 19.4 parts of bromine in 50 ml of chloroform is added dropwise and the reaction mixture is subsequently heated under reflux for 2 hours. The reaction mixture is cooled to room temperature, then washed with two 200 ml portions of water, dried over sodium sulfate and filtered. The solvent is then stripped off under a water jet vacuum. The crude product is purified by chromatography over a 1 m column of silica gel with toluene. The product is obtained in the form of an oil with a refractive index of $n_D^{23}$: 1.5803.

b) Synthesis of the Final Product 4.4 parts of imidazole sodium salt, a catalytic amount of potassium iodide and 14.7 parts of 2-[p-(4-chlorophenoxy)-phenyl]-2-bromomethyl-4-ethyl-1,3 -dioxolane obtained in β) are stirred in 80 ml of dimethyl formamide for 17 hours at a bath temperature of 125° C. The reaction mixture is cooled to room temperature, then poured into 600 ml of water and extracted with three 200 ml portions of ethyl acetate. The combined extracts are washed with two 200 ml portions of water, dried over sodium sulfate and filtered. The solvent is then removed by evaporation and the oily residue is chromatographed over a 50 cm column of silica gel with acetone/ethyl acetate (1:1). The eluant is removed by evaporation and the product is obtained in the form of a brown oil ivith a refractive index of 1.5750.

Example 6

Synthesis of

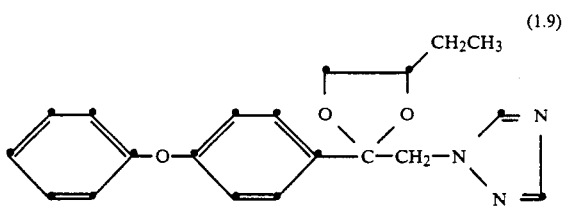

2-[p-(Phenoxy)phenyll-2-(-triazolylmethyl)-4-ethyl1,3-dioxolane 17 parts of 2-[p-(phenoxy)phenyl]-3-bromomethyl-4-ethyl1,3-dioxolane, 8.4 parts of potassium carbonate, 4.2 parts of 1.2,4-triazole and a catalytic amount of sodium iodide are stirred in 100 ml of dimethyl formamide for 24 hours at a temperature of 125° C. The reaction mixture is cooled to room temperature, then poured into 600 ml of water and extracted with three 200 ml portions of ethyl acetate. The combined extracts are washed with 200 ml portions of water, dried over sodium sulfate and filtered. The solvent is removed by evaporation and the oily residue is chromatographed over a 50 cm column of silica el with chloroform/ether (1:1). The eluant is removed by evaporation and the oily residue is crystallised from petroleum ether in the form of white crystals with a melting point of 81.5°-83.5° C.

Example 7

Synthesis of

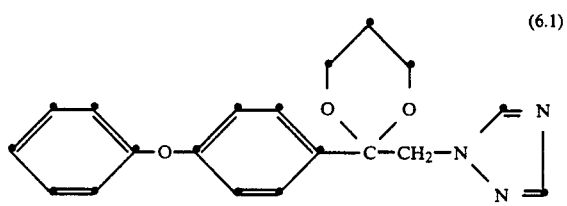

2-[p-(Phenoxy)phenyl]-2-(1H-1,2,4-triazolylmethyl)-1,3dioxane 14 parts of 2-[p-(phenoxyphenyl)-2-bronioniethyl-1,3-dioxane, 7.2 parts of potassium carbonate, 3.6 parts of 1,2,4triazole and a catalytic amount of potassium iodide are stirred in 100 ml of dimethyl formamide for 20 hours at a temperature of 140° C. The reaction mixture is cooled to room temperature, diluted with 600 ml of water and extracted with three 200 ml portions of ether. The combined extracts are washed with two 200 ml portions of water, dried over sodium sulfate and filtered. The solvent is evaporated and the oily residue is chromatographed over a 50 cm column of silica gel with chloroform/etlier (1:1). The eluant is evaporated and the residue is crystallised from petroleum ether in the form of white crystals with a melting point of 129°-130° C.

Example 8

Synthesis of

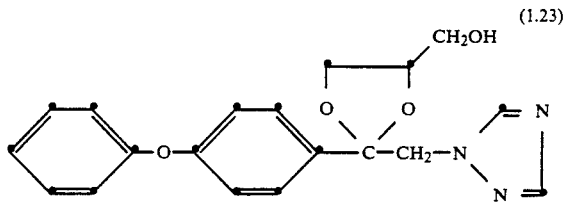

2-[p-(Phenoxy)phenyl]-2-(1H-1,2,4-triazolylmethyl)-4-hydroxymethyl-1,3-dioxolane 4.5 parts of 2-[p-(phenoxy)phenyll-2-bromomethyl-4-hydroxymethyl-1,3-dioxolane, 2.2 parts of potassium carbonate, 1.1 parts of 1,2,4-triazole and a catalytic amount of potassium iodide are stirred in 50 ml of dimethyl sulfoxide for 4 hours at a temperature of 140° C. The reaction mixture is cooled to room temperature, then poured into 600 ml of water and extracted with two 200 ml portions of ethyl acetate. The combined extracts are washed with two 200 ml portions of water, dried over sodium sulfate and filtered. The solvent is evaporated and the oily residue is chromatographed over a 50 cm column of silica gel with acetone. The solvent is evaporated and the oily residue is crystallised fron petroleum ether in the form of beige-coloured crystals with a melting point of 111°-112° C.

Example 9

Synthesis of

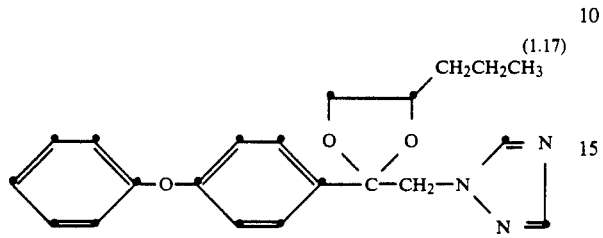

2-[p-(Phenoxy)phenyl]-2-(1H-1,2,4-triazolylmethyl)-4-n-propyl-1,3-dioxolane 10.3 parts of the nitrate of 1-(p-phenoxyphenyl)-2-(1,2,4-triazolyl)-ethanone, 6.1 parts of 1,2-pentanediol, 6.9 parts of p-toluenesulfonic acid, 20 parts of 1-pentanol and 200 parts of xylene, are heated under reflux for 6 days on a water separator. The reaction mixture is then cooled to room temperature and then washed with two 200 ml portions of dilute sodium hydroxide solution and with two 200 ml portions of water. The organic phase is dried over sodium sulfate and filtered. The solvent is evaporated and the oily residue is chromatographed over a 1 m column of silica gel with ethyl acetate. The eluant is evaporated and the oily residue crystallises slowly in the form of beige-coloured crystals with a melting point of 68.5°-71° C.

Example 10

Preparation of

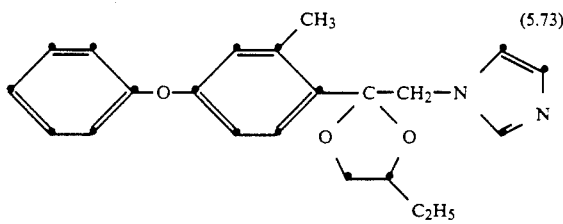

2-[(2'-Methyl-4'-phenoxy)-phenyl]-2-(1-imidazolylmethyl)-4-ethyl-1,3 -dioxolane a) Preparation of the Intermediate

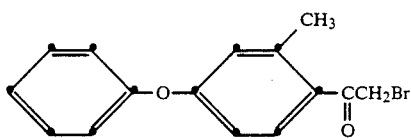

2-Methyl-4-phenoxy-phenacylbromide 36,6 parts of 2-Methyl-4-phenoxy-acetophenone are dissolved in 160 ml acetic acid and heated to 35° C., then 25,9 parts of bromine are added dropwise within 1,5 hours and stirring is continued for 1 hour. The reaction mixture is poured into 1 liter of ice-water and extracted with two 100 ml portions of ethyl ether. The combined extracts are washed with water, dried over sodium sulfate, filtered, and the solvent is removed by evaporation and the oily residue crystallises from n-Hexane to give brownish crystals with a melting point of 60°-61° C.

b) Preparation of the Intermediate

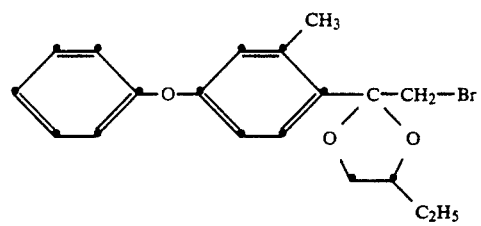

2-[(2'-Methyl-4'-phenoxy)-phenyl]-2-bromomethyl-4-ethyl1,3-dioxolane 85,4 parts of 2-Methyl-4-phenoxyacetylbromide and 25,2 parts of 1,2butanediol are dissolved in 250 ml absolute toluene in the presence of a catalytic amount (1 part) of p-toluenesulfonic acid. The reaction mixture is refluxed for 24 hours on a water separator. Then the reaction mixture is cooled to room temperature, washed with three 250 ml portions of water, dried over sodium sulfate and filtered. The solvent is removed by evaporation and the product is obtained as redbrown oil.

c) Synthesis of the Final Product 9,5 parts of 2-[(2'-Methyl-4'-phenoxy)-phenyl]-2-bromo-methyl-4-ethyl-1,3-dioxolane obtain in b), 2,4 parts of imidazole and 4,0 parts of potassium tert.-butylate are stirred in 50 ml of dimethyl sulfoxide for 30 hours at a temperature of 110° C. The reaction mixture is cooled to room temperature, diluted with 300 ml water and extracted with three 150 ml portions of ethyl acetate. The combined extracts are washed neutral with water, dried over sodium sulfate and filtered. The solvent is removed by evaporation and the crude product is purified over a 50 cm column of silica gel with ethyl acetate. The product is obtained in the form of a reddish oil. $n_D^{50}$: 1.5550.

Example 11

Preparation of

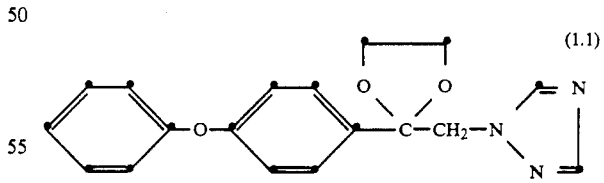

2-[p-(Phenoxy)-phenyl]-2-[1-(1H-1,2,4-triazolyl)-methyl]-1,3-dioxolane 11 parts of 2-[p-(Phenoxycarbonyloxy)-phenyl]-2-[1-(1H-1,2,4-triazolyl)-methyl]-1,3 -dioxolane are heated in 200 ml ethylene glycol diethyl ether (about 10 hours) at a temperature of 130° C. till the end of the carbon dioxid production. Then the solvent is destilled of under reduced pressure. The oily crude product is cooled to room temperature, solved in 500 ml diethyl ether, washed with two portions of 100 ml water, dried over sodium sulfate and filtered. The solvent is removed by evaporation. The crude product is recrystallised from ethyl acetate/cyclohexane in the presence of active carbon to give colourless crystals with a melting point of 100°-102° C.

Example 12
Preparation of the A- and B-Diastereoisomers of

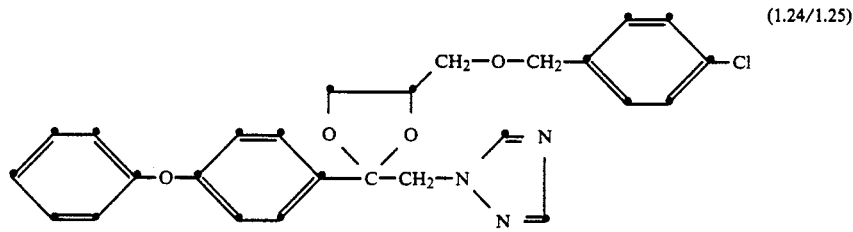

(1.24/1.25)

2-[p-(Phenoxy)-phenyl]-2-(1H-1,2,4-triazolylmethyl)-4-(p-chlorobenzyloxymethyl)1,3-dioxolane 14,1 parts of 2-[p-(Phenoxy)-phenyl]-2-(1H-1,2,4-triazolyl-methyl)-4-hydroxymethyl-1,3-dioxolane dioxolane dissolved in 100 ml absolute dioxane and then 1,8 parts of 55 % sodium hydrid dispersion in 100 ml absolute dioxane are stirred in at room temperature while introducing nitrogen. The mixture is heated 3 hours to 80° C., then cooled to room temperaLure, treated dropwise within 30 minutes with 8,6 parts of p-chlorobenzyl-bromide dissolved in 50 parts of absolute dioxane. The reaction mixture is beated 3 hours to 50° C., then cooled to room temperature, diluted with 1200 ml ice-water and extracted with three 200 ml portions of ethyl acetate. The combined extracts are washed with two 70 ml portions of water, dried over sodium sulfate, filtered and the solvent removed by evaporation. The remaining diastereoisomers are separated by column chromatography (silica gel/ethyl acetate). The eluant is then removed by evaporation to give the diastereoisomer B in the form of crystals with a melting point of 83°-85° C. The diastereoisomer A is obtained after the evaporation of the solvent in form of a viscous slightly brownish oil; $n_D^{26}$: 1.5865.

The following compounds of the formula I can also be prepared in analogous manner (unless otherwise specified, mixtures of diastereoisomers having different mixture ratios):

In the following Tables, the symbol A stands for a diastereoisomer of type A, and B stands for a diastereoisomer of type B.

TABLE 1

Compounds of the formula

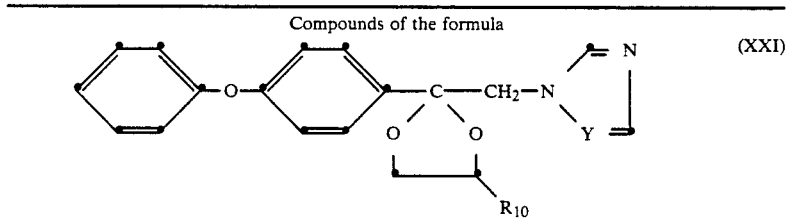

(XXI)

including isomeric forms:

| Compound | $R_{10}$ | Y | Salt | Physical data (°C.) |
|---|---|---|---|---|
| 1.1 | H | N | — | m.p. 100–102° |
| 1.2 | H | N | $HNO_3$ | |
| 1.3 | H | CH | — | |
| 1.4 | $CH_3$ | N | — | m.p. 85–92° |
| 1.5 | $CH_3$ | N | HCl | |
| 1.6 | $CH_3$ | N | $CuCl_2$ | |
| 1.7 | $CH_3$ | CH | — | |
| 1.8 | $CH_3$ | N | $Mn(NO_3)_2$ | |
| 1.9 | $C_2H_5$ | N | — | m.p. 81.5–83.5° |
| 1.10 | $C_2H_5$ | N | $HNO_3$ | |
| 1.11 | $C_2H_5$ | N | $ZnCl_2$ | |
| 1.12 | $C_2H_5$ | N | $Mn(NO_3)_2$ | |
| 1.13 | $C_2H_5$ | N | $FeCl_3$ | |
| 1.14 | $C_2H_5$ | CH | — | light brown oil |
| 1.15 | $C_2H_5$ | CH | $CuCl_2$ | |
| 1.16 | $C_3H_7$-n | CH | — | |
| 1.17 | $C_3H_7$-n | N | — | m.p. 68.5–71° |
| 1.18 | $C_3H_7$-n | N | $ZnCl_2$ | |
| 1.19 | $C_3H_7$-n | N | HCl | |
| 1.20 | $C_4H_9$-n | N | — | |
| 1.21 | $C_4H_9$-n | CH | — | |
| 1.22 | $CH_2Cl$ | N | — | |
| 1.23 | $CH_2OH$ | N | — | m.p. 111–122° |
| 1.24 | 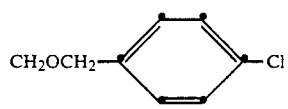 | N | — | viscous oil; $n_D^{26} = 1.5856$ A |

TABLE 1-continued

Compounds of the formula (XXI)

[Structure: diphenyl ether with dioxolane ring containing R10, connected via CH2-N to heterocycle with Y]

including isomeric forms:

| Compound | R10 | Y | Salt | Physical data (°C.) |
|---|---|---|---|---|
| 1.25 | CH₂OCH₂—(C₆H₄)—Cl | N | — | m.p. 83–85° B |
| 1.26 | CH₂O—(C₆H₄)—CH₃ | N | — | m.p. 107–109° A |
| 1.27 | CH₂O—(C₆H₄)—CH₃ | N | — | m.p. 90–94° B |
| 1.28 | CH₂OH | CH | — | m.p. 118–123° |
| 1.29 | CH₂OCH₃ | CH | — | |
| 1.30 | C₂H₅ | N | ½CuSO₄ | |
| 1.31 | CH₂OC₂H₅ | N | — | |
| 1.32 | CH₂OCH₃ | N | — | |
| 1.33 | CH₂OCH₂CH₂OCH₃ | N | — | |

TABLE 2

Compounds of the formula (XXII)

[Structure: diphenyl ether with dioxolane ring containing R11 and R12, connected via CH2-N to heterocycle with Y]

including the isomeric forms:

| Compound | R11 | R12 | Y | Salt | Physical data (°C.) |
|---|---|---|---|---|---|
| 2.1 | CH₃ | C₂H₅ | CH | — | |
| 2.2 | CH₃ | C₂H₅ | N | — | |
| 2.3 | CH₃ | C₂H₅ | CH | HNO₃ | |
| 2.4 | CH₃ | C₂H₅ | N | HNO₃ | |
| 2.5 | CH₃ | C₃H₇-n | CH | — | |
| 2.6 | CH₃ | C₃H₇-n | N | — | |
| 2.7 | CH₃ | C₃H₇-n | N | HNO₃ | |
| 2.8 | CH₃ | C₃H₇-n | N | Mn(NO₃)₂ | |
| 2.9 | CH₃ | CH₃ | CH | — | |
| 2.10 | CH₃ | CH₃ | CH | CuCl₂ | |
| 2.11 | CH₃ | C₂H₅ | CH | Mn(NO₃)₂ | |
| 2.12 | CH₃ | C₂H₅ | CH | CuCl₂ | |
| 2.13 | CH₃ | C₂H₅ | N | CuCl₂ | |
| 2.14 | CH₃ | C₂H₅ | N | ZnCl₂ | |
| 2.15 | CH₃ | C₂H₅ | N | Mn(NO₃)₂ | |
| 2.16 | CH₃ | C₂H₅ | N | FeCl₃ | |
| 2.17 | CH₃ | CH₃ | N | — | oil; $n_D^{23} = 1.5643$ |
| 2.18 | CH₃ | CH₃ | N | HNO₃ | |
| 2.19 | C₂H₅ | CH₃ | CH | MnCl₂ | |
| 2.20 | C₂H₅ | CH₃ | N | MnCl₂ | |
| 2.21 | C₂H₅ | CH₃ | CH | H₂SO₄ | |
| 2.22 | C₂H₅ | CH₃ | CH | ZnCl₂ | |
| 2.23 | C₂H₅ | C₂H₅ | CH | — | |
| 2.24 | C₂H₅ | C₂H₅ | CH | H₂SO₄ | |

TABLE 2-continued
Compounds of the formula

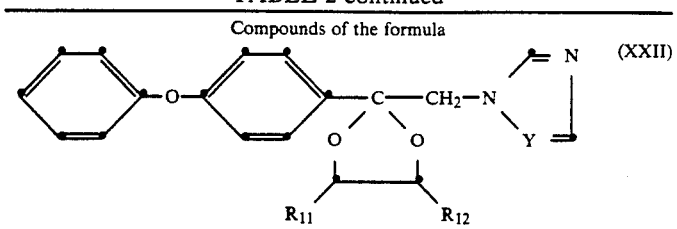

including the isomeric forms:

| Compound | $R_{11}$ | $R_{12}$ | Y | Salt | Physical data (°C.) |
|---|---|---|---|---|---|
| 2.25 | $C_2H_5$ | $C_2H_5$ | N | — | |
| 2.26 | $C_2H_5$ | $C_2H_5$ | N | $HNO_3$ | |
| 2.27 | $C_2H_5$ | $C_2H_5$ | N | HCl | |
| 2.28 | $C_2H_5$ | $C_3H_7$-n | N | — | |
| 2.29 | $C_2H_5$ | $C_3H_7$-i | N | — | |
| 2.30 | $C_2H_5$ | $C_3H_7$-n | CH | — | |
| 2.31 | $C_2H_5$ | $C_3H_7$-n | N | HCl | |
| 2.32 | $C_2H_5$ | $C_2H_5$ | N | $Mn(NO_3)_2$ | |
| 2.33 | $CH_3$ | $C_2H_5$ | N | $(COOH)_2$ | |
| 2.34 | $CH_3$ | $C_2H_5$ | CH | $(COOH)_2$ | |
| 2.35 | $CH_3$ | $C_3H_7$-i | N | — | |
| 2.36 | $CH_3$ | $C_3H_7$-i | N | $H_2SO_4$ | |
| 2.37 | $-(CH_2)_4-$ | | CH | — | |
| 2.38 | $-(CH_2)_4-$ | | CH | $HNO_3$ | |
| 2.39 | $-(CH_2)_4-$ | | N | — | |
| 2.40 | $-(CH_2)_4-$ | | N | $Mn(NO_3)_2$ | |
| 2.41 | $-(CH_2)_4-$ | | N | $(COOH)_2$ | |
| 2.42 | $-(CH_2)_4-$ | | N | $ZnCl_2$ | |
| 2.43 | $-(CH_2)_4-$ | | N | HCl | |
| 2.44 | $-(CH_2)_4-$ | | CH | $ZnCl_4$ | |

TABLE 3
Compounds of the formula

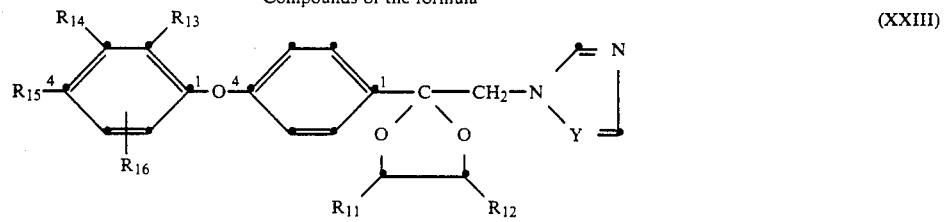

including the isomeric forms:

| Compound | $R_{11}$ | $R_{12}$ | $R_{13}$ | $R_{14}$ | $R_{15}$ | $R_{16}$ | Y | Salt | Physical data (°C.) |
|---|---|---|---|---|---|---|---|---|---|
| 3.1 | H | $C_2H_5$ | Cl | H | Cl | H | N | — | oil; $n_D^{23} = 1.5778$ |
| 3.2 | H | $C_2H_5$ | $CH_3$ | H | $CH_3$ | H | N | — | m.p. 74–76° |
| 3.3 | H | $C_2H_5$ | $CH_3$ | H | $CH_3$ | H | N | $HNO_3$ | |
| 3.4 | H | $C_2H_5$ | Cl | H | Cl | H | CH | — | |
| 3.5 | H | $C_2H_5$ | Cl | H | Cl | H | N | $CuCl_2$ | |
| 3.6 | H | $C_2H_5$ | H | H | Cl | H | N | — | m.p. 74–80° |
| 3.7 | H | $C_2H_5$ | H | H | Cl | H | CH | — | oil; $n_D^{25} = 1.5750$ |
| 3.8 | H | $C_2H_5$ | H | Cl | H | 5-Cl | N | — | m.p. 111.5–114° |
| 3.9 | H | $C_2H_5$ | H | Cl | H | 6-Cl | CH | — | |
| 3.10 | $CH_3$ | $CH_3$ | H | Cl | H | 5-Cl | N | $Mn(NO_3)_2$ | |
| 3.11 | H | $C_2H_5$ | H | Cl | H | H | N | — | m.p. 96–98° |
| 3.12 | H | $C_2H_5$ | H | Cl | H | H | CH | — | m.p. 69–71° |
| 3.13 | H | $CH_3$ | H | Br | H | H | N | — | |
| 3.14 | $CH_3$ | $CH_3$ | Cl | H | Cl | H | N | — | |
| 3.15 | $CH_3$ | $CH_3$ | Cl | H | Cl | H | CH | — | |
| 3.16 | H | $C_3H_7(n)$ | H | Cl | H | H | N | — | |
| 3.17 | H | $C_3H_7(n)$ | H | Cl | H | 5-Cl | N | — | |
| 3.18 | H | $C_3H_7(i)$ | H | Cl | H | 5-Cl | N | — | |
| 3.19 | H | $C_3H_7(i)$ | H | Cl | H | 5-Cl | CH | — | |
| 3.20 | H | $C_3H_7(i)$ | H | Cl | H | H | N | $HNO_3$ | |
| 3.21 | $C_2H_5$ | $C_2H_5$ | H | H | $CH_3$ | H | N | — | |
| 3.22 | $C_2H_5$ | $C_2H_5$ | $CH_3$ | H | $CH_3$ | H | N | — | |
| 3.23 | $CH_3$ | $CH_3$ | $CH_3$ | H | $CH_3$ | H | N | — | |
| 3.24 | H | $CH_3$ | H | $(CH=CH)_2$ | | H | N | — | |
| 3.25 | H | $CH_3$ | H | $(CH=CH)_2$ | | H | CH | — | |
| 3.26 | H | $C_2H_5$ | H | $(CH=CH)_2$ | | H | N | — | oil; $n_D^{23} = 1.6086$ |
| 3.27 | H | $C_2H_5$ | H | $(CH=CH)_2$ | | H | CH | — | |
| 3.28 | H | $C_2H_5$ | H | $(CH=CH)_2$ | | H | N | HCl | |

TABLE 3-continued

Compounds of the formula (XXIII)

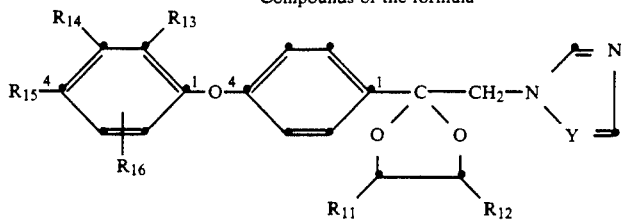

including the isomeric forms:

| Compound | $R_{11}$ | $R_{12}$ | $R_{13}$ | $R_{14}$ | $R_{15}$ | $R_{16}$ | Y | Salt | Physical data (°C.) |
|---|---|---|---|---|---|---|---|---|---|
| 3.29 | H | $C_2H_5$ | H | | $(CH=CH)_2$ | H | N | $(COOH)_2$ | |
| 3.30 | H | $C_2H_5$ | Cl | | $(CH=CH)_2$ | H | N | — | |
| 3.31 | $CH_3$ | $CH_3$ | $CH_3$ | | $(CH=CH)_2$ | H | N | — | |
| 3.32 | $CH_3$ | $CH_3$ | H | | $(CH=CH)_2$ | H | N | $CuCl_2$ | |
| 3.33 | H | $CH_3$ | | $(CH=CH)_2$ | H | | 2-Cl | N | — | |
| 3.34 | H | $C_2H_5$ | | $(CH=CH)_2$ | H | | 3-Cl | N | — | |
| 3.35 | H | $C_2H_5$ | | $(CH=CH)_2$ | H | H | N | — | |
| 3.36 | H | $C_2H_5$ | | $(CH=CH)_2$ | H | H | CH | — | |
| 3.37 | H | $C_2H_5$ | | $(CH=CH)_2$ | H | H | N | $Mn(NO_3)$ | |
| 3.38 | H | $C_2H_5$ | | $(CH=CH)_2$ | H | $2\text{-}CH_3$ | N | — | |
| 3.39 | $CH_3$ | $CH_3$ | | $(CH=CH)_2$ | H | H | N | — | |
| 3.40 | $CH_3$ | $CH_3$ | | $(CH=CH)_2$ | H | H | CH | — | |
| 3.41 | H | $C_3H_7\text{-}i$ | | $(CH=CH)_2$ | H | H | N | — | |
| 3.42 | H | $C_2H_5$ | | $(CH=CH)_2$ | H | $2\text{-}CH_3$ | CH | HCl | |
| 3.43 | $C_2H_5$ | $C_2H_5$ | | $(CH=CH)_2$ | H | H | N | — | |
| 3.44 | H | $C_2H_5$ | F | H | H | H | CH | — | |
| 3.45 | H | $C_2H_5$ | F | H | H | H | N | — | |
| 3.46 | H | $C_2H_5$ | H | F | H | H | CH | — | |
| 3.47 | H | $C_2H_5$ | H | F | H | H | N | — | |
| 3.48 | H | $CH_2OCH_3$ | F | H | H | H | CH | — | |
| 3.49 | H | $CH_2OCH_3$ | H | F | H | H | CH | — | |
| 3.50 | H | $CH_2OCH_3$ | H | F | H | H | N | — | |
| 3.51 | H | $C_2H_5$ | H | H | F | H | CH | — | m.p. 67–69° |
| 3.52 | H | $C_2H_5$ | H | H | F | H | N | — | m.p. 64–69° |
| 3.53 | H | $CH_2OH$ | Cl | H | H | H | CH | — | |
| 3.54 | H | $CH_2OH$ | H | H | F | H | CH | — | m.p. 101–103° |
| 3.55 | H | $CH_2OCH_3$ | H | H | F | H | N | — | m.p. 70–71° |
| 3.56 | H | $C_2H_5$ | Cl | H | H | H | CH | — | m.p. 65–67° |
| 3.57 | H | $CH_2OCH_3$ | Cl | H | H | H | CH | — | m.p. 95–106° |
| 3.58 | H | $CH_2OCH_3$ | Cl | H | H | H | N | — | m.p. 90–98° |
| 3.59 | H | $C_2H_5$ | Cl | H | H | H | N | — | m.p. 71–73° |
| 3.60 | H | $CH_3$ | H | Cl | H | H | CH | — | |
| 3.63 | H | $CH_2OH$ | H | Cl | H | H | CH | — | |
| 3.64 | H | $CH_2OC_2H_5$ | H | Cl | H | H | CH | — | |
| 3.65 | H | $CH_2OCH_3$ | H | Cl | H | H | N | — | |
| 3.66 | $CH_3$ | $CH_3$ | H | Cl | H | H | CH | — | |
| 3.67 | H | $C_3H_7\text{-}n$ | H | Cl | H | H | CH | — | |
| 3.68 | H | $CH_2OCH_3$ | H | Cl | H | H | CH | — | |
| 3.69 | H | $C_6H_{13}\text{-}n$ | H | H | Cl | H | CH | — | |
| 3.70 | $CH_3$ | $CH_3$ | H | H | Cl | H | CH | — | oil, $n_D^{26}$ 1.5713 |
| 3.71 | H | $C_6H_5$ | H | H | Cl | H | CH | — | |
| 3.72 | H | $CH_2OC_2H_5$ | H | H | Cl | H | CH | — | |
| 3.73 | H | $CH_2OH$ | H | H | Cl | H | CH | — | |
| 3.74 | H | H | H | H | Cl | H | CH | — | |
| 3.75 | H | $C_3H_7\text{-}n$ | H | H | Cl | H | CH | — | viscous mass, $n_D^{23.5}$ 1.5693 |
| 3.76 | H | $CH_3$ | H | H | Cl | H | CH | — | |
| 3.77 | H | $CH_2Cl$ | H | H | Cl | H | CH | — | |
| 3.78 | H | $CH_2OCH_3$ | H | H | Cl | H | CH | — | oil, $n_D^{28}$ 1.5745 |
| 3.79 | H | $CH_2OCH_2CH=CH_2$ | H | H | Cl | H | CH | — | |
| 3.80 | H | $CH_2OCH_2C\equiv CH$ | H | H | Cl | H | CH | — | |
| 3.81 | H | $CH_3$ | H | H | Cl | H | N | — | m.p. 81–84° |
| 3.82 | H | $C_2H_5$ | H | H | Cl | H | N | $HNO_3$ | |
| 3.83 | H | $CH_2OCH_3$ | H | H | Cl | H | N | — | m.p. 78–85° |
| 3.84 | H | $CH_2O(CH_2)_2OCH_3$ | H | H | Cl | H | CH | — | |
| 3.85 | $CH_3$ | $CH_3$ | H | H | Cl | H | N | — | m.p. 95–97° |
| 3.86 | H | $C_2H_5$ | H | H | Cl | H | N | $\frac{1}{2}CuSO_4\cdot H_2O$ | m.p. 85–90° |
| 3.87 | H | $C_3H_7\text{-}n$ | H | H | Cl | H | N | — | m.p. 78–81° |
| 3.88 | H | $CH_2OC_2H_5$ | H | H | Cl | H | N | — | |
| 3.89 | H | $CH_2OCH_2CH=CH_2$ | H | H | Cl | H | N | — | |
| 3.90 | H | $CH_2O(CH_2)_2OCH_3$ | H | H | Cl | H | N | — | |
| 3.91 | H | $CH_2OCH_3$ | Br | H | H | H | CH | — | |
| 3.92 | H | $CH_2OCH_2C\equiv CH$ | H | H | Cl | H | N | — | |
| 3.93 | H | $CH_2O(CH_2)_2OCH_3$ | H | H | Cl | H | N | $\frac{1}{2}CuSO_4$ | |
| 3.94 | H | $CH_2OCH_3$ | Br | H | H | H | N | — | |
| 3.95 | H | $C_2H_5$ | H | Br | H | H | CH | — | |

TABLE 3-continued

Compounds of the formula

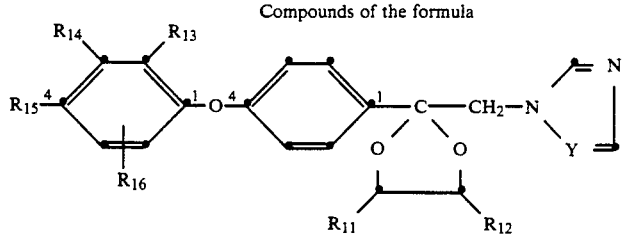

(XXIII)

including the isomeric forms:

| Compound | $R_{11}$ | $R_{12}$ | $R_{13}$ | $R_{14}$ | $R_{15}$ | $R_{16}$ | Y | Salt | Physical data (°C.) |
|---|---|---|---|---|---|---|---|---|---|
| 3.96 | H | CH$_2$OCH$_3$ | H | H | Br | H | N | — | |
| 3.97 | H | CH$_2$OCH$_3$ | H | H | J | H | CH | — | |
| 3.98 | H | C$_2$H$_5$ | H | H | J | H | N | — | |
| 3.99 | H | CH$_2$OCH$_3$ | H | Br | H | H | CH | — | |
| 3.100 | H | C$_2$H$_5$ | H | Br | H | H | N | — | |
| 3.101 | H | CH$_2$OH | H | H | Br | H | CH | — | |
| 3.102 | H | CH$_2$OCH$_3$ | H | H | Br | H | CH | — | |
| 3.103 | H | C$_2$H$_5$ | H | H | Br | H | N | — | m.p. 83–86° |
| 3.104 | H | C$_2$H$_5$ | CH$_3$ | H | H | H | N | — | |
| 3.105 | H | C$_2$H$_5$ | H | CH$_3$ | H | H | N | — | |
| 3.106 | H | CH$_2$OCH$_3$ | H | H | CH$_3$ | H | CH | — | |
| 3.107 | CH$_3$ | CH$_3$ | CH$_3$ | H | H | H | CH | — | |
| 3.108 | H | CH$_2$OCH$_3$ | H | CH$_3$ | H | H | CH | — | |
| 3.109 | H | CH$_2$OCH$_3$ | H | CH$_3$ | H | H | N | — | |
| 3.110 | H | CH$_2$OH | H | H | CH$_3$ | H | CH | — | |
| 3.111 | H | C$_2$H$_5$ | H | H | CH$_3$ | H | N | — | |
| 3.112 | H | CH$_2$OCH$_3$ | C$_2$H$_5$ | H | H | H | CH | — | |
| 3.113 | H | C$_2$H$_5$ | C$_2$H$_5$ | H | H | H | N | — | |
| 3.114 | H | CH$_2$OCH$_3$ | H | C$_2$H$_5$ | H | H | CH | — | |
| 3.115 | H | C$_3$H$_7$-n | H | C$_2$H$_5$ | H | H | N | — | |
| 3.116 | H | CH$_2$OH | H | H | C$_2$H$_5$ | H | CH | — | |
| 3.117 | H | C$_2$H$_5$ | H | C$_2$H$_5$ | H | H | CH | — | |
| 3.118 | H | CH$_2$OCH$_3$ | H | H | C$_2$H$_5$ | H | CH | — | |
| 3.119 | H | CH$_2$OCH$_3$ | H | H | C$_2$H$_5$ | H | N | — | |
| 3.120 | H | CH$_2$OCH$_3$ | C$_3$H$_7$-n | H | H | H | CH | — | |
| 3.121 | H | C$_2$H$_5$ | H | C$_3$H$_7$-i | H | H | CH | — | |
| 3.122 | H | CH$_2$OCH$_3$ | H | C$_3$H$_7$-i | H | H | CH | — | |
| 3.123 | H | CH$_2$OCH$_3$ | H | H | C$_3$H$_7$-i | H | CH | — | |
| 3.124 | H | CH$_2$OCH$_3$ | H | H | C$_3$H$_7$-i | H | N | — | |
| 3.125 | H | CH$_2$OCH$_3$ | C$_4$H$_9$-t | H | H | H | N | — | |
| 3.126 | H | C$_2$H$_5$ | H | C$_4$H$_9$-t | H | H | N | — | |
| 3.127 | H | C$_2$H$_5$ | H | H | C$_4$H$_9$-t | H | CH | — | $n_D^{22.5}$ = 1.5508 |
| 3.128 | H | CH$_2$OCH$_3$ | H | H | C$_2$H$_5$C(CH$_3$)$_2$ | H | CH | — | |
| 3.129 | H | C$_2$H$_5$ | H | H | C$_3$H$_7$-i | H | CH | — | |
| 3.130 | H | CH$_2$OCH$_3$ | H | C$_3$H$_7$-i | H | H | N | — | |
| 3.131 | H | C$_2$H$_5$ | H | H | C$_3$H$_7$-i | H | N | — | |
| 3.132 | H | CH$_2$OCH$_3$ | H | C$_4$H$_9$-t | H | H | N | — | |
| 3.133 | H | C$_2$H$_5$ | H | H | C$_4$H$_9$-t | H | N | — | $n_D^{22}$ = 1.5499 |
| 3.134 | H | CH$_2$OCH$_3$ | H | H | C$_4$H$_9$-t | H | CH | — | |
| 3.135 | H | CH$_2$OCH$_3$ | C$_2$H$_5$CH(CH$_3$)$_2$ | H | H | H | CH | — | |
| 3.136 | H | C$_2$H$_5$ | H | H | C$_2$H$_5$CH(CH$_3$)$_2$ | H | CH | — | |
| 3.137 | H | CH$_2$OCH$_3$ | OCH$_3$ | H | H | H | CH | — | |
| 3.138 | H | CH$_2$OCH$_3$ | OCH$_3$ | H | H | H | N | — | |
| 3.139 | H | CH$_2$OCH$_3$ | H | H | OC$_4$H$_9$-n | H | CH | — | |
| 3.140 | H | CH$_2$OCH$_3$ | H | H | OC$_7$H$_{15}$-n | H | CH | — | |
| 3.141 | H | C$_2$H$_5$ | OCH$_3$ | H | H | H | N | — | |
| 3.142 | CH$_3$ | CH$_3$ | H | H | OC$_4$H$_9$-n | H | N | — | |
| 3.143 | H | C$_2$H$_5$ | H | H | OC$_7$H$_{15}$-n | H | N | — | |
| 3.144 | H | C$_2$H$_5$ | NO$_2$ | H | H | H | CH | — | |
| 3.145 | H | CH$_2$OCH$_3$ | NO$_2$ | H | H | H | CH | — | |
| 3.146 | H | C$_3$H$_7$-n | NO$_2$ | H | H | H | N | — | |
| 3.147 | H | C$_2$H$_5$ | H | NO$_2$ | H | H | N | — | |
| 3.148 | H | CH$_2$OCH$_3$ | H | H | NO$_2$ | H | CH | — | |
| 3.149 | H | CH$_2$OCH$_3$ | CF$_3$ | H | H | H | CH | — | |
| 3.150 | H | C$_3$H$_7$-n | H | CF$_3$ | H | H | CH | — | |
| 3.151 | H | CH$_2$OCH$_3$ | H | NO$_2$ | H | H | CH | — | |
| 3.152 | H | C$_2$H$_5$ | H | H | NO$_2$ | H | CH | — | |
| 3.153 | H | C$_2$H$_5$ | H | H | NO$_2$ | H | N | — | |
| 3.154 | H | CH$_2$OCH$_3$ | H | CF$_3$ | H | H | CH | — | |
| 3.155 | H | C$_2$H$_5$ | H | CF$_3$ | H | H | CH | — | viscous mass |
| 3.156 | H | C$_2$H$_5$ | H | CF$_3$ | H | H | N | — | m.p. 80–83° |
| 3.157 | H | CH$_2$OCH$_3$ | H | CF$_3$ | H | H | N | — | |
| 3.158 | H | CH$_2$OCH$_3$ | H | H | CF$_3$ | H | CH | — | |
| 3.159 | H | CH$_2$OCH$_3$ | H | H | CF$_3$ | H | N | — | |
| 3.160 | H | C$_2$H$_5$ | H | H | CF$_3$ | H | CH | — | viscous mass |
| 3.161 | H | CH$_2$OCH$_3$ | Cl | H | Cl | H | CH | — | |
| 3.162 | H | C$_2$H$_5$ | Cl | H | H | 5-Cl | CH | — | $n_D^{23}$ = 1.5837 |

TABLE 3-continued

Compounds of the formula (XXIII)

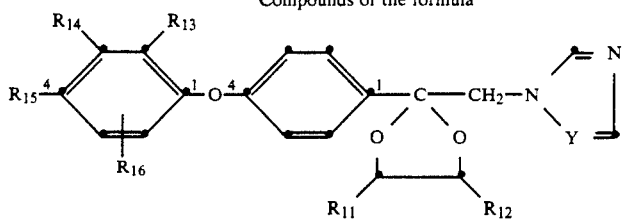

including the isomeric forms:

| Compound | $R_{11}$ | $R_{12}$ | $R_{13}$ | $R_{14}$ | $R_{15}$ | $R_{16}$ | Y | Salt | Physical data (°C.) |
|---|---|---|---|---|---|---|---|---|---|
| 3.163 | H | CH$_2$OCH$_3$ | Cl | H | H | 5-Cl | N | — | |
| 3.164 | H | C$_2$H$_5$ | Cl | H | Cl | H | CH | — | $n_D^{22}$ = 1.5779 |
| 3.165 | H | H | Cl | H | Cl | H | N | — | |
| 3.166 | H | CH$_2$OCH$_3$ | Cl | H | Cl | H | N | — | |
| 3.167 | H | CH$_2$OCH$_3$ | Cl | H | H | 5-Cl | CH | — | |
| 3.168 | H | C$_2$H$_5$ | Cl | H | H | 5-Cl | N | — | $n_D^{23}$ = 1.5788 |
| 3.169 | H | CH$_2$OCH$_3$ | Cl | H | H | 6-Cl | CH | — | |
| 3.170 | H | CH$_2$OCH$_3$ | Cl | H | H | 6-Cl | N | — | |
| 3.171 | H | C$_2$H$_5$ | H | Cl | Cl | H | CH | — | $n_D^{23}$ = 1.5835 |
| 3.172 | H | C$_2$H$_5$ | H | Cl | Cl | H | N | — | m.p. 90–97° |
| 3.173 | H | C$_2$H$_5$ | H | Cl | H | 5-Cl | CH | — | |
| 3.174 | H | C$_2$H$_5$ | Cl | H | H | 6-Cl | CH | — | viscous mass, $n_D^{28}$ 1.5808 |
| 3.175 | H | C$_2$H$_5$ | Cl | H | H | 6-Cl | N | — | |
| 3.176 | H | CH$_2$OCH$_3$ | H | Cl | Cl | H | CH | — | $n_D^{23}$ = 1.5836 |
| 3.177 | H | CH$_2$OCH$_3$ | H | Cl | Cl | H | N | — | m.p. 48–60° |
| 3.178 | H | CH$_3$ | H | Cl | H | 5-Cl | CH | — | |
| 3.179 | H | CH$_2$OCH$_3$ | H | Cl | H | 5-Cl | CH | — | |
| 3.180 | H | CH$_2$OCH$_3$ | H | Cl | H | 5-Cl | N | — | |
| 3.181 | H | CH$_2$OH | Br | H | Br | H | CH | — | |
| 3.182 | H | C$_2$H$_5$ | Br | H | Br | H | CH | — | |
| 3.183 | H | C$_2$H$_5$ | Br | H | Br | H | N | — | |
| 3.184 | H | C$_2$H$_5$ | Br | H | Cl | H | CH | — | |
| 3.185 | H | C$_2$H$_5$ | Br | H | Cl | H | N | — | |
| 3.186 | CH$_3$ | CH$_3$ | Br | H | Br | H | CH | — | |
| 3.187 | CH$_3$ | CH$_3$ | F | H | H | H | CH | — | |
| 3.188 | H | CH$_2$OCH$_3$ | Br | H | Br | H | N | — | |
| 3.189 | H | CH$_2$OCH$_3$ | Br | H | Cl | H | CH | — | |
| 3.190 | H | CH$_2$OCH$_3$ | Br | H | Cl | H | N | — | |
| 3.191 | H | CH$_2$OCH$_3$ | Cl | H | Br | H | CH | — | |
| 3.192 | H | CH$_2$OCH$_3$ | Cl | H | Br | H | N | — | |
| 3.193 | H | C$_2$H$_5$ | CH$_3$ | H | CH$_3$ | H | CH | — | m.p. 84–90° |
| 3.194 | H | C$_2$H$_5$ | Cl | H | Br | H | CH | — | |
| 3.195 | H | C$_2$H$_5$ | Cl | H | Br | H | N | — | |
| 3.196 | H | CH$_2$OCH$_3$ | CH$_3$ | H | CH$_3$ | H | CH | — | |
| 3.197 | H | CH$_2$OCH$_3$ | CH$_3$ | H | CH$_3$ | H | N | — | |
| 3.198 | H | CH$_2$OC$_2$H$_5$ | CH$_3$ | H | H | 5-CH$_3$ | N | — | |
| 3.199 | H | C$_2$H$_5$ | H | CH$_3$ | H | 5-CH$_3$ | CH | — | |
| 3.200 | H | CH$_2$OCH$_3$ | C$_4$H$_9$-t | H | CH$_3$ | H | CH | — | |
| 3.201 | H | C$_2$H$_5$ | C$_4$H$_9$-t | H | C$_4$H$_9$-t | H | N | — | |
| 3.202 | H | CH$_2$OCH$_3$ | C$_3$H$_7$-i | H | H | 5-CH$_3$ | CH | — | |
| 3.203 | H | CH$_2$O(CH$_2$)$_2$OCH$_3$ | NO$_2$ | H | NO$_2$ | H | CH | — | |
| 3.204 | H | CH$_2$OC$_2$H$_5$ | CH$_3$ | H | H | 5-CH$_3$ | CH | — | |
| 3.205 | H | C$_2$H$_5$ | H | CH$_3$ | H | 5-CH$_3$ | N | — | |
| 3.206 | H | CH$_2$OCH$_3$ | C$_4$H$_9$-t | H | CH$_3$ | H | N | — | |
| 3.207 | H | CH$_2$OCH$_3$ | C$_4$H$_9$-t | H | C$_4$H$_9$-t | H | CH | — | |
| 3.208 | H | CH$_2$OCH$_3$ | C$_3$H$_7$-i | H | H | 5-CH$_3$ | N | — | |
| 3.209 | H | CH$_2$OC$_2$H$_5$ | NO$_2$ | H | NO$_2$ | H | N | — | |
| 3.210 | H | CH$_2$OCH$_3$ | H | Cl | Cl | 6-Cl | CH | — | |
| 3.211 | H | CH$_2$OCH$_3$ | H | Cl | Cl | 6-Cl | N | — | |
| 3.212 | H | C$_2$H$_5$ | H | Cl | Cl | 6-Cl | CH | — | viscous mass |
| 3.213 | H | C$_2$H$_5$ | H | Cl | Cl | 6-Cl | N | — | oil; $n_D^{23}$ = 1.5863 |
| 3.214 | H | CH$_2$OCH$_3$ | Cl | H | Cl | 6-Cl | CH | — | |
| 3.215 | H | CH$_2$OCH$_3$ | H | Cl | Cl | 5-Cl | CH | — | |
| 3.216 | H | CH$_2$OCH$_3$ | H | Cl | Cl | 5-Cl | N | — | |
| 3.217 | CH$_3$ | CH$_3$ | Br | H | Br | 6-Br | N | — | |
| 3.218 | H | Br | Br | H | Br | 6-Br | N | — | |
| 3.219 | H | CH$_2$OCH$_3$ | CH$_3$ | CH$_3$ | H | 6-CH$_3$ | N | — | |
| 3.220 | H | C$_2$H$_5$ | CH$_3$ | H | Cl | H | CH | — | m.p. 94–96° |
| 3.221 | H | C$_2$H$_5$ | CH$_3$ | H | Cl | H | N | — | m.p. 78–80° |
| 3.222 | H | CH$_2$OCH$_3$ | Cl | H | Cl | 6-Cl | N | — | |
| 3.223 | H | CH$_2$OH | H | Cl | Cl | 5-Cl | CH | — | |
| 3.224 | H | CH$_2$OCH$_3$ | Br | H | Br | 6-Br | CH | — | |
| 3.225 | H | CH$_2$OCH$_3$ | CH$_3$ | CH$_3$ | H | 5-CH$_3$ | CH | — | |
| 3.226 | H | CH$_2$OCH$_3$ | CH$_3$ | H | Cl | H | CH | — | m.p. 92–106° |
| 3.227 | H | CH$_2$OCH$_3$ | CH$_3$ | H | Cl | H | N | — | m.p. 101–103° |

TABLE 3-continued

Compounds of the formula (XXIII)

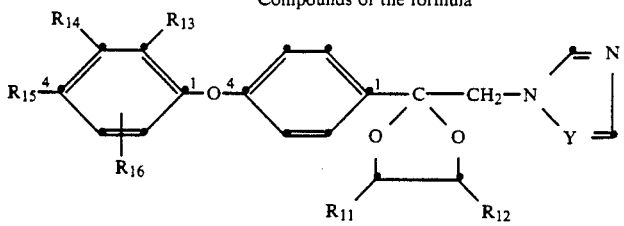

including the isomeric forms:

| Compound | $R_{11}$ | $R_{12}$ | $R_{13}$ | $R_{14}$ | $R_{15}$ | $R_{16}$ | Y | Salt | Physical data (°C.) |
|---|---|---|---|---|---|---|---|---|---|
| 3.228 | $CH_3$ | $CH_3$ | H | $CH_3$ | Cl | H | N | — | |
| 3.229 | H | $CH_2OCH_3$ | $C_4H_9$-t | H | Cl | H | N | — | |
| 3.230 | H | $CH_2OCH_3$ | H | $CH_3$ | H | 6-Cl | CH | — | |
| 3.231 | H | $CH_2OCH_3$ | H | $CH_3$ | Cl | H | CH | — | $n_D^{22.5}$ = 1.5752, oil |
| 3.232 | H | $C_2H_5$ | H | $CH_3$ | Cl | H | CH | — | $n_D^{22.5}$ = 1.5748, oil |
| 3.233 | H | $CH_2OCH_3$ | H | $CH_3$ | Cl | H | N | — | m.p. 88–93° |
| 3.234 | H | $C_2H_5$ | H | $CH_3$ | Cl | H | N | — | m.p. 72–75° |
| 3.235 | H | $C_3H_7$-n | $C_4H_9$-t | H | Cl | H | CH | — | |
| 3.236 | H | $CH_2OCH_3$ | $C_4H_9$-t | H | Cl | H | N | — | |
| 3.237 | H | $CH_2OCH_3$ | H | $CH_3$ | H | 6-Cl | N | — | |
| 3.238 | H | $CH_2OCH_3$ | Br | H | $CH_3$ | H | CH | — | |
| 3.239 | H | $CH_2OCH_3$ | Br | H | $CH_3$ | H | N | — | |
| 3.240 | H | $CH_2OCH_3$ | $CH_3$ | H | Br | H | CH | — | |
| 3.241 | H | $CH_2OCH_3$ | $CH_3$ | H | Br | H | N | — | |
| 3.242 | H | $CH_2OCH_2CH=CH_2$ | H | H | $OCH_3$ | H | 6-Cl | CH | — |
| 3.243 | H | $CH_2OCH_3$ | Cl | H | $NO_2$ | H | CH | — | |
| 3.244 | H | $CH_2OCH_3$ | Cl | H | $NO_2$ | H | N | — | |
| 3.245 | H | H | Br | H | $CH_3$ | H | N | — | |
| 3.246 | H | $CH_2Cl$ | Br | H | Br | H | CH | — | |
| 3.247 | H | $C_6H_5$ | $CH_3$ | H | Br | H | N | — | |
| 3.248 | H | $CH_2OCH_3$ | H | $OCH_3$ | H | 6-Cl | CH | — | |
| 3.249 | H | $CH_2OCH_3$ | H | $OCH_3$ | H | 6-Cl | N | — | |
| 3.250 | H | $CH_2OCH_2C≡CH$ | Cl | H | $NO_2$ | H | CH | — | |
| 3.251 | H | $CH_2OC_6H_5$ | $NO_2$ | H | Cl | H | CH | — | |
| 3.252 | H | $C_2H_5$ | $NO_2$ | H | Cl | H | CH | — | |
| 3.253 | H | $C_2H_5$ | $NO_2$ | H | Cl | H | N | — | |
| 3.254 | H | $C_2H_5$ | Cl | H | $CF_3$ | H | CH | — | |
| 3.255 | H | $CH_2OCH_3$ | Cl | H | $CF_3$ | H | CH | — | |
| 3.256 | H | $CH_2OCH_3$ | Cl | H | $CF_3$ | H | N | — | |
| 3.257 | H | $CH_2OCH_3$ | $NO_2$ | H | $CF_3$ | H | CH | — | |
| 3.258 | H | $CH_2OCH_3$ | $NO_2$ | H | Cl | H | CH | — | |
| 3.259 | H | $CH_2OCH_3$ | $NO_2$ | H | Cl | H | N | — | |
| 3.260 | H | $C_2H_5$ | H | H | $CF_3$ | H | N | — | m.p. 106–107° |
| 3.261 | H | $C_2H_5$ | H | H | $NO_2$ | H | CH | — | |
| 3.262 | H | $C_2H_5$ | H | H | $NO_2$ | H | N | — | |
| 3.263 | H | $C_2H_5$ | $NO_2$ | H | $CF_3$ | H | CH | — | m.p. 96–102° |
| 3.264 | $CH_3$ | $CH_3$ | $NO_2$ | H | $CF_3$ | H | N | — | |
| 3.265 | H | $CH_2OCH_3$ | $NO_2$ | H | $CF_3$ | H | N | — | |
| 3.266 | H | $CH_2OCH_3$ | $CF_3$ | H | $NO_2$ | H | CH | — | |
| 3.267 | H | $C_2H_5$ | H | $CH_3$ | Cl | 5-$CH_3$ | CH | — | m.p. 75–78° |
| 3.268 | H | $CH_2OCH_3$ | H | $CH_3$ | Cl | 5-$CH_3$ | CH | — | |
| 3.269 | H | $CH_2OCH_3$ | H | $CH_3$ | Cl | 5-$CH_3$ | N | — | |
| 3.270 | H | $C_2H_5$ | H | $CH_3$ | Br | 5-$CH_3$ | CH | — | |
| 3.271 | H | $C_2H_5$ | $NO_2$ | H | $CF_3$ | H | N | — | |
| 3.272 | H | $CH_2OCH_3$ | $CF_3$ | H | $NO_2$ | H | N | — | |
| 3.273 | H | $CH_2OC_6H_5$ | H | $CH_3$ | Cl | 5-$CH_3$ | CH | — | |
| 3.274 | H | $C_2H_5$ | H | $CH_3$ | Cl | 5-$CH_3$ | N | — | m.p. 64–73° |
| 3.275 | H | $CH_2OCH_3$ | H | $CH_3$ | Cl | 5-$CH_3$ | CH | — | |
| 3.276 | H | $C_2H_5$ | H | $CH_3$ | Br | 5-$CH_3$ | N | — | |
| 3.277 | H | $CH_2OCH_2C≡CH$ | H | $CH_3$ | Br | 5-$CH_3$ | N | — | |
| 3.278 | H | $C_2H_5$ | Cl | H | Cl | 5-$CH_3$ | N | — | |
| 3.279 | H | $C_2H_5$ | Cl | H | Cl | 6-$CH_3$ | CH | — | m.p. 70–74° |
| 3.280 | H | $CH_2OCH_3$ | Cl | H | Cl | 6-$CH_3$ | CH | — | |
| 3.281 | H | $CH_3$ | Cl | H | Cl | 6-$CH_3$ | N | — | |
| 3.282 | H | $C_2H_5$ | $CH_3$ | H | Br | 6-Cl | CH | — | |
| 3.283 | H | $CH_2OCH_3$ | H | $CH_3$ | Br | 5-$CH_3$ | N | — | |
| 3.284 | H | $C_2H_5$ | Cl | H | Cl | 5-$CH_3$ | CH | — | |
| 3.285 | H | $CH_2OC_6H_5$ | Cl | H | Cl | 5-$CH_3$ | N | — | |
| 3.286 | H | $CH_2OCH_3$ | Cl | H | Cl | 6-$CH_3$ | CH | — | |
| 3.287 | H | $C_2H_5$ | Cl | H | Cl | 6-$CH_3$ | N | — | m.p. 98–101° |
| 3.288 | H | $C_3H_7$-n | Cl | H | Cl | 6-$CH_3$ | N | — | |
| 3.289 | H | $CH_2OCH_3$ | $CH_3$ | H | Br | 6-Cl | CH | — | |
| 3.290 | H | $CH_2OCH_3$ | $CH_3$ | H | Br | 6-Cl | N | — | |
| 3.291 | H | $CH_2OCH_3$ | $CF_3$ | H | $NO_2$ | 6-$CF_3$ | CH | — | |
| 3.292 | H | $C_2H_5$ | $NO_2$ | H | $NO_2$ | 6-$CF_3$ | CH | — | m.p. 154–156° |
| 3.293 | H | $C_2H_5$ | $NO_2$ | H | $NO_2$ | 6-$CF_3$ | N | — | |
| 3.294 | H | $C_2H_5$ | $CH_3$ | H | Br | 6-Cl | N | — | |

TABLE 3-continued

Compounds of the formula (XXIII)

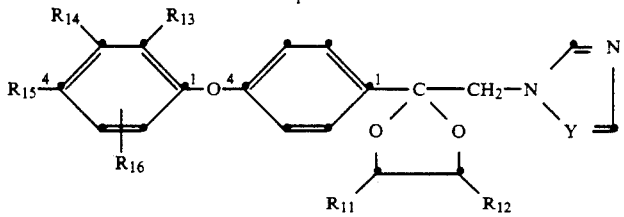

including the isomeric forms:

| Compound | $R_{11}$ | $R_{12}$ | $R_{13}$ | $R_{14}$ | $R_{15}$ | $R_{16}$ | Y | Salt | Physical data (°C.) |
|---|---|---|---|---|---|---|---|---|---|
| 3.295 | $CH_3$ | $CH_3$ | $CF_3$ | H | $NO_2$ | 6-$CF_3$ | CH | — | |
| 3.296 | H | $CH_3$ | $CF_3$ | H | $NO_2$ | 6-$CF_3$ | N | — | |
| 3.297 | H | $CH_2OCH_3$ | $CF_3$ | H | $NO_2$ | 6-$CF_3$ | N | — | |
| 3.298 | $CH_3$ | $CH_3$ | $NO_2$ | H | $NO_2$ | 6-$CF_3$ | CH | — | |
| 3.299 | H | H | $NO_2$ | H | $NO_2$ | 6-$CF_3$ | N | — | |
| 3.300 | H | $CH_2OCH_3$ | $NO_2$ | H | $NO_2$ | 6-$CF_3$ | N | — | |
| 3.301 | H | $CH_2OH$ | $(CH=CH)_2$ | | H | H | CH | — | |
| 3.302 | H | $CH_2OCH_3$ | $(CH=CH)_2$ | | H | H | CH | — | |
| 3.303 | H | $C_3H_7$-n | $(CH_2=CH_2)_2$ | | H | H | N | — | |
| 3.304 | H | $CH_2OCH_3$ | $(CH_2=CH_2)_2$ | | H | H | N | — | |
| 3.305 | H | $CH_2OH$ | $(CH_2=CH_2)_2$ | | Cl | H | CH | — | |
| 3.306 | H | $C_2H_5$ | $(CH_2=CH_2)_2$ | | Cl | H | N | — | |
| 3.307 | H | $CH_2OCH_3$ | $(CH_2=CH_2)_2$ | | Cl | H | CH | — | |
| 3.308 | H | $CH_2OCH_3$ | $(CH_2=CH_2)_2$ | | Cl | H | N | — | |
| 3.309 | H | $CH_2OCH_3$ | H | $(CH=CH)_2$ | | H | CH | — | |
| 3.310 | H | $CH_2OCH_3$ | H | $(CH=CH)_2$ | | H | N | — | |
| 3.311 | H | $C_2H_5$ | Cl | Cl | H | H | CH | — | oil; $n_D^{23} = 1.5832$ |
| 3.312 | $CH_3$ | $CH_3$ | Cl | Cl | H | H | CH | — | |
| 3.313 | H | $CH_2OCH_3$ | Cl | Cl | H | H | CH | — | |
| 3.314 | H | $C_2H_5$ | Cl | Cl | H | H | N | — | oil; $n_D^{23} = 1.5796$ |
| 3.315 | H | $CH_2OCH_3$ | Cl | Cl | H | H | N | — | |
| 3.316 | H | $CH_2OCH_3$ | $CH_3$ | $CH_3$ | H | H | CH | — | |
| 3.317 | H | $CH_2OCH_3$ | $CH_3$ | $CH_3$ | H | H | N | — | |
| 3.318 | —$(CH_2)_4$— | | Cl | H | Br | H | N | — | |
| 3.319 | H | $C_2H_5$ | $CH_3$ | $CH_3$ | H | H | CH | — | |
| 3.320 | H | $CH_2OCH_3$ | $CH_3$ | $CH_3$ | H | H | N | — | |
| 3.321 | H | $C_2H_5$ | Cl | Cl | Cl | H | CH | — | |
| 3.322 | H | $C_2H_5$ | Cl | Cl | Cl | H | N | — | |
| 3.323 | H | $CH_2OCH_3$ | Cl | Cl | Cl | H | CH | — | |
| 3.324 | H | $CH_2OCH_3$ | Cl | Cl | H | 6-Cl | CH | — | |
| 3.325 | H | $CH_2OCH_3$ | Cl | Cl | H | 6-Cl | N | — | |
| 3.326 | $CH_3$ | $CH_3$ | Cl | Cl | H | 6-Cl | CH | — | |
| 3.327 | H | $CH_2OCH_3$ | Cl | Cl | H | 6-Cl | N | — | |
| 3.328 | H | $CH_2OCH_3$ | H | $CH_3$ | H | 5-$CH_3$ | N | — | |
| 3.329 | H | $C_3H_7$-n | F | H | H | H | CH | — | |
| 3.330 | H | $CH_2OH$ | F | H | H | H | CH | — | |
| 3.331 | H | $CH_2OC_2H_5$ | F | H | H | H | CH | — | |
| 3.332 | H | $C_3H_7$-n | F | H | H | H | N | — | |
| 3.333 | H | $CH_2OCH_3$ | F | H | H | H | N | — | |
| 3.334 | H | $CH_3$ | H | F | H | H | CH | — | |
| 3.335 | $CH_3$ | $CH_3$ | H | F | H | H | CH | — | |
| 3.336 | H | $C_3H_7$-n | H | F | H | H | CH | — | |
| 3.337 | H | $CH_2OH$ | H | F | H | H | CH | — | |
| 3.338 | H | $C_3H_7$-n | H | F | H | H | N | — | |
| 3.339 | H | $CH_2OH$ | H | F | H | H | N | — | |
| 3.340 | H | $CH_2OCH_3$ | H | H | F | H | CH | — | m.p. 69-78° |
| 3.341 | H | H | H | H | F | H | CH | — | |
| 3.342 | H | $CH_3$ | H | H | F | H | CH | — | |
| 3.343 | $CH_3$ | $CH_3$ | H | H | F | H | CH | — | oil, $n_D^{23}$ 1.5723 |
| 3.344 | H | $C_3H_7$-n | H | H | F | H | CH | — | |
| 3.345 | H | H | H | H | F | H | N | — | |
| 3.346 | H | $CH_3$ | H | H | F | H | N | — | |
| 3.347 | $CH_3$ | $CH_3$ | H | H | F | H | N | — | |
| 3.348 | H | $CH_2OH$ | H | H | F | H | N | — | m.p. 93-97° |
| 3.349 | H | $CH_2OC_2H_5$ | H | H | F | H | N | — | |
| 3.350 | H | $CH_2OC_2H_5$ | Cl | H | H | H | CH | — | |
| 3.351 | H | $CH_3$ | Cl | H | H | H | N | — | |
| 3.352 | $CH_3$ | $CH_3$ | Cl | H | H | H | N | — | |
| 3.353 | H | $CH_3$ | Br | H | H | H | CH | — | |
| 3.354 | $CH_3$ | $CH_3$ | Br | H | H | H | CH | — | |
| 3.355 | H | $C_2H_5$ | Br | H | H | H | CH | — | |
| 3.356 | H | $CH_2OH$ | Br | H | H | H | CH | — | |
| 3.357 | H | $CH_3$ | Br | H | H | H | N | — | |
| 3.358 | $CH_3$ | $CH_3$ | Br | H | H | H | N | — | |
| 3.359 | H | $C_2H_5$ | Br | H | H | H | N | — | |
| 3.360 | H | $CH_2OH$ | Br | H | H | H | CH | — | |
| 3.361 | H | $CH_2OC_2H_5$ | Br | H | H | H | CH | — | |

TABLE 3-continued

Compounds of the formula (XXIII)

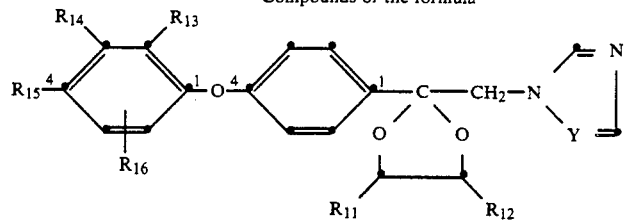

including the isomeric forms:

| Compound | $R_{11}$ | $R_{12}$ | $R_{13}$ | $R_{14}$ | $R_{15}$ | $R_{16}$ | Y | Salt | Physical data (°C.) |
|---|---|---|---|---|---|---|---|---|---|
| 3.362 | H | $CH_2OC_2H_5$ | Br | H | H | H | N | — | |
| 3.363 | H | H | H | Br | H | H | CH | — | |
| 3.364 | H | $CH_3$ | H | Br | H | H | CH | — | |
| 3.365 | H | $C_3H_7$-n | H | Br | H | H | CH | — | |
| 3.366 | H | $CH_2OH$ | H | Br | H | H | CH | — | |
| 3.367 | H | $CH_3$ | H | Br | H | H | N | — | |
| 3.368 | $CH_3$ | $CH_3$ | H | Br | H | H | N | — | |
| 3.369 | H | $C_3H_7$-n | H | Br | H | H | N | — | |
| 3.370 | H | $CH_2OH$ | H | Br | H | H | N | — | |
| 3.371 | H | $CH_2OCH_3$ | H | Br | H | H | N | — | |
| 3.372 | H | $C_2H_5$ | H | H | Br | H | CH | — | oil, $n_D^{23}$ 1.5856 |
| 3.373 | H | $C_3H_7$-n | H | H | Br | H | CH | — | oil, $n_D^{23}$ 1.5759 |
| 3.374 | H | $CH_2OC_2H_5$ | H | H | Br | H | CH | — | |
| 3.375 | $CH_3$ | $CH_3$ | H | H | Br | H | N | — | m.p. 104–106° |
| 3.376 | H | $C_3H_7$-n | H | H | Br | H | N | — | m.p. 81–83° |
| 3.377 | H | $CH_2OH$ | H | H | Br | H | N | — | |
| 3.378 | H | $CH_2OC_2H_5$ | H | H | Br | H | N | — | |
| 3.379 | H | $C_2H_5$ | H | H | I | H | CH | — | |
| 3.380 | H | $CH_2OH$ | H | H | I | H | CH | — | |
| 3.381 | H | $CH_2OCH_3$ | H | H | I | H | N | — | |
| 3.382 | H | $CH_2OH$ | H | H | I | H | N | — | |
| 3.383 | H | $C_2H_5$ | $CF_3$ | H | H | 5-$NO_2$ | CH | — | $n_D^{23}$ 1.5572 |
| 3.384 | H | $C_2H_5$ | Cl | H | $NO_2$ | H | CH | — | $n_D^{28}$ 1.5941 |
| 3.385 | H | $C_2H_5$ | H | H | $OCH_3$ | H | N | — | $n_D^{27}$ 1.5641 |
| 3.386 | H | $C_2H_5$ | Cl | H | $NO_2$ | H | N | — | $n_D^{28}$ 1.5942 |
| 3.387 | H | $C_2H_5$ | H | H | $CF_3$ | H | N | — | m.p. 106–107° |
| 3.388 | H | $C_2H_5$ | $C_2H_5$ | H | H | H | CH | $HNO_3$ | m.p. 99–101° |
| 3.389 | H | $CH_3$ | H | H | Br | H | N | — | m.p. 92–94° |

TABLE 4

Compounds of the formula (XXIV)

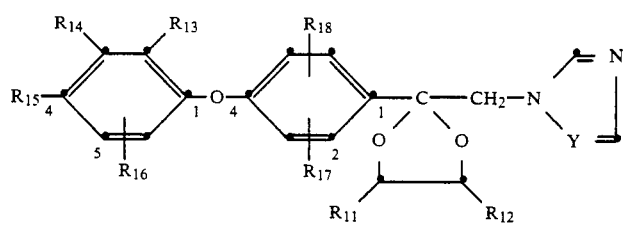

including the isomeric forms:

| Compound | $R_{11}$ | $R_{12}$ | $R_{13}$ | $R_{14}$ | $R_{15}$ | $R_{16}$ | Y | $R_{17}$ | $R_{18}$ | Salt | Physical data (°C.) |
|---|---|---|---|---|---|---|---|---|---|---|---|
| 4.1 | H | $C_2H_5$ | Cl | H | Cl | H | N | 3-$NO_2$ | H | — | |
| 4.2 | H | $C_2H_5$ | $CH_3$ | H | H | H | N | 2-$CH_3$ | H | — | m.p. 127–128° |
| 4.3 | H | $C_2H_5$ | $CH_3$ | H | $CH_3$ | H | N | 3-$CH_3$ | H | $HNO_3$ | |
| 4.4 | H | $C_2H_5$ | Cl | H | Cl | H | CH | 2-$CH_3$ | 6-$CH_3$ | — | |
| 4.5 | H | $C_2H_5$ | Cl | H | Cl | H | N | 2-Cl | H | $CuCl_2$ | |
| 4.6 | H | $C_2H_5$ | H | H | Cl | H | N | 3-$NO_2$ | H | — | |
| 4.7 | H | $C_2H_5$ | H | H | Cl | H | CH | 3-$NO_2$ | H | — | |
| 4.8 | H | $C_2H_5$ | H | Cl | H | 5-Cl | N | 2-Cl | H | — | |
| 4.9 | $C_2H_5$ | H | H | Cl | H | 6-Cl | CH | 2-$NO_2$ | H | — | |
| 4.10 | $CH_3$ | $CH_3$ | H | Cl | H | 6-Cl | N | 2-$NO_2$ | H | $Mn(NO_3)_2$ | |
| 4.11 | H | $C_2H_5$ | Cl | H | H | H | N | 2-Cl | H | — | |
| 4.12 | H | $C_2H_5$ | Cl | H | H | H | CH | 2-Br | H | — | |
| 4.13 | H | $CH_3$ | H | Br | H | H | N | 2-$CH_3$ | H | — | |
| 4.14 | $CH_3$ | $CH_3$ | Cl | H | Cl | H | N | 2-Cl | 6-Cl | — | |
| 4.15 | H | $CH_3$ | H | H | H | H | CH | 2-$CH_3$ | H | — | resin, $n_D^{50}$ 1.5581 |
| 4.16 | H | $C_3H_7$-n | Cl | H | H | H | N | 2-Cl | H | — | |
| 4.17 | H | $C_3H_7$-n | H | Cl | H | 6-Cl | N | 2-Cl | H | — | |
| 4.18 | H | $C_3H_7$-i | H | Cl | H | 6-Cl | N | 2-$OCH_3$ | H | — | |

TABLE 4-continued

Compounds of the formula

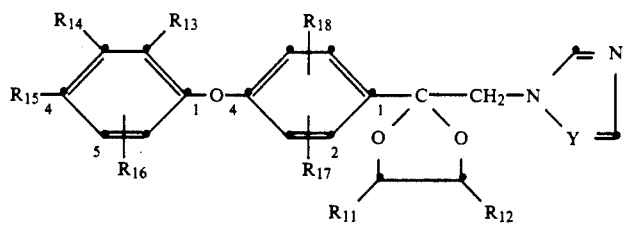
(XXIV)

including the isomeric forms:

| Compound | R11 | R12 | R13 | R14 | R15 | R16 | Y | R17 | R18 | Salt | Physical data (°C.) |
|---|---|---|---|---|---|---|---|---|---|---|---|
| 4.19 | H | C3H7-i | H | Cl | H | 5-Cl | CH | 2-OCH3 | 6-OCH3 | — | |
| 4.20 | H | C3H7-i | H | Cl | H | H | N | 2-Cl | H | HNO3 | |
| 4.21 | C2H5 | C2H5 | H | H | CH3 | H | N | 2-Cl | H | — | |
| 4.22 | C2H5 | C2H5 | CH3 | H | CH3 | H | N | 2-Cl | H | — | |
| 4.23 | CH3 | CH3 | H | F | H | H | N | 2-CH3 | H | — | brownish yellow resin, $n_D^{50}$ 1.5472 |
| 4.24 | H | CH3 | (CH=CH)2 | | H | H | N | 2-Cl | H | — | |
| 4.25 | H | C2H5 | (CH=CH)2 | | H | H | N | 2-Cl | 6-Cl | — | |
| 4.26 | H | CH3 | (CH=CH)2 | | H | H | CH | 2-NO2 | H | — | |
| 4.27 | H | C2H5 | (CH=CH)2 | | H | H | N | 2-Cl | H | — | |
| 4.28 | H | C3H7-i | (CH=CH)2 | | H | H | N | 2-Cl | H | — | |
| 4.29 | CH3 | CH3 | (CH=CH)2 | | H | H | N | 3-Cl | H | — | |
| 4.30 | CH3 | CH3 | (CH=CH)2 | | H | H | N | 2-Cl | H | — | |
| 4.31 | CH3 | CH3 | (CH=CH)2 | | H | 2-Cl | N | 2-Br | H | — | |
| 4.32 | H | C2H5 | (CH=CH)2 | | H | H | N | 2-Cl | H | HCl | |
| 4.33 | H | CH3 | (CH=CH)2 | | CH3 | H | N | 3-Cl | H | — | |
| 4.34 | H | CH3 | (CH=CH)2 | | H | 2-CH3 | N | H | H | HCl | |
| 4.35 | H | CH3 | (CH=CH)2 | | H | H | N | H | H | — | |
| 4.36 | H | CH3 | (CH=CH)2 | | H | H | CH | H | H | — | |
| 4.37 | H | CH3 | H | (CH=CH)2 | | H | N | 3-NO2 | H | — | |
| 4.38 | H | CH3 | H | (CH=CH)2 | | H | CH | 3-NO2 | H | — | |
| 4.39 | H | CH3 | H | (CH=CH)2 | | H | N | H | H | CuCl2 | |
| 4.40 | H | CH3 | Cl | (CH=CH)2 | | H | N | 2-Cl | H | — | |
| 4.41 | CH3 | CH3 | Cl | (CH=CH)2 | | H | N | 2-Cl | H | — | |
| 4.42 | H | C2H5 | Cl | (CH=CH)2 | | H | N | 3-Cl | H | — | |
| 4.43 | H | C3H7-i | CH3 | (CH=CH)2 | | H | N | H | H | — | |
| 4.44 | H | CH3 | CH3 | (CH=CH)2 | | H | N | 2-Cl | 6-Cl | — | |
| 4.45 | H | CH3 | Cl | (CH=CH)2 | | 3-Cl | N | 2-Cl | H | — | |
| 4.46 | H | CH3 | CH3 | (CH=CH)2 | | 3-CH3 | N | H | H | — | |
| 4.47 | H | CH3 | CH3 | (CH=CH)2 | | H | N | 2-Cl | H | — | |
| 4.48 | CH3 | H | CH3 | H | H | H | N | 2-CH3 | H | — | dark yellow resin |
| 4.49 | CH3 | CH3 | CH3 | H | OCH3 | H | N | 2-CH3 | H | — | |
| 4.50 | CH3 | H | H | H | OCH3 | H | N | 2-CH3 | H | — | resin, $n_D^{50}$ 1.5628 |
| 4.51 | C3H7-n | H | CH3 | H | H | H | N | 2-CH3 | H | — | |
| 4.52 | C3H7-n | H | CH3 | H | OCH3 | H | N | 2-CH3 | H | — | |
| 4.53 | C2H5 | H | CH3 | H | OCH3 | H | N | 2-CH3 | H | — | |
| 4.54 | H | CH2OCH3 | F | H | H | H | CH | 2-Cl | H | — | |
| 4.55 | H | C2H5 | F | H | H | H | N | 2-CH3 | H | — | resin |
| 4.56 | H | CH2OCH3 | H | F | H | H | CH | 2-Cl | H | — | |
| 4.57 | H | C2H5 | H | H | F | H | N | 2-CH3 | H | — | light brown resin |
| 4.58 | H | C2H5 | H | F | H | H | N | 2-Cl | H | — | |
| 4.59 | H | C2H5 | H | H | F | H | CH | 2-CH3 | H | — | brown resin, $n_D^{50}$ 1.5450 |
| 4.60 | H | C2H5 | H | H | F | H | CH | 2-Cl | H | — | |
| 4.61 | H | CH2OCH3 | Cl | H | H | H | CH | 2-Cl | H | — | |
| 4.62 | H | CH2OCH3 | Cl | H | H | H | N | 2-Cl | H | — | |
| 4.63 | H | CH2OH | H | Cl | H | H | CH | 2-Cl | H | — | |
| 4.64 | H | C2H5 | H | H | Cl | H | CH | 2-CH3 | H | — | resin, $n_D^{22}$ 1.5735 |
| 4.65 | H | CH3 | H | H | F | H | N | 2-CH3 | H | — | viscous oil |
| 4.66 | H | CH3 | H | H | F | H | CH | 2-CH3 | H | — | resin, $n_D^{50}$ 1.5493 |
| 4.67 | H | CH2OCH3 | H | H | Cl | H | N | 2-Cl | H | — | |
| 4.68 | H | C2H5 | H | Br | H | H | CH | 2-CH3 | H | — | |
| 4.69 | H | C2H5 | F | H | H | H | CH | 2-CH3 | H | — | |
| 4.70 | H | CH3 | H | H | F | H | CH | 2-CH3 | H | — | light brown resin |
| 4.71 | H | CH2OCH3 | Br | H | H | H | N | 2-Cl | H | — | |
| 4.72 | H | CH2OCH3 | H | Br | H | H | CH | 2-Cl | H | — | |
| 4.73 | H | CH2OCH3 | H | H | Br | H | CH | 2-Cl | H | — | |
| 4.74 | H | C2H5 | H | H | Br | H | N | 2-Cl | H | — | |
| 4.75 | H | CH2OCH3 | H | H | H | H | CH | 2-Cl | H | — | |
| 4.76 | H | CH2OCH3 | H | H | | H | N | 2-Cl | H | — | |
| 4.77 | H | C3H7-n | CH3 | H | H | H | N | 2-CH3 | H | HNO3 | m.p. 105-110° |
| 4.78 | H | CH3 | CH3 | H | H | H | N | 2-CH3 | H | HNO3 | m.p. 92-95° B |
| 4.79 | H | C2H7-n | H | CH3 | H | H | CH | 2-Cl | H | — | |
| 4.80 | H | CH2OCH3 | CH3 | H | H | H | CH | 2-Cl | H | — | |
| 4.81 | H | CH3 | CH3 | H | H | H | N | 2-CH3 | H | HNO3 | m.p. 129-134° A |
| 4.82 | H | CH2OCH3 | H | H | CH3 | H | N | 2-Cl | H | — | |

TABLE 4-continued

Compounds of the formula

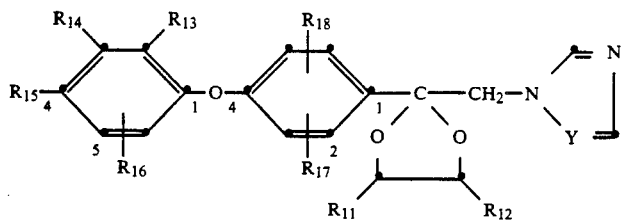

(XXIV)

including the isomeric forms:

| Compound | $R_{11}$ | $R_{12}$ | $R_{13}$ | $R_{14}$ | $R_{15}$ | $R_{16}$ | Y | $R_{17}$ | $R_{18}$ | Salt | Physical data (°C.) |
|---|---|---|---|---|---|---|---|---|---|---|---|
| 4.83 | H | $CH_2OCH_3$ | H | H | $CH_3$ | H | CH | 2-$CH_3$ | H | — | |
| 4.84 | H | $C_2H_5$ | H | H | $C_2H_5$ | H | N | 2-Cl | H | — | |
| 4.85 | H | $CH_2OCH_3$ | $C_3H_7$-i | H | H | H | CH | H | H | — | |
| 4.86 | H | $CH_2OCH_3$ | $C_3H_7$-i | H | H | H | CH | 2-$NO_2$ | H | — | |
| 4.87 | H | $CH_2OCH_3$ | H | $C_2H_5$ | H | H | CH | 3-$CH_3$ | H | — | |
| 4.88 | H | $CH_2OCH_3$ | H | $C_2H_5$ | H | H | N | 2-Cl | H | — | |
| 4.89 | $CH_3$ | $CH_3$ | H | H | $OCH_3$ | H | N | 2-$CH_3$ | H | — | resin B, m.p. 48–58° |
| 4.90 | H | $C_3H_7$-n | H | H | $OCH_3$ | H | N | 2-$CH_3$ | H | — | oil |
| 4.91 | H | $C_3H_7$-n | H | H | $OCH_3$ | H | N | 2-$CH_3$ | H | — | oil B |
| 4.92 | $CH_3$ | $CH_3$ | H | H | $OCH_3$ | H | N | 2-$CH_3$ | H | — | resin A |
| 4.93 | H | $C_2H_5$ | H | H | $OCH_3$ | H | N | 2-$CH_3$ | H | — | resin, $n_D^{50}$ 1.5579 |
| 4.94 | H | $C_3H_7$-n | H | H | $OCH_3$ | H | N | 2-$CH_3$ | H | — | oil A, $n_D^{50}$ 1.5511 |
| 4.95 | H | $CH_2OC_2H_5$ | $NO_2$ | H | H | H | CH | 2-Br | H | — | |
| 4.96 | H | $CH_2OCH_3$ | H | N | $NO_2$ | H | CH | 2-Cl | H | — | |
| 4.97 | H | $CH_2OH$ | H | $CF_3$ | H | H | CH | 3-$CH_3$ | H | — | |
| 4.98 | H | $CH_2OCH_3$ | H | H | $CF_3$ | H | CH | 2-Cl | H | — | |
| 4.99 | H | $CH_2OCH_3$ | H | Cl | H | H | CH | 2-Cl | H | — | |
| 4.100 | H | $CH_2OCH_3$ | Br | H | Br | H | CH | 2-Cl | H | — | |
| 4.101 | H | $CH_2OCH_3$ | Cl | H | Cl | H | CH | 2-Cl | H | — | |
| 4.102 | $CH_2OH$ | H | (CH=CH)$_2$ | | H | H | CH | 2-Cl | H | — | |
| 4.103 | $C_2H_5$ | H | $CH_3$ | H | Cl | H | CH | 2-$OCH_3$ | 6-$OCH_3$ | — | |
| 4.104 | $C_2H_5$ | H | (CH=CH)$_2$ | | H | H | CH | 2-Cl | H | — | |
| 4.105 | $CH_2OCH_3$ | H | (CH=CH)$_2$ | | H | H | CH | 2-Cl | H | — | |
| 4.106 | $CH_2OCH_3$ | H | (CH=CH)$_2$ | | H | H | N | H | H | — | |
| 4.107 | $C_2H_5$ | H | H | (CH=CH)$_2$ | | H | CH | 2-Cl | H | — | |
| 4.108 | $C_2H_5$ | H | H | (CH=CH)$_2$ | | H | N | 2-Cl | H | — | |
| 4.109 | $C_2H_5$ | H | (CH=CH)$_2$ | | Cl | H | CH | 2-Cl | H | — | |
| 4.110 | $C_2H_5$ | H | (CH=CH)$_2$ | | Cl | H | N | 2-Cl | H | — | |
| 4.111 | (CH$_2$)$_4$ | | H | H | Cl | H | CH | H | H | — | |
| 4.112 | $CH_2OCH_3$ | H | Cl | Cl | H | H | CH | 2-Cl | H | — | |
| 4.113 | $CH_3$ | H | H | H | Cl | H | N | 2-$CH_3$ | H | — | resin, $n_D^{50}$ 1.5600 |
| 4.114 | $C_2H_5$ | H | H | H | Cl | H | N | 2-$OCH_3$ | 6-$OCH_3$ | — | |
| 4.115 | $C_2H_5$ | H | H | H | Cl | H | CH | 2-$OCH_3$ | 6-$OCH_3$ | — | |
| 4.116 | $C_2H_5$ | H | H | H | Cl | H | N | 2-$CH_3$ | H | — | resin, $n_D^{22}$ 1.5718 |
| 4.117 | $CH_3$ | $CH_3$ | H | H | F | H | N | 2-$CH_3$ | H | — | |
| 4.118 | $CH_3$ | $CH_3$ | H | H | F | H | CH | 2-$CH_3$ | H | — | |
| 4.119 | $CH_3$ | $C_2H_5$ | H | H | F | H | N | 2-$CH_3$ | H | — | |
| 4.120 | $CH_3$ | $C_2H_5$ | H | H | F | H | CH | 2-$CH_3$ | H | — | |
| 4.121 | H | H | H | H | F | H | N | 2-$CH_3$ | H | — | |
| 4.122 | H | H | H | H | F | H | CH | 2-$CH_3$ | H | — | |
| 4.123 | H | —$C_3H_7$-n | H | H | F | H | N | 2-$CH_3$ | H | — | resin |
| 4.124 | H | —$C_3H_7$-n | H | H | F | H | CH | 2-$CH_3$ | H | — | resin |
| 4.125 | H | $CH_2OCH_3$ | H | H | F | H | N | 2-$CH_3$ | H | — | |
| 4.126 | H | $CH_2OCH_3$ | H | H | F | H | CH | 2-$CH_3$ | H | — | |
| 4.127 | H | H | H | H | Cl | H | N | 2-$CH_3$ | H | — | |
| 4.128 | H | H | H | H | Cl | H | CH | 2-$CH_3$ | H | — | highly viscous oil |
| 4.129 | H | $CH_3$ | H | H | Cl | H | N | 3-$CH_3$ | H | — | |
| 4.130 | H | $C_2H_5$ | H | H | Cl | H | N | 3-$CH_3$ | H | — | |
| 4.131 | H | H | H | H | Cl | H | N | 3-$CH_3$ | H | — | |
| 4.132 | H | $CH_3$ | H | H | Cl | H | CH | 3-$CH_3$ | H | — | |
| 4.133 | H | $C_2H_5$ | H | H | Cl | H | CH | 3-$CH_3$ | H | — | |
| 4.134 | H | $C_3H_7$-n | H | H | Cl | H | CH | 3-$CH_3$ | H | — | |
| 4.135 | H | $CH_2OCH_3$ | H | H | Cl | H | CH | 3-$CH_3$ | H | — | |
| 4.136 | $CH_3$ | $CH_3$ | H | F | H | H | CH | 2-$CH_3$ | H | $HNO_3$ | m.p. 131–140° |
| 4.137 | H | $C_2H_5$ | H | H | Cl | H | N | 2-Cl | H | — | $n_D^{22}$ 1.5631 |
| 4.138 | H | $C_2H_5$ | H | H | Cl | H | CH | 2-$CH_3$ | H | $HNO_3$ | m.p. 124–126° |
| 4.139 | H | $CH_3$ | F | H | H | H | N | 2-$CH_3$ | H | — | $n_D^{22}$ 1.5587 |
| 4.140 | H | $C_2H_5$ | H | H | Cl | H | N | 2-$CH_3$ | H | $HNO_3$ | m.p. 140–141° |
| 4.141 | H | H | $OCH_3$ | H | H | H | N | 2-Cl | H | — | $n_D^{22}$ 1.5762 |
| 4.142 | H | H | $OCH_3$ | H | H | H | CH | 2-Cl | H | — | $n_D^{22}$ 1.5830 |
| 4.143 | H | $C_2H_5$ | H | F | H | H | CH | 2-$CH_3$ | H | HBr | m.p. 175–177° |
| 4.144 | H | $CH_3$ | H | H | Cl | H | CH | 2-$CH_3$ | H | HBr | m.p. 180–184° |
| 4.145 | $CH_3$ | $CH_3$ | H | F | H | H | CH | 2-$CH_3$ | H | — | oil |
| 4.146 | $CH_3$ | $CH_3$ | H | H | Cl | H | N | 2-$CH_3$ | H | — | viscous oil |
| 4.147 | H | $C_2H_5$ | H | H | F | H | CH | 2-$OCH_3$ | H | — | $n_D^{20,5}$ 1.5570 |
| 4.148 | H | $C_2H_5$ | H | H | Cl | H | N | 3-Cl | H | — | $n_D^{21}$ 1.5793 |

TABLE 4-continued
Compounds of the formula

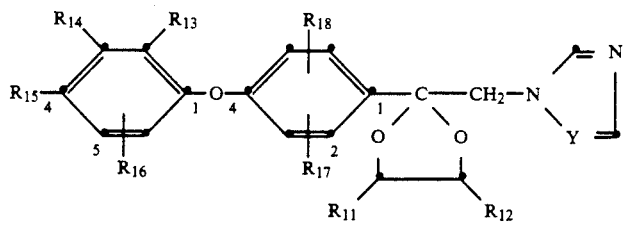

(XXIV)

including the isomeric forms:

| Compound | $R_{11}$ | $R_{12}$ | $R_{13}$ | $R_{14}$ | $R_{15}$ | $R_{16}$ | Y | $R_{17}$ | $R_{18}$ | Salt | Physical data (°C.) |
|---|---|---|---|---|---|---|---|---|---|---|---|
| 4.149 | H | $C_2H_5$ | H | H | Cl | H | CH | 3-Cl | H | — | $n_D^{22}$ 1.5832 |
| 4.150 | H | $C_2H_5$ | H | H | H | 5-Cl | N | 3-Cl | H | — | $n_D^{22}$ 1.5787 |
| 4.151 | H | $C_2H_5$ | H | H | H | 5-Cl | CH | 3-Cl | H | — | $n_D^{22}$ 1.5827 |
| 4.152 | H | $C_2H_5$ | H | Cl | H | H | CH | 3-Cl | H | — | $n_D^{22}$ 1.5827 |
| 4.153 | H | $C_2H_5$ | H | H | Cl | H | N | 2-Cl | H | $HNO_3$ | m.p. 129–130° |
| 4.154 | H | $C_2H_5$ | H | H | Cl | H | N | 2-$C_2H_5$ | H | — | $n_D^{24,5}$ 1.5620 |
| 4.155 | H | $C_2H_5$ | H | H | Cl | H | CH | 2-$C_2H_5$ | H | — | $n_D^{24,5}$ 1.5683 |
| 4.156 | H | $C_3H_7$-n | H | H | Cl | H | CH | 2-$CH_3$ | H | — | resin |
| 4.157 | H | $CH_2OCH_3$ | H | H | Cl | H | N | 2-$CH_3$ | H | — | visk. Oel |
| 4.158 | H | $C_2H_5$ | H | H | Cl | H | N | 2-$CH_3$ | H | — | resin, $n_D^{27}$ 1.5590 |
| 4.159 | H | $CH_2OCH_3$ | H | H | Cl | H | CH | 2-$CH_3$ | H | — | oil |
| 4.160 | H | $C_2H_5$ | H | H | Cl | H | CH | 2-$CH_3$ | 5-$C_3H_7$-i | — | resin, $n_D^{27}$ 1.5628 |
| 4.161 | H | $C_2H_5$ | H | H | Cl | H | N | 2-$CH_3$ | 5-$CH_3$ | — | m.p. 102–104° |
| 4.162 | H | $CH_3$ | H | H | Cl | H | N | 2-$CH_3$ | 5-$C_3H_7$-i | — | resin, $n_D^{25}$ 1.5646 |
| 4.163 | $CH_3$ | $CH_3$ | H | H | Cl | H | N | 2-$CH_3$ | 5-$C_3H_7$-i | — | m.p. 104–106° |

TABLE 5
Compounds of the formula

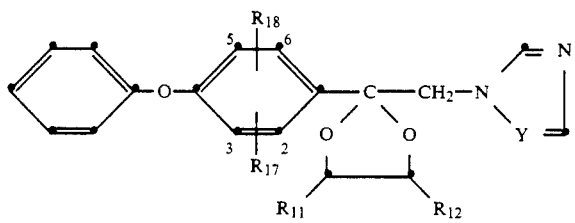

including the isomeric forms:

| Compound | $R_{11}$ | $R_{12}$ | $R_{17}$ | $R_{18}$ | Y | Salt | Physical data (°C.) |
|---|---|---|---|---|---|---|---|
| 5.1 | $CH_3$ | $C_2H_5$ | 2-Cl | H | CH | — | |
| 5.2 | $CH_3$ | $C_2H_5$ | 2-Cl | H | N | — | |
| 5.3 | $CH_3$ | $C_2H_5$ | 2-Cl | 6-Cl | CH | $HNO_3$ | |
| 5.4 | $CH_3$ | $C_2H_5$ | 2-$CH_3$ | H | N | $HNO_3$ | |
| 5.5 | $CH_3$ | $C_3H_7$-n | 2-Cl | H | CH | — | |
| 5.6 | $CH_3$ | $C_3H_7$-n | 2-Cl | H | N | — | |
| 5.7 | $CH_3$ | $C_3H_7$-n | 3-Cl | H | N | $HNO_3$ | |
| 5.8 | $CH_3$ | $C_3H_7$-n | 3-Cl | 6-Cl | N | $Mn(NO_3)_2$ | |
| 5.9 | $CH_3$ | $CH_3$ | 2-Cl | H | CH | — | |
| 5.10 | $CH_3$ | $CH_3$ | 2-Cl | 6-Cl | CH | $CuCl_2$ | |
| 5.11 | $CH_3$ | $C_2H_5$ | 2-Cl | H | CH | $Mn(NO_3)_2$ | |
| 5.12 | $CH_3$ | $C_2H_5$ | 2-$CH_3$ | 6-$CH_3$ | CH | $CuCl_2$ | |
| 5.13 | $CH_3$ | $CH_3$ | 2-$CH_3$ | H | N | $HNO_3$ | m.p. 158–160° |
| 5.14 | $CH_3$ | $CH_3$ | 2-$CH_3$ | H | N | HBr | m.p. 192–204° |
| 5.15 | $CH_3$ | $C_2H_5$ | 2-$CH_3$ | H | N | $Mn(NO_3)_2$ | |
| 5.16 | $CH_3$ | $C_2H_5$ | 2-$NO_2$ | H | N | $FeCl_3$ | |
| 5.17 | $CH_3$ | $CH_3$ | 2-Cl | H | N | — | |
| 5.18 | $CH_3$ | $CH_3$ | 2-Cl | 5-Cl | N | $HNO_3$ | |
| 5.19 | $C_2H_5$ | $CH_3$ | 3-Cl | H | CH | $MnCl_2$ | |
| 5.20 | $C_2H_5$ | $CH_3$ | 2-$CH_3$ | H | N | $MnCl_2$ | |
| 5.21 | $C_2H_5$ | $CH_3$ | 2-$CH_3$ | H | N | $CuCl_2$ | |
| 5.22 | $C_2H_5$ | $CH_3$ | 2-Cl | 5-Cl | N | $ZnCl_2$ | |
| 5.23 | $C_2H_5$ | $C_2H_5$ | 2-Br | H | CH | — | |
| 5.24 | H | $C_2H_5$ | 2-$OCH_3$ | 6-$OCH_3$ | CH | — | |
| 5.25 | H | H | 2-Cl | H | N | — | |
| 5.26 | H | H | 2-Cl | H | CH | — | |
| 5.27 | H | H | 2-Cl | 6-Cl | CH | — | |
| 5.28 | H | H | 2-Cl | H | N | $Mn(NO_3)_2$ | |
| 5.29 | H | H | 2-Cl | 6-Cl | N | — | |
| 5.30 | H | $CH_3$ | 2-Cl | H | N | — | |

TABLE 5-continued

Compounds of the formula

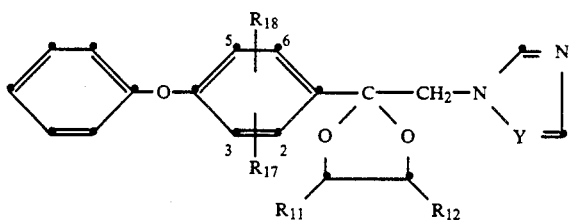

including the isomeric forms:

| Compound | $R_{11}$ | $R_{12}$ | $R_{17}$ | $R_{18}$ | Y | Salt | Physical data (°C.) |
|---|---|---|---|---|---|---|---|
| 5.31 | H | $CH_3$ | 2-Cl | H | N | $HNO_3$ | |
| 5.32 | H | $CH_3$ | 2-Cl | 6-Cl | N | — | |
| 5.33 | H | $CH_3$ | 2-Cl | H | CH | — | |
| 5.34 | H | $CH_3$ | 2-$OCH_3$ | 6-$OCH_3$ | CH | — | |
| 5.35 | H | $CH_3$ | 3-Cl | H | N | — | |
| 5.36 | H | $CH_3$ | 2-$CH_3$ | H | N | $HNO_3$ | m.p. 132–134° |
| 5.37 | H | $CH_3$ | 3-$CH_3$ | H | N | — | |
| 5.38 | H | $C_2H_5$ | 3-$CH_3$ | H | CH | $CuCl_2$ | |
| 5.39 | H | $C_2H_5$ | 2-$CH_3$ | 6-$CH_3$ | N | — | |
| 5.40 | H | $C_2H_5$ | 2-$CH_3$ | H | N | $HNO_3$ | m.p. 108–110° |
| 5.41 | H | $C_2H_5$ | 2-Br | 5-Br | N | — | |
| 5.42 | H | $C_2H_5$ | 2-Cl | H | N | — | oil, $n_D^{22}$ 1.5620 |
| 5.43 | H | $C_3H_7$-n | 2-Cl | H | N | — | |
| 5.44 | H | $C_3H_7$-n | 2-Cl | 6-Cl | N | — | |
| 5.45 | H | $C_3H_7$-i | 2-$CH_3$ | H | N | — | |
| 5.46 | H | $C_3H_7$-i | 2-$CH_3$ | H | CH | — | |
| 5.47 | H | $C_3H_7$-i | 2-$OCH_3$ | 6-$OCH_3$ | N | $MnCl_2$ | |
| 5.48 | $C_2H_5$ | $C_2H_5$ | 2-Cl | H | N | — | |
| 5.49 | $C_2H_5$ | $C_2H_5$ | 2-Cl | H | N | $HNO_3$ | |
| 5.50 | $C_2H_5$ | $C_2H_5$ | 2-Cl | 6-Cl | N | HCl | |
| 5.51 | H | H | 2-$OCH_3$ | 6-$OCH_3$ | CH | — | |
| 5.52 | $C_2H_5$ | $C_3H_7$-i | 2-$CH_3$ | H | N | — | |
| 5.53 | H | $C_2H_5$ | 2-$OCH_3$ | 6-$OCH_3$ | N | — | |
| 5.54 | H | $C_2H_5$ | 2-$OCH_3$ | 6-$OCH_3$ | N | — | |
| 5.55 | H | H | 2-$OCH_3$ | 6-$OCH_3$ | N | — | |
| 5.56 | $CH_3$ | $C_2H_5$ | 3-Cl | H | N | $(COOH)_2$ | |
| 5.57 | $CH_3$ | $C_2H_5$ | 2-$CH_3$ | 6-$CH_3$ | CH | $(COOH)_2$ | |
| 5.58 | $CH_3$ | $C_3H_7$-i | 2-Cl | H | N | — | |
| 5.59 | $CH_3$ | $C_3H_7$-i | 2-Cl | 6-Cl | N | $H_2SO_4$ | |
| 5.60 | —$(CH_2)_4$— | | 2-Cl | H | CH | — | |
| 5.61 | —$(CH_2)_4$— | | 2-Cl | H | CH | $HNO_3$ | |
| 5.62 | —$(CH_2)_4$— | | 2-Cl | H | N | — | |
| 5.63 | —$(CH_2)_4$— | | 3-Cl | H | N | $Mn(NO_3)_2$ | |
| 5.64 | —$(CH_2)_4$— | | 3-Cl | 6-Cl | N | $(COOH)_2$ | |
| 5.65 | —$(CH_2)_4$— | | 3-Cl | 5-Cl | N | $ZnCl_2$ | |
| 5.66 | —$(CH_2)_4$— | | 3-Cl | 6-Cl | N | HCl | |
| 5.67 | —$(CH_2)_4$— | | 2-Cl | H | CH | $ZnCl_2$ | |
| 5.68 | H | H | 2-$CH_3$ | H | CH | — | m.p. 103–106° |
| 5.69 | $CH_3$ | $CH_3$ | 2-$CH_3$ | H | CH | — | |
| 5.70 | H | $C_3H_7$-n | 2-$CH_3$ | H | CH | — | yellow resin, $n_D^{50}$ 1.5476 |
| 5.71 | H | $CH_2OCH_3$ | 2-$CH_3$ | H | CH | — | resin |
| 5.72 | H | $CH_3$ | 2-$CH_3$ | H | CH | — | resin |
| 5.73 | H | $C_2H_5$ | 2-$CH_3$ | H | CH | — | resin, $n_D^{50}$ 1.5557 |
| 5.74 | H | $CH_2OH$ | 2-$CH_3$ | H | CH | — | |
| 5.75 | H | $CH_2OCH_3$ | 2-$CH_3$ | H | N | — | oil, $n_D^{50}$ 1.5482 |
| 5.76 | H | $C_2H_5$ | 2-$CH_3$ | H | N | — | resin, $n_D^{50}$ 1.5502 |
| 5.77 | H | H | 2-$CH_3$ | H | N | — | m.p. 103–105° |
| 5.78 | H | $C_3H_7$-n | 2-$CH_3$ | H | N | — | resin, $n_D^{50}$ 1.5467 |
| 5.79 | H | $CH_2OH$ | 2-Cl | H | CH | — | |
| 5.80 | H | $C_2H_5$ | 2-Br | H | CH | — | |
| 5.81 | H | $C_2H_5$ | 2-Cl | H | CH | — | resin, $n_D^{22}$ 1.5765 |
| 5.82 | H | $CH_2OCH_3$ | 2-Cl | H | CH | — | |
| 5.83 | H | $CH_2OCH_3$ | 2-Cl | H | N | — | |
| 5.84 | H | $CH_2OH$ | 2-Br | H | CH | — | |
| 5.85 | H | $CH_2OCH_3$ | 2-Br | H | CH | — | |
| 5.86 | $CH_3$ | $CH_3$ | 2-Br | H | N | — | |
| 5.87 | H | $CH_2OCH_3$ | 2-Br | H | N | — | |
| 5.88 | H | $CH_2OH$ | 3-$NO_2$ | H | CH | — | |
| 5.89 | H | $C_3H_7$-n | 3-$NO_2$ | H | N | — | |
| 5.90 | H | $C_2H_5$ | 2-Br | H | N | — | |
| 5.91 | H | $C_2H_5$ | 3-$NO_2$ | H | CH | — | |
| 5.92 | H | $CH_3$ | 3-$NO_2$ | H | CH | — | |
| 5.93 | H | $C_2H_5$ | 3-$NO_2$ | H | N | — | |
| 5.94 | H | $CH_3$ | 3-$NO_2$ | H | N | — | |
| 5.95 | H | $CH_2OH$ | 3-$CH_3$ | H | CH | — | |
| 5.96 | H | $CH_2OCH_3$ | 3-$CH_3$ | H | N | — | |

TABLE 5-continued

Compounds of the formula

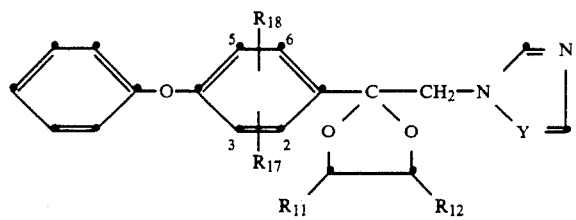

including the isomeric forms:

| Compound | $R_{11}$ | $R_{12}$ | $R_{17}$ | $R_{18}$ | Y | Salt | Physical data (°C.) |
|---|---|---|---|---|---|---|---|
| 5.97 | H | $C_2H_5$ | 2-$NO_2$ | H | CH | — | |
| 5.98 | H | $CH_2OCH_3$ | 2-$NO_2$ | H | CH | — | |
| 5.99 | H | $CH_2OCH_3$ | 2-$NO_2$ | H | N | — | |
| 5.100 | H | $C_2H_5$ | 3-$CH_3$ | H | CH | — | oil, $n_D^{20.5}$ 1.5692 |
| 5.101 | H | $CH_2OCH_3$ | 3-$CH_3$ | H | CH | — | |
| 5.102 | H | $C_2H_5$ | 3-$CH_3$ | H | N | — | oil, $n_D^{20}$ 1.5577 |
| 5.103 | H | $CH_2OH$ | 2-$NO_2$ | H | CH | — | |
| 5.104 | H | $C_2H_5$ | 2-$NO_2$ | H | N | — | |
| 5.105 | 2-$CH_3$ | H | 2-$CH_3$ | 5-$CH_3$ | CH | — | $n_D^{50}$ 1.5463 |
| 5.106 | H | $C_3H_7$-n | 2-$CH_3$ | H | N | — | $n_D^{22}$ 1.5461 A |
| 5.107 | H | $C_3H_7$-n | 2-$CH_3$ | H | N | — | $n_D^{22}$ 1.5468 B |
| 5.108 | H | $C_2H_5$ | 3-$CH_3$ | H | N | — | $n_D^{50}$ 1.5638 |
| 5.109 | H | $C_2H_5$ | 3-$CH_3$ | H | CH | — | $n_D^{50}$ 1.5732 |
| 5.110 | H | $C_2H_5$ | 2-$C_2H_5$ | H | N | $HNO_3$ | 132–134° |
| 5.111 | H | $C_2H_5$ | 2-$CH_3$ | H | CH | $(COOH)_2$ | 115–118° |
| 5.112 | H | $C_2H_5$ | 2-$C_2H_5$ | H | N | — | $n_D^{22}$ 1.5642 |
| 5.113 | H | $C_2H_5$ | 3-$CH_3$ | H | N | — | $n_D^{22}$ 1.5631; A |
| 5.114 | H | $C_2H_5$ | 3-$CH_3$ | H | N | — | $n_D^{22}$ 1.5633 |
| 5.115 | H | $C_2H_5$ | 2-$C_2H_5$ | H | CH | — | brown resin |
| 5.116 | H | $CH_3$ | 2-$C_2H_5$ | H | CH | $HNO_3$ | m.p. 105–119° |
| 5.117 | H | $CH_3$ | 2-$C_2H_5$ | H | CH | — | viscous oil |
| 5.118 | H | $CH_3$ | 2-$C_2H_5$ | H | N | $HNO_3$ | m.p. 136–138° |
| 5.119 | H | $C_2H_5$ | 2-$CH_3$ | H | CH | HCl | m.p. 166–171° |
| 5.120 | H | $C_2H_5$ | 2-$CH_3$ | H | CH | $H_2SO_4$ | m.p. 136–138° |
| 5.121 | H | $C_2H_5$ | 2-$CH_3$ | H | CH | $CH_3SO_3H$ | m.p. 98–106° |
| 5.122 | H | $C_2H_5$ | 2-$CH_3$ | H | CH | $HNO_3$ | m.p. 96–98° |
| 5.123 | H | $C_2H_5$ | 2-$C_2H_5$ | H | CH | $HNO_3$ | m.p. 134–137° |
| 5.124 | H | $C_2H_5$ | 2-$CH_3$ | H | CH | — | oil A |
| 5.125 | H | $C_2H_5$ | 2-$CH_3$ | H | CH | — | oil B |

TABLE 6

Compounds of the formula (XXVI)

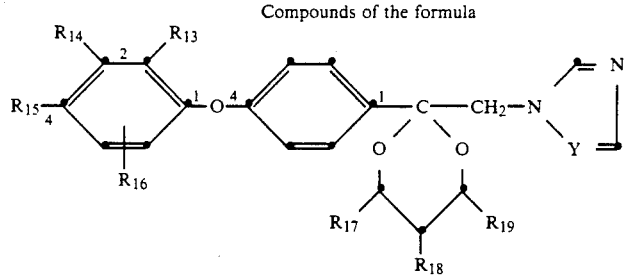

including the isomeric forms:

| Compound | $R_{13}$ | $R_{14}$ | $R_{15}$ | $R_{16}$ | $R_{17}$ | $R_{18}$ | $R_{19}$ | Y | Salt | Physical data (°C.) |
|---|---|---|---|---|---|---|---|---|---|---|
| 6.1 | H | H | H | H | H | H | H | N | — | m.p. 129–130° |
| 6.2 | H | H | H | H | H | $C_2H_5$ | H | N | — | |
| 6.3 | H | H | Cl | H | H | $CH_3$ | H | CH | — | |
| 6.4 | H | H | H | H | $CH_3$ | $CH_3$ | H | N | — | |
| 6.5 | H | H | H | H | $CH_3$ | $CH_3$ | H | N | $HNO_3$ | |
| 6.6 | H | H | H | H | $CH_3$ | $CH_3$ | $CH_3$ | N | — | |
| 6.7 | H | H | H | H | $CH_3$ | $CH_3$ | $CH_3$ | N | $HNO_3$ | |
| 6.8 | H | H | H | H | $CH_3$ | H | H | N | — | m.p. 99.5–101° |
| 6.9 | Cl | H | Cl | H | $CH_3$ | $CH_3$ | $CH_3$ | N | $Mn(NO_3)_2$ | |
| 6.10 | $CH_3$ | H | $CH_3$ | H | $CH_3$ | $CH_3$ | $CH_3$ | N | $CuCl_2$ | |
| 6.11 | $CH_3$ | H | $CH_3$ | H | $CH_3$ | $CH_3$ | $CH_3$ | N | $(COOH)_2$ | |
| 6.12 | Cl | H | H | 6-Cl | $CH_3$ | $CH_3$ | $CH_3$ | CH | $HNO_3$ | |
| 6.13 | Cl | H | H | 5-Cl | $CH_3$ | $CH_3$ | $CH_3$ | CH | $CuCl_2$ | |
| 6.14 | Cl | H | Cl | 6-Cl | $CH_3$ | $CH_3$ | $CH_3$ | CH | $FeCl_3$ | |
| 6.15 | Cl | H | Cl | H | $CH_3$ | H | $CH_3$ | N | — | |

TABLE 6-continued

Compounds of the formula (XXVI)

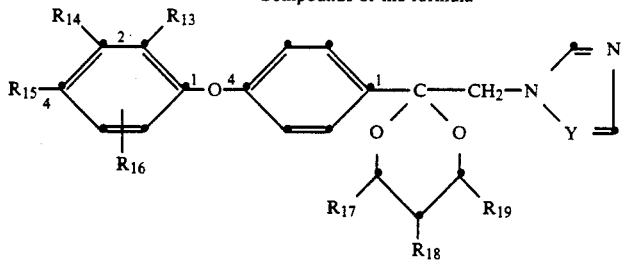

including the isomeric forms:

| Compound | $R_{13}$ | $R_{14}$ | $R_{15}$ | $R_{16}$ | $R_{17}$ | $R_{18}$ | $R_{19}$ | Y | Salt | Physical data (°C.) |
|---|---|---|---|---|---|---|---|---|---|---|
| 6.16 | Cl | Cl | Cl | H | $CH_3$ | H | $C_2H_5$ | N | — | |
| 6.17 | H | H | H | H | $C_2H_5$ | H | H | N | — | m.p. 103–109° |
| 6.18 | $CH_3$ | H | H | H | $CH_3$ | H | H | N | — | |
| 6.19 | $CH_3$ | H | H | 6-$CH_3$ | $CH_3$ | H | H | N | $HNO_3$ | |
| 6.20 | H | H | H | 5-$CH_3$ | $CH_3$ | $C_2H_5$ | H | N | — | |
| 6.21 | H | Cl | H | 6-Cl | $CH_3$ | $C_2H_5$ | H | CH | — | |
| 6.22 | H | Cl | H | 6-Cl | $C_2H_5$ | $C_2H_5$ | $CH_3$ | N | — | |
| 6.23 | H | H | $CH_3$ | H | $C_2H_5$ | $C_2H_5$ | $C_2H_5$ | N | $Mn(NO_3)_2$ | |
| 6.24 | H | H | H | H | $C_3H_7$-n | H | $C_3H_7$-n | N | — | |
| 6.25 | H | $CH_3$ | H | H | $C_3H_7$-n | H | $C_3H_7$-n | CH | — | |
| 6.26 | Cl | H | H | H | $C_3H_7$-n | $C_3H_7$-n | H | N | — | |
| 6.27 | Cl | H | Cl | H | $C_3H_7$-n | $C_2H_5$ | $CH_3$ | N | — | |
| 6.28 | Cl | Cl | Cl | 6-Cl | $C_3H_7$-n | $C_2H_5$ | $CH_3$ | CH | — | |
| 6.29 | H | H | Cl | H | $C_3H_7$-n | $C_2H_5$ | $CH_3$ | N | $ZnCl_2$ | |
| 6.30 | H | H | Br | H | $C_3H_7$-n | $CH_3$ | $C_2H_5$ | N | — | |
| 6.31 | $CH_3$ | H | $CH_3$ | H | $C_2H_5$ | $C_3H_7$-n | $CH_3$ | N | — | |
| 6.32 | H | H | $CH_3$ | H | $C_4H_9$-n | $CH_3$ | H | N | — | |
| 6.33 | Cl | H | H | 6-Cl | $C_4H_9$-n | H | $CH_3$ | N | $FeCl_3$ | |
| 6.34 | Cl | H | H | 6-Cl | $C_3H_7$-n | H | $CH_3$ | CH | — | |
| 6.35 | H | H | Cl | H | $CH_3$ | H | $C_4H_9$-n | N | — | |
| 6.36 | F | H | H | H | H | H | $C_4H_9$-n | CH | — | |
| 6.37 | H | H | H | H | $C_4H_9$-n | H | H | CH | — | |
| 6.38 | H | H | H | H | $C_4H_9$-n | H | H | N | $HNO_3$ | |
| 6.39 | Cl | H | H | H | H | $C_4H_9$-n | H | N | — | |
| 6.40 | Cl | H | Cl | $CH_3$ | H | $C_4H_9$-n | H | CH | HCl | |
| 6.41 | H | Cl | H | H | $CH_3$ | $C_4H_9$-n | H | N | — | |
| 6.42 | H | Cl | H | H | H | $C_4H_9$-sec | H | N | $HNO_3$ | |
| 6.43 | H | Cl | Cl | H | H | $C_4H_9$-sec | H | N | — | |
| 6.44 | H | Br | H | H | $CH_3$ | $C_4H_9$-sec | H | N | — | |
| 6.45 | H | Br | H | 6-Br | $CH_3$ | $C_3H_7$-sec | H | CH | — | |
| 6.46 | $CH_3$ | H | H | 5-Br | $CH_3$ | $C_3H_7$-i | H | N | — | |
| 6.47 | H | H | $CH_3$ | H | $CH_3$ | $C_3H_7$-i | H | N | $Mn(NO_3)_2$ | |
| 6.48 | H | Cl | H | H | $CH_3$ | $C_3H_7$-i | $CH_3$ | N | — | |
| 6.49 | Cl | H | Cl | H | $C_2H_5$ | $C_3H_7$-i | H | N | — | |
| 6.50 | (CH=CH)$_2$ | H | H | H | H | H | H | N | — | |
| 6.51 | (CH=CH)$_2$ | H | H | H | H | $CH_3$ | H | CH | $Mn(NO_3)_2$ | |
| 6.52 | (CH=CH)$_2$ | H | H | 6-Cl | H | $CH_3$ | H | N | — | |
| 6.53 | (CH=CH)$_2$ | H | H | 6-$CH_3$ | $CH_3$ | $CH_3$ | H | N | — | |
| 6.54 | (CH=CH)$_2$ | Cl | H | 6-Cl | H | $CH_3$ | H | N | — | |
| 6.55 | (CH=CH)$_2$ | H | H | 6-Cl | $CH_3$ | $CH_3$ | $CH_3$ | N | — | |
| 6.56 | (CH=CH)$_2$ | H | H | 6-Cl | $CH_3$ | $CH_3$ | $CH_3$ | CH | — | |
| 6.57 | (CH=CH)$_2$ | Cl | H | 6-Cl | $C_3H_7$-i | H | H | N | HCl | |
| 6.58 | (CH=CH)$_2$ | H | H | 6-Cl | H | $C_2H_5$ | H | N | — | |
| 6.59 | (CH=CH)$_2$ | H | H | H | $CH_3$ | $CH_3$ | $CH_3$ | N | — | |
| 6.60 | (CH=CH)$_2$ | H | H | H | $CH_3$ | $CH_3$ | $CH_3$ | CH | — | |
| 6.61 | H | (CH=CH)$_2$ | H | H | H | H | H | N | — | |
| 6.62 | H | (CH=CH)$_2$ | H | H | H | H | H | N | $CuCl_2$ | |
| 6.63 | H | (CH=CH)$_2$ | H | H | H | $CH_3$ | H | N | — | |
| 6.64 | H | (CH=CH)$_2$ | H | H | $CH_3$ | H | H | N | — | |
| 6.65 | H | (CH=CH)$_2$ | H | H | $CH_3$ | $CH_3$ | $CH_3$ | N | — | |
| 6.66 | H | (CH=CH)$_2$ | H | H | H | H | H | CH | — | |
| 6.67 | Cl | (CH=CH)$_2$ | H | H | H | H | H | N | — | |
| 6.68 | Cl | (CH=CH)$_2$ | H | H | $CH_3$ | $CH_3$ | $CH_3$ | N | — | |
| 6.69 | Cl | (CH=CH)$_2$ | H | H | $C_2H_5$ | H | H | N | — | |
| 6.70 | Cl | (CH=CH)$_2$ | 6-Cl | $CH_3$ | $CH_3$ | $CH_3$ | | N | — | |
| 6.71 | H | (CH=CH)$_2$ | 6-Cl | $CH_3$ | $CH_3$ | $CH_3$ | | N | — | |
| 6.72 | Br | (CH=CH)$_2$ | H | $CH_3$ | $C_2H_5$ | $CH_3$ | | N | — | |
| 6.73 | $CH_3$ | (CH=CH)$_2$ | H | $CH_3$ | $CH_3$ | $CH_3$ | | N | — | |
| 6.74 | Cl | Cl | H | 5-Cl | H | H | H | N | — | |
| 6.75 | Cl | H | Cl | 5-Cl | H | H | H | N | — | |
| 6.76 | $CH_3$ | $CH_3$ | H | H | H | H | H | CH | — | |
| 6.77 | F | H | H | H | $CH_3$ | H | H | N | — | |
| 6.78 | H | F | H | H | H | H | H | N | — | |
| 6.79 | H | H | F | H | H | H | H | $CH_3$ | — | m.p. 95–98° viscous mass, $n_D^{24}$ |

TABLE 6-continued

Compounds of the formula (XXVI)

[Structure: R14, R13 on one benzene ring with R15 (position 4), R16; linked via O to second benzene ring, then C-CH2-N with Y=N ring; dioxolane with R17, R18, R19]

including the isomeric forms:

| Compound | $R_{13}$ | $R_{14}$ | $R_{15}$ | $R_{16}$ | $R_{17}$ | $R_{18}$ | $R_{19}$ | Y | Salt | Physical data (°C.) |
|---|---|---|---|---|---|---|---|---|---|---|
| 6.80 | H | H | F | H | $CH_3$ | H | H | CH | — | 1.5656 |
| 6.81 | H | H | F | H | $CH_3$ | H | H | N | — | viscous mass, $n_D^{24.5}$ 1.5551 |
| 6.82 | Cl | H | H | H | $CH_3$ | H | H | N | — | |
| 6.83 | Br | H | H | H | $CH_3$ | H | H | N | — | |
| 6.84 | Br | H | H | H | H | H | H | N | — | |
| 6.85 | H | Br | H | H | H | H | H | CH | — | |
| 6.86 | H | Br | H | H | H | H | H | N | — | |
| 6.87 | H | H | Br | H | H | H | H | CH | — | |
| 6.88 | H | H | Br | H | $CH_3$ | H | H | CH | — | |
| 6.89 | H | H | Br | H | H | H | H | N | — | |
| 6.90 | H | H | I | H | H | H | H | CH | — | |
| 6.91 | H | H | I | H | H | H | H | N | — | |
| 6.92 | H | H | F | H | H | H | H | N | — | m.p. 105–107° |
| 6.93 | H | H | H | H | $CH_3$ | H | H | CH | — | m.p. 82–84° |
| 6.94 | H | H | Cl | H | $CH_3$ | H | H | N | — | $n_D^{25}$ 1.5748, resin |

TABLE 7

Compounds of the formula (XXVII)

[Structure: R14, R13 on benzene ring with R15 (position 4), R16 (positions 5,6); linked via O to second benzene ring, then C-CH2-N with Y=N ring; dioxolane with R24, R22, R23]

[$R_{13}$ = $R_{14}$ = H]
including the isomeric forms:

| Compound | $R_{22}$ | $R_{23}$ | $R_{24}$ | $R_{15}$ | $R_{16}$ | Y | Salt | Physical data (°C.) |
|---|---|---|---|---|---|---|---|---|
| 7.1 | H | $CH_3$ | H | H | H | N | — | |
| 7.2 | H | $CH_3$ | H | H | H | CH | — | |
| 7.3 | $CH_3$ | $CH_3$ | H | H | H | N | — | m.p. 122–124° |
| 7.4 | $CH_3$ | $CH_3$ | H | H | H | N | $HNO_3$ | |
| 7.5 | $CH_3$ | $CH_3$ | $CH_3$ | H | H | N | $Mn(NO_3)_2$ | |
| 7.6 | $CH_3$ | $CH_3$ | $CH_3$ | H | H | CH | — | |
| 7.7 | $CH_3$ | $CH_3$ | H | Cl | 6-Cl | — | — | oil; $n_D^{23}$ = 1.5782 |
| 7.8 | $CH_3$ | $C_2H_5$ | H | H | H | N | — | |
| 7.9 | $CH_3$ | $C_2H_5$ | H | H | H | N | $CuCl_2$ | |
| 7.10 | $CH_3$ | $C_2H_5$ | $CH_3$ | $CH_3$ | 6-$CH_3$ | CH | $(COOH)_2$ | |
| 7.11 | $C_2H_5$ | $C_2H_5$ | H | H | H | N | $HNO_3$ | |
| 7.12 | $C_2H_5$ | $C_2H_5$ | H | H | H | N | — | |
| 7.13 | $C_2H_5$ | $C_2H_5$ | H | H | H | CH | HCl | |
| 7.14 | $C_2H_5$ | $C_2H_5$ | H | H | H | CH | $FeCl_3$ | |
| 7.15 | $C_2H_5$ | $C_2H_5$ | H | H | H | CH | — | |
| 7.16 | H | $C_2H_5$ | H | $CH_3$ | H | N | — | |
| 7.17 | H | $C_2H_5$ | H | H | H | N | $HNO_3$ | |
| 7.18 | H | $C_2H_5$ | H | H | H | CH | — | |
| 7.19 | H | $C_3H_7$-n | H | H | H | N | $CuCl_2$ | |
| 7.20 | H | $C_3H_7$-n | H | H | H | CH | — | |
| 7.21 | $CH_3$ | $CH_3$ | $C_3H_7$-n | H | H | N | — | m.p. 119–121° |
| 7.22 | H | H | H | H | H | CH | — | |
| 7.23 | $CH_3$ | $CH_3$ | H | H | H | CH | — | |
| 7.24 | H | H | $CH_3$ | H | H | CH | — | |

TABLE 7-continued

Compounds of the formula (XXVII)

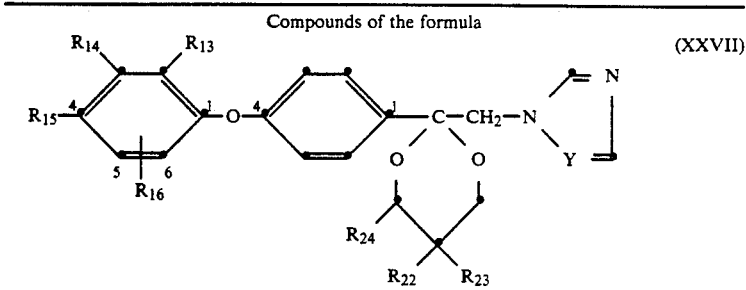

[$R_{13} = R_{14} = H$]
including the isomeric forms:

| Compound | $R_{22}$ | $R_{23}$ | $R_{24}$ | $R_{15}$ | $R_{16}$ | Y | Salt | Physical data (°C.) |
|---|---|---|---|---|---|---|---|---|
| 7.25 | H | H | $CH_3$ | H | H | N | ½ $CuSO_4$ | |
| 7.26 | H | H | H | H | 6-F | N | — | |
| 7.27 | H | H | H | F | H | N | — | m.p. 105–107° |
| 7.28 | H | H | H | H | 6-Cl | N | — | |
| 7.29 | H | H | $CH_3$ | H | 6-Cl | CH | — | |
| 7.30 | H | H | H | H | 5-Cl | CH | — | |
| 7.31 | H | H | H | H | 5-Cl | N | — | |
| 7.32 | H | H | $CH_3$ | Cl | H | CH | — | |
| 7.33 | H | H | H | Cl | H | CH | — | m.p. 116–118° |
| 7.34 | H | H | H | Cl | H | N | — | m.p. 101–103° |
| 7.35 | H | H | $CH_3$ | Cl | H | N | — | |
| 7.36 | H | H | H | $CH_3$ | H | N | — | |
| 7.37 | H | H | H | $C_3H_7$-i | H | N | — | |
| 7.38 | H | H | H | $NO_2$ | H | N | — | |
| 7.39 | H | H | H | H | 6-$CF_3$ | N | — | |
| 7.40 | H | H | $CH_3$ | H | 5-$CF_3$ | N | — | |
| 7.41 | H | H | H | $CF_3$ | H | N | — | |
| 7.42 | H | H | H | Cl | 5-Cl | N | — | |
| 7.43 | H | H | H | Cl | 5-$CH_3$ | CH | — | |
| 7.44 | $CH_3$ | $C_2H_5$ | H | $NO_2$ | 5-$CH_3$ | N | — | |
| 7.45 | $CH_3$ | $CH_3$ | H | $CF_3$ | 6-Cl | CH | — | |
| 7.46 | $CH_3$ | $CH_3$ | $C_3H_7$-n | $CF_3$ | 6-$NO_2$ | CH | — | |

TABLE 8

Compounds of the formula (XXVIII)

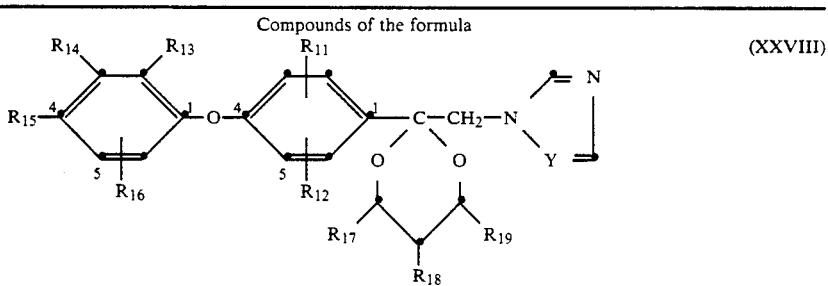

including the isomeric forms:

| Compound | $R_{11}$ | $R_{12}$ | $R_{13}$ | $R_{14}$ | $R_{15}$ | $R_{16}$ | $R_{17}$ | $R_{18}$ | $R_{19}$ | Y | Salt | Physical data (°C.) |
|---|---|---|---|---|---|---|---|---|---|---|---|---|
| 8.1 | 2-Cl | H | $CH_3$ | H | H | H | H | H | H | N | — | |
| 8.2 | 2-Cl | H | H | H | H | H | H | $C_2H_5$ | H | N | — | |
| 8.3 | 2-Cl | H | H | H | H | H | H | $CH_3$ | H | CH | — | |
| 8.4 | 2-Cl | 5-Cl | H | H | H | H | $CH_3$ | $CH_3$ | H | N | — | |
| 8.5 | 2-$CH_3$ | H | H | H | H | H | $CH_3$ | H | H | N | $HNO_3$ | |
| 8.6 | 2-$CH_3$ | H | H | H | F | H | H | H | H | N | — | |
| 8.7 | 2-Cl | H | Cl | H | H | H | $CH_3$ | $CH_3$ | $CH_3$ | N | $HNO_3$ | |
| 8.8 | 2-Cl | 6-Cl | Cl | H | Cl | H | $CH_3$ | H | H | N | — | |
| 8.9 | 2-Br | H | H | H | H | H | $CH_3$ | $CH_3$ | $CH_3$ | N | $Mn(NO_3)_2$ | |
| 8.10 | 2-$CH_3$ | H | $CH_3$ | H | H | H | $CH_3$ | H | H | N | — | |
| 8.11 | 2-$OCH_3$ | 6-$OCH_3$ | H | H | Cl | H | H | H | H | CH | — | |
| 8.12 | 2-Cl | H | H | Cl | Cl | 6-Cl | $CH_3$ | $CH_3$ | $CH_3$ | CH | $HNO_3$ | |
| 8.13 | 3-Cl | H | H | H | H | H | $CH_3$ | $CH_3$ | $CH_3$ | CH | $CuCl_2$ | |
| 8.14 | 3-Br | H | H | H | H | H | $CH_3$ | $CH_3$ | $CH_3$ | CH | $FeCl_3$ | |
| 8.15 | 3-Br | 5-Br | H | H | H | H | $CH_3$ | H | $CH_3$ | N | — | |
| 8.16 | 2-Cl | H | H | H | H | H | $CH_3$ | H | $C_2H_5$ | N | — | |
| 8.17 | 2-Cl | 6-Cl | H | Cl | H | H | $C_2H_5$ | H | $C_2H_5$ | N | — | |
| 8.18 | 2-Cl | 6-Cl | H | H | H | H | $CH_3$ | H | H | N | — | |
| 8.19 | 2-Cl | 5-Cl | H | Cl | H | H | $CH_3$ | H | H | N | $HNO_3$ | |
| 8.20 | 2-$OCH_3$ | 6-$OCH_3$ | H | H | Cl | H | H | H | H | N | — | |
| 8.21 | 2-$CH_3$ | 6-$CH_3$ | $CH_3$ | H | $CH_3$ | H | $CH_3$ | $C_2H_5$ | H | CH | — | |

TABLE 8-continued

Compounds of the formula (XXVIII)

including the isomeric forms:

| Compound | $R_{11}$ | $R_{12}$ | $R_{13}$ | $R_{14}$ | $R_{15}$ | $R_{16}$ | $R_{17}$ | $R_{18}$ | $R_{19}$ | Y | Salt | Physical data (°C.) |
|---|---|---|---|---|---|---|---|---|---|---|---|---|
| 8.22 | 2-Br | 6-CH$_3$ | | H | H | H | C$_2$H$_5$ | C$_2$H$_5$ | CH$_3$ | N | — | |
| 8.23 | 2-Cl | H | Cl | H | Cl | H | C$_2$H$_5$ | C$_2$H$_5$ | C$_2$H$_5$ | N | Mn(NO$_3$)$_2$ | |
| 8.24 | 3-Cl | H | (CH=CH)$_2$ | H | H | H | H | H | H | N | — | |
| 8.25 | H | H | (CH=CH)$_2$ | H | H | H | H | H | H | CH | Mn(NO$_3$)$_2$ | |
| 8.26 | 2-Cl | H | (CH=CH)$_2$ | H | H | H | H | H | H | N | — | |
| 8.27 | 2-Cl | H | (CH=CH)$_2$ | H | 2-Cl | H | CH$_3$ | H | H | N | — | |
| 8.28 | 2-Cl | 6-Cl | (CH=CH)$_2$ | Cl | H | H | CH$_3$ | CH$_3$ | CH$_3$ | N | — | |
| 8.29 | 2-Cl | H | (CH=CH)$_2$ | H | H | H | CH$_3$ | CH$_3$ | CH$_3$ | N | — | |
| 8.30 | 2-Cl | 6-Cl | (CH=CH)$_2$ | H | H | H | CH$_3$ | CH$_3$ | CH$_3$ | N | CuCl$_2$ | |
| 8.31 | 2-CH$_3$ | H | (CH=CH)$_2$ | H | H | H | CH$_3$ | CH$_3$ | CH$_3$ | N | — | |
| 8.32 | 2-CH$_3$ | 6-CH$_3$ | (CH=CH)$_2$ | H | H | H | CH$_3$ | CH$_3$ | CH$_3$ | CH | HCl | |
| 8.33 | 2-Br | H | (CH=CH)$_2$ | H | 2-Br | H | CH$_3$ | H | H | N | — | |
| 8.34 | 2-Cl | 5-Cl | (CH=CH)$_2$ | H | H | H | CH$_3$ | CH$_3$ | CH$_3$ | N | — | |
| 8.35 | 2-Cl | 5-Cl | (CH=CH)$_2$ | H | H | H | CH$_3$ | CH$_3$ | H | N | — | |
| 8.36 | H | H | H | (CH=CH)$_2$ | H | H | H | H | H | CH | MnCl$_2$ | |
| 8.37 | 3-Cl | H | H | (CH=CH)$_2$ | H | H | H | H | H | N | — | |
| 8.38 | 2-Cl | H | H | (CH=CH)$_2$ | H | H | CH$_3$ | H | H | N | — | |
| 8.39 | 2-Cl | H | H | (CH=CH)$_2$ | H | H | CH$_3$ | CH$_3$ | H | N | — | |
| 8.40 | 2-Cl | H | Cl | (CH=CH)$_2$ | 3-Cl | H | CH$_3$ | H | H | N | — | |
| 8.41 | 2-Cl | 6-Cl | H | (CH=CH)$_2$ | 4-Cl | CH$_3$ | CH$_3$ | H | | CH | — | |
| 8.42 | 2-Cl | H | Cl | (CH=CH)$_2$ | H | H | CH$_3$ | CH$_3$ | CH$_3$ | N | — | |
| 8.43 | 2-Cl | 5-Cl | H | (CH=CH)$_2$ | H | H | CH$_3$ | CH$_3$ | CH$_3$ | N | — | |
| 8.44 | 2-Cl | 3-Cl | H | (CH=CH)$_2$ | 4-Br | CH$_3$ | H | CH$_3$ | | N | — | |
| 8.45 | 2-CH$_3$ | 3-Cl | Cl | (CH=CH)$_2$ | H | H | CH$_3$ | CH$_3$ | H | N | — | |
| 8.46 | 2-CH$_3$ | 5-CH$_3$ | H | (CH=CH)$_2$ | H | H | CH$_3$ | CH$_3$ | H | N | HCl | |
| 8.47 | 2-CH$_3$ | H | CH$_3$ | (CH=CH)$_2$ | H | H | CH$_3$ | H | CH$_3$ | N | — | |
| 8.48 | 2-Cl | H | Cl | (CH=CH)$_2$ | H | H | H | C$_2$H$_5$ | H | N | — | |
| 8.49 | 2-Cl | H | Cl | (CH=CH)$_2$ | H | H | C$_2$H$_5$ | CH$_3$ | H | N | — | |
| 8.50 | 2-CH$_3$ | H | H | H | H | H | H | H | H | CH | — | |
| 8.51 | 2-CH$_3$ | H | H | H | H | H | CH$_3$ | H | H | CH | — | |
| 8.52 | 2-CH$_3$ | H | H | H | H | H | CH$_3$ | H | H | N | — | |
| 8.53 | 2-CH$_3$ | H | H | H | H | H | H | H | H | N | — | |
| 8.54 | 2-Cl | H | H | H | H | H | H | H | H | CH | — | |
| 8.55 | 2-Cl | H | H | H | H | H | H | H | H | N | — | |
| 8.56 | 2-Cl | H | H | H | H | H | CH$_3$ | H | H | N | — | |
| 8.57 | 3-NO$_2$ | H | H | H | H | H | H | H | H | CH | — | |
| 8.58 | 2-Br | H | H | H | H | H | H | H | H | CH | — | |
| 8.59 | 2-Br | H | H | H | H | H | H | H | H | N | — | |
| 8.60 | 3-CH$_3$ | H | H | H | H | H | H | H | H | CH | — | |
| 8.61 | 3-CH$_3$ | H | H | H | H | H | H | H | H | N | — | |
| 8.62 | 2-NO$_2$ | H | H | H | H | H | H | H | H | N | — | |
| 8.63 | 2-Cl | H | H | H | Cl | H | H | H | H | N | — | |
| 8.64 | H | H | Cl | H | H | 5-Cl | H | H | H | N | — | |
| 8.65 | H | H | H | Cl | H | 5-Cl | H | H | H | N | — | |
| 8.66 | 2-CH$_3$ | H | H | F | H | H | H | H | H | CH | — | brown resin |
| 8.67 | 2-CH$_3$ | H | F | H | H | H | H | H | H | N | — | |
| 8.68 | 2-CH$_3$ | H | H | H | Cl | H | H | H | H | N | — | |
| 8.69 | 2-CH$_3$ | H | H | H | Cl | H | H | H | H | CH | — | brown resin |
| 8.70 | 2-CH$_3$ | H | H | H | Cl | H | CH$_3$ | H | H | N | — | |
| 8.71 | 2-CH$_3$ | H | H | H | Cl | H | CH$_3$ | H | H | CH | — | |
| 8.72 | 2-CH$_3$ | H | H | H | F | H | H | H | H | N | — | m.p. 127–137° |
| 8.73 | 2-CH$_3$ | H | H | H | F | H | H | H | H | CH | — | |
| 8.74 | 2-CH$_3$ | H | H | H | F | H | CH$_3$ | H | H | N | — | |
| 8.75 | 2-CH$_3$ | H | H | H | F | H | CH$_3$ | H | H | CH | — | |

TABLE 9

Compound of the formula

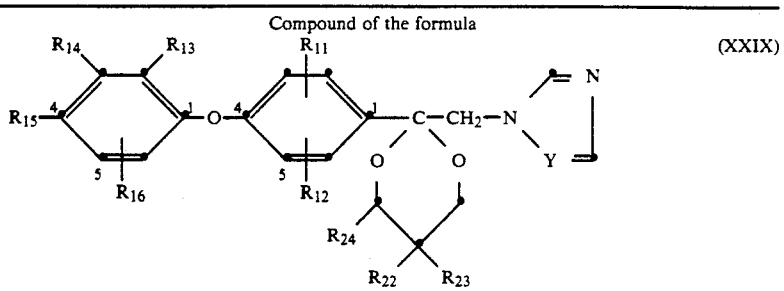
(XXIX)

including the isomeric forms:

| Compound | $R_{11}$ | $R_{12}$ | $R_{13}$ | $R_{14}$ | $R_{15}$ | $R_{16}$ | $R_{22}$ | $R_{23}$ | $R_{24}$ | Y | Salt |
|---|---|---|---|---|---|---|---|---|---|---|---|
| 9.1 | 2-Cl | H | H | H | H | H | H | $CH_3$ | H | N | — |
| 9.2 | 2-Cl | H | H | Cl | H | 6-Cl | $CH_3$ | $CH_3$ | H | CH | — |
| 9.3 | 2-Br | H | Br | H | H | H | $CH_3$ | $CH_3$ | H | N | — |
| 9.4 | 2-$CH_3$ | 6-$CH_3$ | H | H | H | H | $CH_3$ | $CH_3$ | H | N | $HNO_3$ |
| 9.5 | 2-Cl | 6-Cl | Cl | H | H | 6-Cl | $CH_3$ | $CH_3$ | $CH_3$ | N | $Mn(NO_3)_2$ |
| 9.6 | 2-Cl | 6-Cl | H | Cl | H | H | $CH_3$ | $CH_3$ | $CH_3$ | CH | — |
| 9.7 | 2-Cl | 5-Cl | H | H | Cl | H | $CH_3$ | $CH_3$ | H | N | — |
| 9.8 | 2-Cl | H | H | Cl | Cl | H | $CH_2$ | $C_2H_5$ | H | N | — |
| 9.9 | 2-Cl | H | Cl | H | H | H | $CH_3$ | $C_2H_5$ | H | N | $CuCl_2$ |
| 9.10 | 3-Cl | 5-Cl | Cl | H | H | 6-Cl | $CH_3$ | $C_2H_5$ | $CH_3$ | CH | $(COOH)_2$ |
| 9.11 | 2-Cl | 6-Cl | H | H | Cl | H | $C_2H_5$ | $C_2H_5$ | H | N | $HNO_3$ |
| 9.12 | 3-$CH_3$ | 5-$CH_3$ | H | H | H | H | $C_2H_5$ | $C_2H_5$ | H | N | — |
| 9.13 | 2-$CH_3$ | H | $CH_3$ | $CH_3$ | H | H | $C_2H_5$ | $C_2H_5$ | H | CH | HCl |
| 9.14 | 2-Cl | H | H | $CH_3$ | H | H | $C_2H_5$ | $C_2H_5$ | H | CH | $FeCl_3$ |
| 9.15 | 2-Cl | 5-Cl | Cl | H | H | H | $C_2H_5$ | $C_2H_5$ | H | CH | — |
| 9.16 | 2-Cl | H | Cl | Cl | Cl | 5-Cl | H | $C_2H_5$ | H | N | — |
| 9.17 | 2-Cl | H | H | Cl | Cl | H | H | $C_2H_5$ | H | N | $HNO_3$ |
| 9.18 | 2-$CH_3$ | 5-$CH_3$ | $CH_3$ | H | H | 6-$CH_3$ | H | $C_2H_5$ | H | CH | — |
| 9.19 | 2-$CH_3$ | 6-$CH_3$ | H | H | $CH_3$ | H | H | $C_3H_7$-n | H | N | $CuCl_2$ |
| 9.20 | 2-Cl | 6-Cl | H | H | $CH_3$ | H | H | $C_3H_7$-n | H | CH | — |
| 9.21 | 3-$NO_2$ | H | H | H | Cl | H | H | H | $CH_3$ | N | — |
| 9.22 | H | H | Cl | H | Cl | 6-$CH_3$ | $CH_3$ | $CH_3$ | H | N | — |
| 9.23 | H | H | $CH_3$ | H | Br | 6-Cl | $CH_3$ | $CH_3$ | $C_3H_7$-n | CH | — |
| 9.24 | H | H | $CH_3$ | H | Br | 6-Cl | $CH_3$ | $C_2H_5$ | H | N | — |

TABLE 10

Compounds of the formula

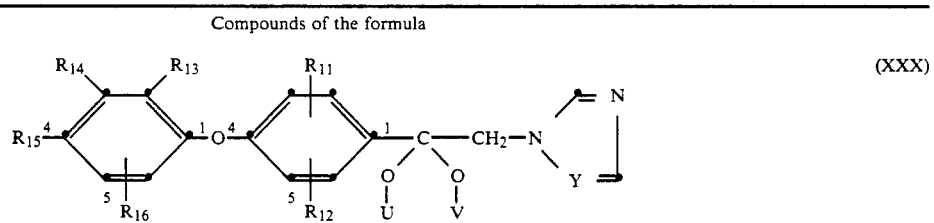
(XXX)

including the isomeric forms:

| Compound | $R_{11}$ | $R_{12}$ | $R_{13}$ | $R_{14}$ | $R_{15}$ | $R_{16}$ | Y | U | V | Salt | Physical data (°C.) |
|---|---|---|---|---|---|---|---|---|---|---|---|
| 10.1 | H | H | Cl | H | Cl | H | N | $CH_3$ | $CH_3$ | — | |
| 10.2 | H | H | Cl | H | Cl | H | N | $CH_3$ | $CH_3$ | $Mn(NO_3)_2$ | |
| 10.3 | H | H | $CH_3$ | H | $CH_3$ | H | CH | $CH_3$ | $C_2H_5$ | — | |
| 10.4 | H | H | $CH_3$ | H | $CH_3$ | 5-$CH_3$ | N | $C_2H_5$ | $C_2H_5$ | — | |
| 10.5 | H | H | H | Cl | H | 5-Cl | N | $C_4H_9$-n | $C_4H_9$-n | — | |
| 10.6 | H | H | H | Cl | H | 6-Cl | N | $C_3H_7$-i | $C_3H_7$-i | $CuCl_2$ | |
| 10.7 | H | H | H | H | H | H | N | $CH_3$ | $CH_3$ | — | m.p. 59–60° |
| 10.8 | H | H | H | H | F | H | CH | $CH_3$ | $CH_3$ | — | |
| 10.9 | H | H | H | H | H | H | N | $C_3H_7$-n | $C_3H_7$-n | $(COOH)_2$ | |
| 10.10 | 2-Cl | H | H | H | Cl | H | N | $CH_3$ | $CH_3$ | — | |
| 10.11 | 2-Cl | 6-Cl | H | H | H | H | N | $CH_3$ | $CH_3$ | — | |
| 10.12 | 3-Cl | H | H | H | H | H | N | $C_2H_5$ | $C_2H_5$ | — | |
| 10.13 | 2-Cl | 6-Cl | H | H | Cl | H | N | $C_8H_{17}$-n | $C_8H_{17}$-n | — | |
| 10.14 | 2-$CH_3$ | H | H | $CH_3$ | H | H | CH | $C_2H_5$ | $C_2H_5$ | HCl | |
| 10.15 | 2-$CH_3$ | 6-$CH_3$ | $CH_3$ | H | H | H | N | $C_3H_7$-i | $C_3H_7$-i | — | |
| 10.16 | 2-$CH_3$ | H | $CH_3$ | $CH_3$ | H | H | N | $C_5H_{11}$-n | $C_5H_{11}$-n | — | |
| 10.17 | 2-Cl | 5-Cl | Cl | H | H | 6-Cl | N | $CH_3$ | $CH_3$ | — | |
| 10.18 | 2-Cl | 5-Cl | H | H | Cl | H | N | $C_4H_9$-s | $C_4H_9$-s | — | |
| 10.19 | 2-Cl | 6-Cl | Cl | Cl | Cl | 6-Cl | CH | $CH_3$ | $CH_3$ | — | |
| 10.20 | 2-Cl | H | (CH=CH)$_2$ | | H | H | N | $CH_3$ | $CH_3$ | — | |
| 10.21 | 2-$CH_3$ | H | (CH=CH)$_2$ | | H | H | N | $CH_3$ | $C_3H_7$-i | — | |
| 10.22 | H | H | H | H | H | H | CH | $CH_3$ | $CH_3$ | — | |
| 10.23 | H | H | H | H | H | H | CH | $C_2H_5$ | $C_2H_5$ | — | |

TABLE 10-continued

Compounds of the formula

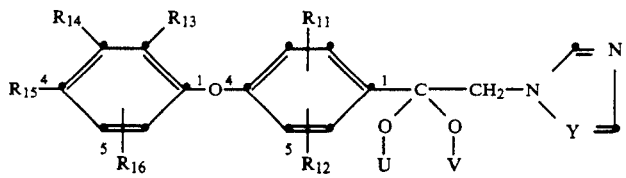

(XXX)

including the isomeric forms:

| Compound | R11 | R12 | R13 | R14 | R15 | R16 | Y | U | V | Salt | Physical data (°C.) |
|---|---|---|---|---|---|---|---|---|---|---|---|
| 10.24 | H | H | H | H | H | H | CH | $C_4H_9$-n | $C_4H_9$-n | — | |
| 10.25 | H | H | H | H | H | H | CH | $(CH_2)_2OCH_3$ | $(CH_2)_2OCH_3$ | — | |
| 10.26 | H | H | H | H | H | H | CH | $(CH_2)_2OC_2H_5$ | $(CH_2)_2OC_2H_5$ | — | |
| 10.27 | H | H | H | H | H | H | CH | $C_8H_{17}$-n | $C_8H_{17}$-n | — | |
| 10.28 | H | H | H | H | H | H | N | $(CH_2)_2OCH_3$ | $(CH_2)_2OCH_3$ | — | |
| 10.29 | 2-$CH_3$ | H | H | H | H | H | CH | $CH_3$ | $CH_3$ | — | |
| 10.30 | 2-$CH_3$ | H | H | H | H | H | N | $(CH_2)_2OCH_3$ | $(CH_2)_2OCH_3$ | — | |
| 10.31 | 2-Cl | H | H | H | H | H | CH | $(CH_2)_2OCH_3$ | $(CH_2)_2OCH_3$ | — | |
| 10.32 | 2-$CH_3$ | H | H | H | H | H | N | $CH_3$ | $CH_3$ | — | |
| 10.33 | 2-Cl | H | H | H | H | H | CH | $CH_3$ | $CH_3$ | — | |
| 10.34 | 2-Cl | H | H | H | H | H | N | $(CH_2)_2OCH_3$ | $(CH_2)_2OCH_3$ | — | |
| 10.35 | 2-Br | H | H | H | H | H | CH | $CH_3$ | $CH_3$ | — | |
| 10.36 | 2-Br | H | H | H | H | H | N | $C_2H_5$ | $C_2H_5$ | — | |
| 10.37 | 3-$NO_2$ | H | H | H | H | H | CH | $C_2H_5$ | $C_2H_5$ | — | |
| 10.38 | 2-Br | H | H | H | H | H | N | $(CH_2)_2OCH_3$ | $(CH_2)_2OCH_3$ | — | |
| 10.39 | 3-$CH_3$ | H | H | H | H | H | CH | $CH_3$ | $CH_3$ | — | |
| 10.40 | H | H | Cl | H | H | H | CH | $CH_3$ | $CH_3$ | — | |
| 10.41 | H | H | Cl | H | H | H | CH | $(CH_2)_2OCH_3$ | $(CH_2)_2OCH_3$ | — | |
| 10.42 | H | H | Cl | H | H | H | CH | $C_4H_9$-n | $C_4H_9$-n | — | |
| 10.43 | H | H | Cl | H | H | H | N | $(CH_2)_2OCH_3$ | $(CH_2)_2OCH_3$ | — | |
| 10.44 | H | H | H | Cl | H | H | CH | $CH_3$ | $CH_3$ | — | |
| 10.45 | H | H | H | Cl | H | H | CH | $C_4H_9$-n | $C_4H_9$-n | — | |
| 10.46 | H | H | H | Cl | H | H | CH | $C_8H_{17}$-n | $C_8H_{17}$-n | — | |
| 10.47 | H | H | H | Cl | H | H | N | $C_4H_9$-n | $C_4H_9$-n | — | |
| 10.48 | H | H | H | Cl | H | H | CH | $C_2H_5$ | $C_2H_5$ | — | |
| 10.49 | H | H | H | Cl | H | H | CH | $(CH_2)_2OCH_3$ | $(CH_2)_2OCH_3$ | — | |
| 10.50 | H | H | H | Cl | H | H | CH | $(CH_2)_2OC_2H_5$ | $(CH_2)_2OC_2H_5$ | — | |
| 10.51 | H | H | H | H | Cl | H | CH | $CH_3$ | $CH_3$ | — | |
| 10.52 | H | H | H | H | Cl | H | CH | $C_4H_9$-n | $C_4H_9$-n | — | |
| 10.53 | H | H | H | H | Cl | H | CH | $(CH_2)_2OCH_3$ | $(CH_2)_2OCH_3$ | — | |
| 10.54 | H | H | H | H | Cl | H | CH | $C_2H_5$ | $C_2H_5$ | — | |
| 10.55 | H | H | H | H | Cl | H | CH | $C_2H_4Cl$ | $C_2H_4Cl$ | — | |
| 10.56 | H | H | H | H | Cl | H | CH | $(CH_2)_2OC_2H_5$ | $(CH_2)_2OC_2H_5$ | — | |
| 10.57 | H | H | H | H | Cl | H | N | $C_2H_5$ | $C_2H_5$ | — | |
| 10.58 | H | H | H | H | Cl | H | N | $CH_3$ | $CH_3$ | — | |
| 10.59 | H | H | H | H | Cl | H | N | $(CH_2)_2OCH_3$ | $(CH_2)_2OCH_3$ | — | |
| 10.60 | H | H | H | H | Br | H | CH | $(CH_2)_2OCH_3$ | $(CH_2)_2OCH_3$ | — | |
| 10.61 | H | H | H | H | Br | H | CH | $CH_3$ | $CH_3$ | — | |
| 10.62 | H | H | $CH_3$ | H | H | H | CH | $CH_3$ | $CH_3$ | — | |
| 10.63 | H | H | $NO_2$ | H | H | H | CH | $CH_3$ | $CH_3$ | — | |
| 10.64 | H | H | H | $CF_3$ | H | H | CH | $CH_3$ | $CH_3$ | — | |
| 10.65 | H | H | H | $CF_3$ | H | H | CH | $(CH_2)_2OCH_3$ | $(CH_2)_2OCH_3$ | — | |
| 10.66 | H | H | Cl | Cl | H | H | CH | $CH_3$ | $CH_3$ | — | |
| 10.67 | H | H | Cl | H | Cl | H | CH | $C_2H_5$ | $C_2H_5$ | — | |
| 10.68 | H | H | Cl | H | H | 5-Cl | N | $C_2H_5$ | $C_2H_5$ | — | |
| 10.69 | H | H | Cl | H | H | 5-Cl | CH | $CH_3$ | $CH_3$ | — | |
| 10.70 | H | H | Cl | H | H | 6-Cl | CH | $C_4H_9$-n | $C_4H_9$-n | — | |
| 10.71 | H | H | H | Cl | Cl | H | N | $CH_3$ | $CH_3$ | — | |
| 10.72 | H | H | H | Cl | H | 5-Cl | CH | $CH_3$ | $CH_3$ | — | |
| 10.73 | H | H | H | Cl | Cl | H | CH | $CH_3$ | $CH_3$ | — | |
| 10.74 | H | H | Br | H | Br | H | CH | $CH_3$ | $CH_3$ | — | |
| 10.75 | H | H | Cl | H | Br | H | CH | $C_2H_5$ | $C_2H_5$ | — | |
| 10.76 | H | H | $CH_3$ | $CH_3$ | H | H | CH | $CH_3$ | $CH_3$ | — | |
| 10.77 | H | H | $CH_3$ | H | H | 5-$CH_3$ | CH | $C_2H_5$ | $C_2H_5$ | — | |
| 10.78 | H | H | $C_4H_9$-t | H | $C_4H_9$-t | H | CH | $C_2H_5$ | $C_2H_5$ | — | |
| 10.79 | H | H | H | $CH_3$ | H | 5-$CH_3$ | CH | $(CH_2)_2OCH_3$ | $(CH_2)_2OCH_3$ | | |
| 10.80 | H | H | $C_3H_7$-i | H | H | 5-$CH_3$ | CH | $CH_3$ | $CH_3$ | — | |
| 10.81 | H | H | Cl | H | Cl | 5-Cl | CH | $C_2H_5$ | $C_2H_5$ | — | |
| 10.82 | H | H | Cl | Cl | Cl | H | CH | $(CH_2)_2OCH_3$ | $(CH_2)_2OCH_3$ | — | |
| 10.83 | H | H | Cl | Cl | H | 5-Cl | CH | $C_2H_5$ | $C_2H_5$ | — | |
| 10.84 | H | H | Br | H | Br | 6-Br | CH | $(CH_2)_2OC_2H_5$ | $(CH_2)_2OC_2H_5$ | — | |
| 10.85 | H | H | $CH_3$ | H | Cl | H | CH | $CH_3$ | $CH_3$ | — | |
| 10.86 | H | H | H | $CH_3$ | Cl | H | CH | $CH_3$ | $CH_3$ | — | |
| 10.87 | H | H | H | $CH_3$ | Cl | H | N | $(CH_2)_2OCH_3$ | $(CH_2)_2OCH_3$ | — | |
| 10.88 | H | H | $C_4H_9$-t | H | Cl | H | CH | $CH_3$ | $CH_3$ | — | |
| 10.89 | H | H | $C_4H_9$-t | H | Cl | H | N | $C_2H_4Cl$ | $C_2H_4Cl$ | — | |
| 10.90 | H | H | Br | H | $CH_3$ | H | CH | $C_8H_{17}$-n | $C_8H_{17}$-n | — | |
| 10.91 | H | H | $NO_2$ | H | $CF_3$ | H | CH | $CH_3$ | $CH_3$ | — | |
| 10.92 | H | H | H | $CH_3$ | Cl | 5-$CH_3$ | CH | $C_7H_{18}$-n | $C_7H_{18}$-n | — | |

TABLE 10-continued

Compounds of the formula

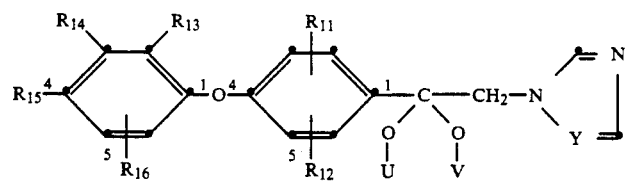
(XXX)

including the isomeric forms:

| Compound | $R_{11}$ | $R_{12}$ | $R_{13}$ | $R_{14}$ | $R_{15}$ | $R_{16}$ | Y | U | V | Salt | Physical data (°C.) |
|---|---|---|---|---|---|---|---|---|---|---|---|
| 10.93 | H | H | $CF_3$ | H | $NO_2$ | H | CH | $CH_3$ | $CH_3$ | — | |
| 10.94 | H | H | H | $CH_3$ | Cl | 5-$CH_3$ | CH | $C_2H_4Cl$ | $C_2H_4Cl$ | — | |
| 10.95 | H | H | $CF_3$ | H | $NO_2$ | 6-$CF_3$ | CH | $CH_3$ | $CH_3$ | — | |
| 10.96 | H | H | $CF_3$ | H | $NO_2$ | 6-$CF_3$ | N | $C_2H_5$ | $C_2H_5$ | — | |
| 10.97 | H | H | $CF_3$ | H | $NO_2$ | 6-$NO_2$ | CH | $C_2H_5$ | $C_2H_5$ | — | |
| 10.98 | H | H | Br | H | $CH_3$ | H | CH | $C_2H_4Cl$ | $C_2H_4Cl$ | — | |
| 10.99 | H | H | H | H | F | H | CH | $C_4H_9$-n | $C_4H_9$-n | — | |
| 10.100 | H | H | H | H | F | H | CH | $(CH_2)_2OCH_3$ | $(CH_2)_2OCH_3$ | — | |
| 10.101 | H | H | H | H | F | H | CH | $C_2H_4Cl$ | $C_2H_4Cl$ | — | |
| 10.102 | H | H | H | H | F | H | CH | $C_2H_5$ | $C_2H_5$ | — | |
| 10.103 | H | H | H | H | F | H | N | $(CH_2)_2OCH_3$ | $(CH_2)_2OCH_3$ | — | |

TABLE 11

Compounds of the formula

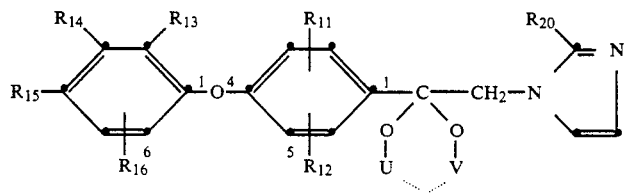
(XXXI)

| Compound | $R_{11}$ | $R_{12}$ | $R_{13}$ | $R_{14}$ | $R_{15}$ | $R_{16}$ | U...V | $R_{20}$ | Salt | Physical data (°C.) |
|---|---|---|---|---|---|---|---|---|---|---|
| 11.1 | H | H | H | H | H | H | $C_2H_5$ | $CH_3$ | $HNO_3$ | |
| 11.2 | H | H | H | H | Cl | H | $C_2H_5$ | $CH_3$ | — | viscous mass, $n_D^{23}$ 1.5721 |
| 11.3 | H | H | H | H | H | H | $CH_3$ | $CH_3$ | — | viscous mass, $n_D^{22.5}$ 1.5634 |
| 11.4 | H | H | H | Cl | Cl | H | $CH_2OH$ | $CH_3$ | — | |
| 11.5 | H | H | H | Cl | Cl | H | $C_2H_5$ | $CH_3$ | — | viscous mass |
| 11.6 | H | H | H | Cl | Cl | H | $C_2H_5$ | $C_2H_5$ | — | |
| 11.7 | 2-$CH_3$ | H | H | H | H | H | $C_2H_5$ | $CH_3$ | — | viscous mass, $n_D^{22.5}$ 1.5640 |

TABLE 11-continued

Compounds of the formula

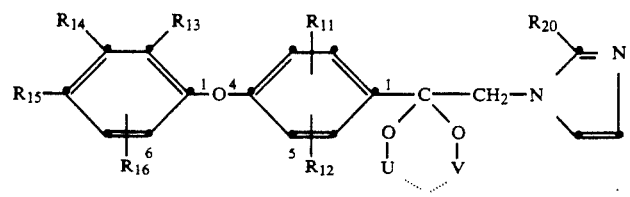

(XXXI)

| Compound | $R_{11}$ | $R_{12}$ | $R_{13}$ | $R_{14}$ | $R_{15}$ | $R_{16}$ | U...V | $R_{20}$ | Salt | Physical data (°C.) |
|---|---|---|---|---|---|---|---|---|---|---|
| 11.8 | 2-CH$_3$ | H | H | H | Cl | H | CH$_3$ | CH$_3$ | — | viscous mass, $n_D^{21}$ 1.5767 |
| 11.9 | 2-CH$_3$ | H | H | H | Cl | H | C$_2$H$_5$ | CH$_3$ | — | oil, $n_D^{21}$ 1.5711 |
| 11.10 | H | H | H | Cl | H | H | C$_2$H$_5$ | CH$_3$ | — | viscous mass, $n_D^{22}$ 1.5685 |
| 11.11 | 2-CH$_3$ | H | H | H | F | H | CH$_3$ | CH$_3$ | — | |
| 11.12 | H | H | H | H | H | H | CH$_2$OH | CH$_3$ | — | |
| 11.13 | H | H | H | H | Cl | H | CH$_2$OCH$_3$ | CH$_3$ | — | |
| 11.14 | H | H | H | H | H | H | CH$_3$ | CH$_3$ | — | |
| 11.15 | 2-Cl | H | H | H | H | H | C$_2$H$_5$ | CH$_3$ | — | oil, $n_D^{21}$ 1.5708 |
| 11.16 | 2-Cl | H | H | H | Cl | H | C$_2$H$_5$ | CH$_3$ | — | |
| 11.17 | H | H | H | H | H | H | | CH$_3$ | — | |
| 11.18 | H | H | H | H | F | H | | CH$_3$ | — | |
| 11.19 | 2-CH$_3$ | 6-CH$_3$ | H | H | H | H | C$_2$H$_5$ | CH$_3$ | — | |
| 11.20 | H | H | CH$_3$ | H | Cl | H | C$_2$H$_5$ | CH$_3$ | — | |

TABLE 11-continued

Compounds of the formula

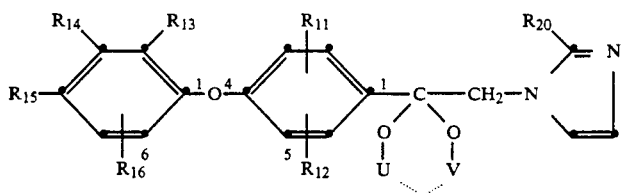

(XXXI)

| Compound | $R_{11}$ | $R_{12}$ | $R_{13}$ | $R_{14}$ | $R_{15}$ | $R_{16}$ | U...V | $R_{20}$ | Salt | Physical data (°C.) |
|---|---|---|---|---|---|---|---|---|---|---|
| 11.21 | H | H | H | H | Cl | H | $CH_3$, $CH_3$ | $CH_3$ | — | |
| 11.22 | H | H | H | H | F | H | $CH_2OH$ | $CH_3$ | — | |
| 11.23 | 2-$CH_3$ | H | H | H | F | H | $C_2H_5$ | $CH_3$ | — | |
| 11.24 | H | H | H | H | Cl | H |  | $CH_3$ | — | m.p. 88–90° |
| 11.25 | 2-$CH_3$ | H | H | H | F | H |  | $CH_3$ | — | |
| 11.26 | 2-$CH_3$ | H | H | H | Br | H | $CH_3$ | $CH_3$ | — | |
| 11.27 | 2-$CH_3$ | H | H | H | Cl | H | $CH_3$ | $CH_3$ | $HNO_3$ | m.p. 181–183 |
| 11.28 | H | H | H | $CH_3$ | Cl | H | $CH_2OCH_3$ | $CH_3$ | — | oil, $n_D^{22}$ 1.5599 |
| 11.29 | H | H | H | H | H | H | $C_3H_7$-n | $CH_3$ | — | oil, $n_D^{22,5}$ 1.5565 |
| 11.30 | H | H | Cl | H | Cl | H | $C_2H_5$ | $CH_3$ | — | oil, $n_D^{22,5}$ 1.5732 |
| 11.31 | H | H | H | H | Cl | H | $CH_2OH$ | $CH_3$ | — | |
| 11.32 | 2-Cl | H | H | H | F | H | $C_2H_5$ | $CH_3$ | — | |

TABLE 11-continued

Compounds of the formula

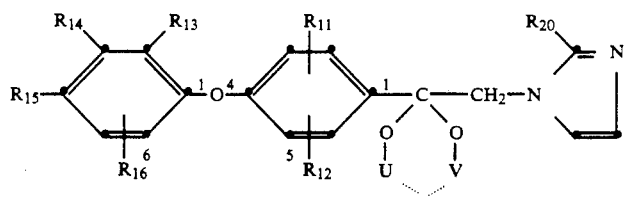

(XXXI)

| Compound | $R_{11}$ | $R_{12}$ | $R_{13}$ | $R_{14}$ | $R_{15}$ | $R_{16}$ | U...V | $R_{20}$ | Salt | Physical data (°C.) |
|---|---|---|---|---|---|---|---|---|---|---|
| 11.33 | H | H | H | Cl | H | H | CH$_2$OH | CH$_3$ | — | |
| 11.34 | 2-CH$_3$ | H | H | Cl | H | H | | CH$_3$ | — | |
| 11.35 | 2-CH$_3$ | 5-CH$_3$ | H | Cl | H | H | CH$_2$OH | CH$_3$ | — | |
| 11.36 | 2-CH$_3$ | H | H | H | H | H | CH$_2$OH | CH$_3$ | — | |
| 11.37 | 2-CH$_3$ | 5-CH$_3$ | H | H | H | H | CH$_2$OH | CH$_3$ | — | |
| 11.38 | 2-CH$_3$ | 5-CH$_3$ | H | H | H | H | CH$_3$ | CH$_3$ | — | |
| 11.39 | 2-CH$_3$ | 5-CH$_3$ | H | H | Cl | H | C$_3$H$_7$-n | C$_2$H$_5$ | HNO$_3$ | |
| 11.40 | 2-C$_2$H$_5$ | H | H | H | Cl | H | C$_2$H$_5$ | CH$_3$ | — | $n_D^{24.5}$ 1.5678 |
| 11.41 | 2-CH$_3$ | H | H | H | H | H | CH$_3$ | CH$_3$ | HNO$_3$ | m.p. 124–126° |
| 11.42 | H | H | H | Cl | H | H | CH$_2$OCH$_3$ | CH$_3$ | — | $n_D^{22}$ 1.5682 |

Formulation Examples for Agrochemical Compositions Containing Liquid Active Ingredients of the Formula I
(Throughout, Percentages are by Weight)

| 13. Emulsifiable concentrates | a) | b) | c) |
|---|---|---|---|
| compound of Tables 1 to 11 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexane | — | 15% | 20% |
| xylene mixture | 65% | 25% | 20% |

Emulsions of any required concentration can be produced from such concentrates by dilution with water.

| 14. Solutions | a) | b) | c) | d) |
|---|---|---|---|---|
| compound of Tables 1 to 11 | 80% | 10% | 5% | 95% |
| ethylene glycol monomethyl ether | 20% | — | — | — |
| polyethylene glycol 400 | — | 70% | — | — |
| N-methyl-2-pyrrolidone | — | 20% | — | — |
| epoxidised coconut oil | — | — | 1% | 5% |
| ligroin (boiling range 160-190° C.) | — | — | 94% | — |

These solutions are suitable for application in the form of microdrops.

| 15. Granulates | a) | b) |
|---|---|---|
| compound of Tables 1 to 11 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 16. Dusts | a) | b) |
|---|---|---|
| compound of Tables 1 to 11 | 2% | 5% |
| highly dispersed silicic acid | 1% | 5% |
| talcum | 97% | — |
| kaolin | — | 90% |

Ready for use dusts are obtained by intimately mixing the carriers with the active ingredient.

Formulation Examples for Agrochemical Compositions Containing Solid Active Ingredients of the Formula I (Throughout, Percentages are by Weight)

| 17. Wettable powders | a) | b) | c) |
|---|---|---|---|
| compound of Tables 1 to 11 | 25% | 50% | 75% |
| sodium lignosulfonate | 5% | 5% | — |
| sodium laurylsulfate | 3% | — | 5% |
| sodium diisobutylnaphthalene-sulfonate | — | 5% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 18. Emulsifiable concentrates | |
|---|---|
| compound of Tables 1 to 11 | 10% |
| octylphenol polyethylene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 20% |
| xylene mixture | 50% |
| coconut oil | 10% |

Emulsions of any required concentration can be obtained from this concentrate by dilution with water.

| 19. Dusts | a) | b) |
|---|---|---|
| compound of Tables 1 to 11 | 5% | 8% |
| talcum | 95% | — |
| kaolin | — | 92% |

Ready for use dusts are obtained by mixing the active ingredient with the carriers, and grinding the mixture in a suitable mill.

| 20. Extruder granulate | |
|---|---|
| compound of Tables 1 to 11 | 10% |
| sodium lignosulfonate | 2% |
| carboxymethylcellulose | 1% |
| kaolin | 87%. |

The active ingredient is mixed and ground with the adjuvants, and the mixture is subsequently moistened with water. The mixture is extruded and then dried in a stream of air.

| 21. Coated granulate | |
|---|---|
| compound of Tables 1 to 11 | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 22. Suspension concentrate | |
|---|---|
| compound of Tables 1 to 11 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32%. |

The finely ground active ingredient is intimately mixed with the adjuvants, giving a suspension concentrate from which suspensions of any desired concentration can be obtained by dilution with water.

Formulation Examples for Pharmaceutical Preparations

23. Ointments

An ointment containing 5% of 2-[p-(4-chlorophenoxy)phenyl]-2-(1-imidazolylmethyl)-4-ethyl-dioxolane may be prepared as follows:

| Composition | |
|---|---|
| Active ingredient | 5.0% |
| white petroleum jelly | 45.0% |
| liquid paraffin | 19.6% |
| cetyl alcohol | 5.0% |
| beeswax | 5.0% |
| sorbitan sesquioleate | 5.0% |
| p-hydroxybenzoate | 0.2% |
| demineralised water to make up | 100.0% |

The fatty substance and emulsifiers are melted together. The preservative is dissolved in water and the solution is emulsified into the fatty melt at elevated temperature. After cooling, a suspension of the active ingredient in part of the fatty melt is incorporated into the emulsion.

24. Cream

A cream containing 10% of 2-[p-(chlorophenoxy)-phenyl]-2-(1-imidazolylmethyl)-4-ethyl-1,3-dioxolane may be prepared as follows:

| Composition | |
| --- | --- |
| active ingredient | 10.0% |
| isopropyl palmitate | 8.0% |
| cetyl palmitate | 1.5% |
| silicone oil 100 | 0.5% |
| sorbitan monostearate | 3.0% |
| polysorbate 60 | 3.5% |
| 1,2-propylene glycol PH | 20.0% |
| acrylic acid polymer | 0.5% |
| triethanolamine | 0.7% |
| demineralised water to make up | 100.0% |

The acrylic acid polymer is suspended in a mixture of demineralised water and 1,2-propylene glycol. Triethanolamine is then stirred in to give a mucilage. A mixture of isopropyl palmitate, cetyl palmitate, silicone oil, sorbitan monostearate and polysorbate is heated to about 750° C. and then stirred into the mucilage, which is also heated to about 75° C. After it has cooled to room temperature, the cream base is used to prepare a concentrate with the active ingredient. This concentrate is homogenised using a continuous homogeniser, and then added in portions to the base.

A cream containing 5% of 2-[p-(chlorophenoxy)-phenyl]-2-(1-imidazolylmethyl)-4-ethyl-1,3-dioxolane may be prepared as follows:

| Composition | |
| --- | --- |
| active ingredient | 5.0% |
| cetyl palmitate PH | 2.0% |
| cetyl alcohol PH | 2.0% |
| triglyceride mixture of saturated medium fatty acids | 5.0% |
| stearic acid | 3.0% |
| glycerol stearate PH | 4.0% |
| Cetomacrogol 1000 | 1.0% |
| microcrystalline cellulose | 0.5% |
| 1,2-propylene glycol (dist.) | 20.0% |
| demineralised water to make up | 100.0% |

The cetyl alcohol, cetal palmitate, triglyceride mixture, stearic acid and glycerol stearate are melted together. The microcrystalline cellulose is dispersed in a portion of the water. The Cetomacrogol is dissolved in the remainder of the water and both the propylene glycol and the mucilage are blended therewith. The fatty phase is then stirred into the aqueous phase and the mix is stirred cold. Finally, the active ingredient is milled with a portion of the base and then incorporated in the rest of the cream.

25. Hydrogels

A transparent hydrogel containing 5% of 2-[p-(chlorophenoxy)-phenyl]-2-(1-imidazolylmethyl)-4-ethyldioxolane as follows:

| Composition | |
| --- | --- |
| active ingredient | 5% |
| propylene glycol | 10-20% |
| isopropanol | 20% |
| hydroxypropyl methyl cellulose | 2% |
| water to make up | 100% |

The hydroxypropyl methyl cellulose is expanded in water. The active ingredient is dissolved in a mixture of isopropanol and propylene glycol. The active ingredient solution is then blended with an expanded cellulose derivative and, if desired, perfume (0.1%) is added.

26. Foam sprays

A foam spray containing 1% of 2-[p-(chlorophenoxy)phenyl]-2(1-imidazolylmethyl)-4-ethyldioxolane may be prepared as follows:

| Composition | |
| --- | --- |
| active ingredient | 1.00% |
| cetyl alcohol PH | 1.70% |
| liquid paraffin (viscous) | 1.00% |
| isopropyl myristate | 2.00% |
| Cetamacrogol | 2.40% |
| sorbitan monostearate | 1.50% |
| 1,2-propylene glycol PH | 5.00% |
| methyl parabene | 0.18% |
| propyl parabene | 0.02% |
| Chemoderm 314 | 0.10% |
| demineralised water to make up | 100.00% |

The cetyl alcohol, liquid paraffin, isopropyl myristate, Cetomacrogol and sorbitan stearate are fused together. The methyl and propyl parabene are dissolved in hot water. The melt and the solution are then blended. A suspension of the active ingredient in propylene glycol is incorporated in the base. Chemoderm is then added and the composition is bulked with water to the final weight.

Filling 20 ml of the composition are filled into an aluminium dispenser. The dispenser is fitted with a pressure cap and filled with propellant gas under pressure.

27. Capsules

Gelatin capsules containing 200 mg of [p-(phenoxy)-phenyl]-2 [1-(1H-1,2,4-triazolyl)methyl]-1,3 -dioxane as active ingredient may be prepared as follows:

| Composition (for 1000 capsules) | |
| --- | --- |
| active ingredient | 100 g |
| lactose (ground) | 100 g |

The active ingredient and the lactose (micronised) are well mixed. The resultant powder is sieved and packed into gelatin capsules of 0.2 g.

28. Tablets

Tablets containing 25 mg of active ingredient, e.g. 2-[p-(phenoxy)phenyl]-2-[1-(1H-1,2,4-triazolyl)methyl]-1,3-dioxane, may be prepared as follows:

| Composition (for 1000 tablets) | |
| --- | --- |
| active ingredient | 25.0 g |
| lactose | 100.7 g |

-continued

| Composition (for 1000 tablets) | |
|---|---|
| corn starch | 7.5 g |
| polyethylene glycol 6000 | 5.0 g |
| talcum | 5.0 g |
| magnesium stearate | 1.8 g |
| demineralised water | q.s. |

Preparation

All the solid ingredients are first passed through a sieve having a mesh size of 0.6 mm. Then the active ingredient, the lactose, talcum, magnesium stearate and half of the starch are blended together. The other half of the starch is suspended in 40 ml of water and this suspension is added to a boiling solution of the polyethylene glycol in 1000 ml of water and the mixture is granulated, if necessary with the addition of water. The granulate is dried overnight at 35° C., passed through a 1.2 mm sieve and compressed to biconcave tablets of about 6 mm diameter.

Tablets containing 75 mg of active ingredient, e.g. 2-[p-(phenoxy)phenyl]-2-[1-(1H-1,2,4 -triazolyl)methyl]-1,3-dioxane, may be prepared as follows:

| Composition (for 1000 tablets) | |
|---|---|
| active ingredient | 75.0 g |
| lactose | 100.7 g |
| corn starch | 7.5 g |
| polyethylene glycol 6000 | 5.0 g |
| talcum | 5.0 g |
| magnesium stearate | 1.8 g |
| demineralised water | q.s. |

Preparation

All the solid ingredients are first passed through a sieve having a mesh size of 0.6 mm. Then the active ingredient, the lactose, talcum, magnesium stearate and half of the starch are blended together. The other half of the starch is suspended in 40 ml of water and this suspension is added to a boiling solution of the polyethylene glycol in 100 ml of water and the mixture is granulated, if necessary with the addition of water. The granulate is dried overnight at 350° C., passed through a 1.2 mm sieve and compressed to biconcave tablets of about 6 mm diameter.

Pharmaceutical preparations containing another compound of Tables 1 to 11 may laso be prepared in analogous manner.

BIOLOGICAL EXAMPLES

Example 29

Action Against *Puccinis Graminis* on Wheat a) Residual-Protective Action

Wheat plants are treated 6 days after sowing with a spray mixture prepared from a wettable powder formulation of the active ingredient (0,006%). After 24 hours the treated plants are infected with a uredospore suspension of the funaus. The infected plants are incubated for 48 hours at 95-100% relative humidity and about 20° C. and then stood in a greenhouse at about 22° C. Evaluation of rust pustule development is made 12 days after infection.

b) Systemic Action

Wheat plants are treated 5 days after sowing with a spray mixture prepared from a wettable powder formulation of the active ingredient (0.06% based on the volume of the soil). After 48 hours the treated plants are infected with a uredospore suspension of the fungus. The plants are then incubated for 48 hours at 95-100% relative humidity and about 20° C. and then stood in a greenhouse at about 22° C. Evaluation of rust pustule development is made 12 days after infection.

Compounds of Tables 1 to 11 are very effective against Puccinia fungi. Puccinia infestation is 100 % on untreated, infected control plants. Residual-protective treatment with compounds 1.9, 1.17, 1.24, 1.26, 2.17, 3.1, 3.2, 3.6 to 3.8, 3.12, 3.26, 3.51, 3.52, 3.54, 3.55, 3.70, 3.75, 3.78, 3.83, 3.103, 3.85, 3.86, 3.127, 3.133, 3.155, 3.156, 3.160, 3.162, 3.164, 1.168, 3.171, 3.172, 3.176, 3.177, 3.193, 3.212, 3.213, 3.220, 3.226, 3.227, 3.231 to 3.234, 3.260, 3.263, 3.267, 3.274, 3.279, 3.287, 3.292, 3.311, 3.314, 3.340, 3.348, 3.373, 3.376, 4.2, 4.15, 4.231 4.50, 4.55, 4.57, 4.64, 4.66, 4.70, 4.77, 4.78, 4.81, 4.89 to 4.94, 4.113, 4.116, 4.137, 5.13, 5.14. 5.36, 5.40, 5.42, 5.70, 5.71, 5.73, 5.76, 5.78, 5.118, 6.8. 6.82, 7.7, 7.33, 8.66, 11.2, 11.8 und 11.27 among others, inhibit fungus attack to 0-5%. In addition, compounds 6.8 and 6.82 have a full systemic action (0% attack) even when diluted to a concentration of 0.006 %.

Example 30

Action Against *Cercospora Arachidicola* in Groundnut Plants

Groundnut plants 10-15 cm in height are sprayed with a spray mixture prepared from a wettable powder formulation of the active ingredient (concentration 0 002%) and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection, and is based on the number and size of the specks.

Compared with untreated and infected controls (number and size of the specks=100%), the plants treated with compounds of Tables 1 to 11 exhibit greatly reduced attack by Cercospora. For example, compounds 1.1, 1.4, 1.9, 1.14, 1.17, 1.24 to 1.27, 2.17, 3.1, 3.2, 3.6, 3.7, 3.11, 3.51, 3.52, 3.54, 3.55, 3.57, 3.78, 3.85, 3.86, 3.127, 3.133, 3.155, 3.156, 3.162, 3.171, 3.172, 3.176, 3.177, 3.212, 3.213, 3.220, 3.221, 3.226, 3.231, 3.232, 3.233, 3.234, 3.267, 3.292, 3.314, 3.348, 4.15, 4.23, 4.50, 4.57, 4.59, 4.66, 4.89 to 4.94, 4.113, 4.116, 4.137, 5.13, 5.14, 5.36, 5.40, 5.70, 5.71, 5.73, 5.75 to 5.78, 5.118, 6.1, 6.8, 7.33, 7.34, 8.72 and 11.2 inhibit the formation of specks in this test almost completely (0 to 5% attack).

Example 31

Action Against *Erysiphe Graminis* on Barley a) Residual Protective Action

Barley plants about 8 cm in height are sprayed with a spray mixture (0,002%) prepared from the active ingredient formulated as a wettable powder. The treated plants are dusted with conidia of the fungus after 3-4 hours. The infected barley plants are then stood in a greenhouse at about 22° C. The fungus attack is evaluated after 10 days.

b) Systemic Action

Barley plants about 8 cm in height are treated with a spray mixture (0.006%, based on the volume of the soil) prepared from the active ingredient formulated as wettable powder. Care is taken that the spray mixture does not come in contact with the parts of the plants above the soil. The treated plants are infected 48 hours later with a conidia suspension of the fungus. The infected barley plants are then stood in a greenhouse at about 22° C. and evaluation of fungus infestation is made after 10 days.

Compounds of the formula I have a good residual-protective action against Erysiphe fungi. Erysiphe infestation of untreated, infected control plants is 100%. Among others, compounds 1.1, 1.4, 1.9, 1.14, 1.17, 1.23 to 1.27, 2.17, 3.1, 3.2, 3.6 to 3.8, 3.11, 3.12, 3.26, 3.51, 3.52, 3.54, 3.55, 3.70, 3.75, 3.78, 3.85, 3.86, 3.103, 3.127, 3.133, 3.156, 3.160, 3.162, 3.164, 3.168, 3.171, 3.172, 3.174, 3.176, 3.177, 3.193, 3.212, 3.213, 3.220, 3.221, 3.226, 3.227, 3.231, 3.232 to 3.234, 3.263, 3.267, 3.274, 3.279, 3.287, 3.292, 3.311, 3.314, 3.340, 3.348, 3.378, 4.2, 4.15, 4.23, 4.50, 4.57, 4.59, 4.66, 4.77, 4.78, 4.81, 4.89 to 4.94, 4.113, 4.116, 5.13, 5.14, 5.36, 5.40, 5.70, 5.71, 5.73, 5.75 to 5.78, 5.106, 5.107, 5.118, 6.1, 6.8–6.17, 6.791 6.80, 6.82, 7.3, 7.7, 7.21, 7.33, 7.34, 8.66, 8.69, 8.72, 0.7, 11.2, 11.8 and 11.10 inhibit fungus attack to less than 5 %. Compounds 4.50 and 6.82 are also effective in soil treatment (systemic action) and when diluted to a concentration of 0.006%.

Example 32

Residual-Protective Action Against *Venturia Inaegualis* on Apple Shoots

Apple cuttings with 10–20 cm long fresh shoots are sprayed with a spray mixture prepared from a wettable powder formulation of the active ingredient (0.06%. After 24 hours the treated plants are infected with a conidia suspension of the fungus. The plants are the incubated for 5 days at 90–100 % relative humidity and stood in a greenhouse for a further 10 days at 20°–24° C. Scab infestation is evaluated 5 days after infection. Compounds 1.4, 1.9, 1.17, 1.24, 1.26, 2.17, 3.1, 3.6, 3.7, 3.11, 3.52, 3.55, 3.85, 3.86, 3.156, 3.160, 3.164, 3.172, 3.176, 3.177, 3.213, 3.221, 3.233, 3.314, 4.15, 4.23, 4.50, 4.59, 4.66, 4.78, 4.81, 4.89, 4.90 to 4.94, 4.113, 4.116, 5.13, 5.14, 5.36, 5.40, 5.70, 5.73, 5.75, 5.76, 6.1, 6.8, 10.7, 11.2 and 11.29 and others inhibit infestation to less than 10 %. Venturia infestation is 100 % on untreated, infected shoots.

Example 33

Action Against *Botrytis Cinerea* on Beans a) Residual Protective Action

Bean plants about 10 cm in height are sprayed with a spray mixture(0,002%) prepared from the active ingredient formulated as wettable powder. After 48 hours, the treated plants are infected with a conidia suspension of the fungus. The infected plants are incubated for 3 days at 95–100%. relative humidity and 21° C., and evaluation of the fungus attack is then made. Compounds of Tables 1 to 11 very strongly inhibit fungus infestation in many cases. At a concentration of 0,002%, compounds 1.1, 1.4, 1.9, 1.17, 3.6, 3.7, 3.12, 3.51, 3.55, 3.86, 3.226, 3.231, 3.267, 3.311, 4.15, 4.50, 4.59, 4.66, 4.78, 4.90 to 4.93, 4.113, 5.13, 5.36, 5.40, 5.70, 5.71, 5.73, 5.75, 5.76, 5.78, 6.1, 6.8, 7.3, 7.33 and 8.72 are fully effective (0 to 5 % attack). Botrytis infestation of untreated, infected bean plants is 100%.

What we claim is:

1. A compound of the formula

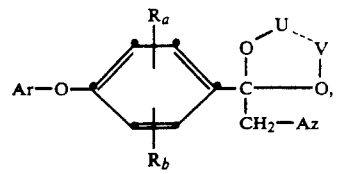

wherein

Az is 1H-1,2,4triazolyl or the group

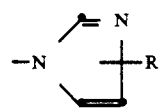

in which

R is hydrogen or $C_1-C_6$alkyl, $R_a$ and $R_b$, each independently of the other, are hydrogen, halogen, $C_1-C_3$alkyl, $C_1-C_3$alkoxy or nitro, Ar is phenyl or naphthyl, each unsubstituted or mono- or polysubstituted by halogen, $C_1-C_7$alkyl, $C_1-C_7$alkoxy, nitro and/or $CF_3$, U and V, each independently of the other, are $C_1-C_{12}$alkyl which is unsubstituted or substituted by halogen or $C_1-C_6$alkoxy, or together form one of the alkylene bridges

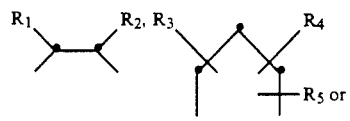

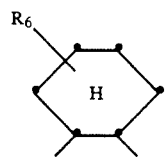

in which $R_1$ and $R_2$, each independently of the other, are hydrogen, $C_1-C_{12}$alkyl or $C_1-C_{12}$alkyl which is mono- or polysubstituted by halogen; phenyl or phenyl which is mono- or polysubstituted by halogen and/or $C_1-C_3$alkyl; or are the $-CH_2-Z-R_7$ group, wherein Z is oxygen or sulfur and $R_7$ is hydrogen, $C_1-C_8$alkyl, $C_1-C_8$alkyl which is substituted by $C_1-C_2$alkoxy, $C_3-C_4$alkenyl, propyn-2-yl, 3-halo-propyn-2-yl, phenyl or phenyl which is mono- or polysubstatuted by halogen $C_1-C_3$alkyl, $C_1-C_3$alkoxy, nitro and/or $CF_3$; benzyl or benzyl which is mono- or polysubstituted by halogen, $C_1-C_3$alkyl and/or $C_1-C_3$alkoxy, $R_3$, $R_4$ and $R_5$, each independently of the others are hydrogen or $C_1-C_4$alkyl, the total number of carbon atoms in $R_3$, $R_4$ and $R_5$ not exceeding 6, and $R_6$ is hydrogen or $C_1-C_3$alkyl, including the acid addition salts and metal complexes thereof.

2. A compound as claimed in claim 1 wherein Az is 1H-1,2,4triazolyl or unsubstituted imidazolyl.

3. A compound as claimed in claim 1, wherein Ar is the group

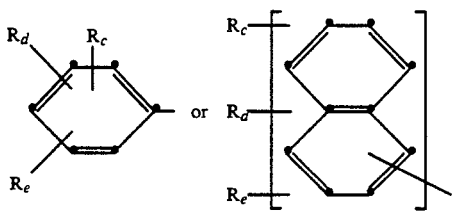

in which
  $R_c$, $R_d$ and $R_e$, each independently of the other, are hydrogen, halogen, $C_1$-$C_3$alkyl, $C_1$-$C_3$alkoxy, nitro or $CF_3$, or an acid additional salt or metal complex thereof.

4. A compound as claimed in claim 3, wherein $R_a$ and $R_b$ each independently of the other, are hydrogen, halogen or $C_1$-$C_3$alkyl, and Ar is the group

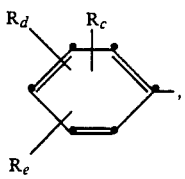

wherein $R_c$, $R_d$ and $R_e$, each independently of the other are hydrogen, $CF_3$ or $C_1$-$C_3$alkyl, or an acid addition salt or metal complex thereof.

5. A compound as claimed in claim 4, wherein U and V, each independently of the other, are $C_1$-$C_3$alkyl or together form one of the alkylene groups

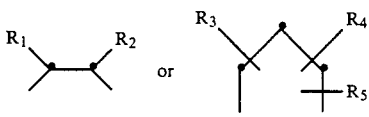

wherein $R_1$, $R_2$, $R_3$, $R_4$ and $R_5$ each independently of the others, are hydrogen or $C_1$-$C_4$alkyl, the total number of carbon atoms in $R_3$, $R_4$ and $R_5$ not exceeding 6, or an acid addition salt or metal complex thereof.

6. A compound as claimed in claim 3, wherein $R_a$, $R_b$, $R_c$, $R_d$ and $R_e$, each independently of the others, are chlorine, bromine, fluorine, methyl, methoxy or nitro; U and V, each independently of the other, are $C_1$-$C_3$alkyl or together form one of the alkylene bridge,

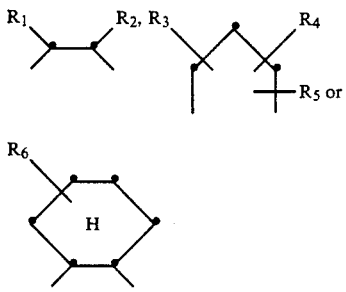

wherein $R_1$, $R_2$, $R_3$, $R_4$, $R_5$ and $R_6$, each independently of the others, are hydrogen or $C_1$-$C_3$alkyl, or $R_1$ is —$CH_2$—O—$R_7$ in which $R_7$ is $C_1$-$C_3$alkyl, $C_2$-$C_4$alkyl which is substituted by $C_1$-$C_3$alkoxy, $C_3$-$C_4$alkenyl or phenyl, or an acid addition salt or metal complex thereof.

7. A compound as claimed in claim 1, wherein $R_a$ and $R_b$, each independently of the other, are hydrogen, halogen or $C_1$-$C_3$alkyl, and Ar is the group

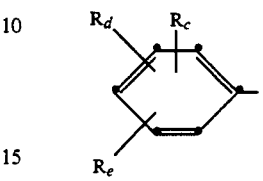

wherein $R_c$, $R_d$ and $R_e$, each independently of the others, are hydrogen, halogen, $CF_3$, $C_1$-$C_3$alkyl, $C_1$-$C_3$alkoxy, or an acid addition salt thereof.

8. A compound as claimed in claim 7, wherein U and V, each independently of the other, are $C_1$-$C_6$alkyl, $C_2$-$C_4$alkyl which is substituted by halogen or $C_1$-$C_2$alkoxy, or together form one of the alkylene bridge,

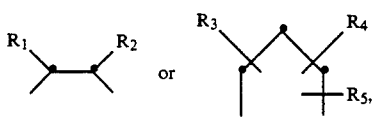

wherein $R_1$, $R_2$, $R_3$, $R_4$ and $R_5$, each independently of the others, are hydrogen or $C_1$-$C_4$alkyl, the total number of carbon atoms in $R_3$, $R_4$ and $R_5$ not exceeding 6, or an acid addition salt thereof.

9. A compound as claimed in claim 7, wherein U and V together are the alkylene group

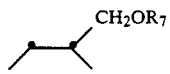

wherein $R_7$ is $C_1$-$C_4$alkyl, $C_2$-$C_4$alkyl which is substituted by $C_1$-$C_2$alkoxy, $C_3$-$C_4$alkenyl or propyn-2-yl, or an acid addition salt thereof.

10. A compound as claimed in claim 3 wherein Az is unsubstituted imidazolyl, $R_a$ and $R_b$, each independently of the other, are hydrogen, methyl, chlorine or bromine, $R_c$, $R_d$ and $R_e$, each independently of the others, are hydrogen, fluorine, chlorine, bromine, methyl, methoxy, $CF_3$ or nitro, U and V, each independently of the other, are $C_1$-$C_3$alkyl which is unsubstituted or substituted by $C_1$-$C_2$alkoxy or chlorine, or together form one of the alkylene bridge,

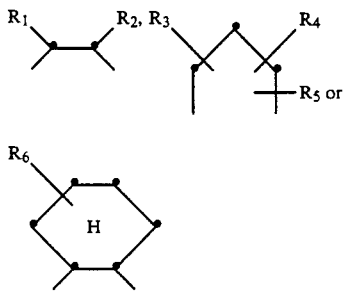

wherein $R_1$, $R_2$, $R_3$, $R_4$, $R_5$ and $R_6$, each independently of the others, are hydrogen or $C_1-C_3$alkyl, or $R_1$ is $-CH_2OR_7$, wherein $R_7$ is $C_1-C_3$alkyl, $C_2-C_3$alkyl which is substituted by $C_1-C_2$alkoxy, or $C_3-C_4$ alkenyl, or an acid addition salt thereof.

11. A compound as claimed in claim 1, wherein $R_a$ and $R_b$ each independently of the other, are hydrogen, halogen or $C_1-C_3$alkyl, and Ar is phenyl or phenyl which is substituted by $C_1-C_3$alkyl, $C_1-C_3$alkoxy, $CF_3$ or halogen, or an acid addition salt thereof.

12. A compound as claimed in claim 11, wherein each of $R_a$ and $R_b$ independently of the other is hydrogen, methyl, chlorine or bromine, Ar is phenyl or phenyl which is substituted by halogen, methyl or $CF_3$, and U and V, each independently of the other, are $C_1-C_3$alkyl, $C_2-C_3$alkyl which is unsubstituted or substituted by $C_1-C_2$alkoxy, or together form one of the alkylene bridges

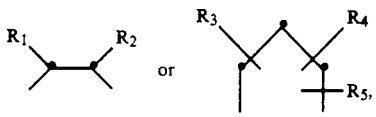

wherein $R_1$, $R_2$, $R_3$, $R_4$ and $R_5$, each independently of the others, are hydrogen or $C_1-C_4$alkyl, the total number of carbon atoms in $R_3$, $R_4$ and $R_5$ not exceeding 4, or an acid addition salt thereof.

13. A compound as claimed in claim 1, wherein $R_a$ and $R_b$ are hydrogen, Ar is phenyl or phenyl which is substituted by halogen or methyl, and U and V together are a group of the formula

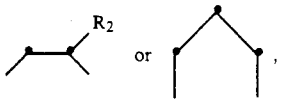

wherein $R_2$ is $C_1-C_4$alkyl, $C_1-C_3$hydroxyalkyl or $C_1-C_2$alkoxy-$C_1-C_2$ alkyl, or an acid addition salt thereof.

14. A compound as claimed in claim 13 wherein $R_2$ is methyl, ethyl, hydroxymethyl, 2-hydroxyethyl, methoxymethyl or ethoxymethyl.

15. A compound as claimed in claim 12 being 2-[p-(phenoxy)-phenyl]-2-[1-(1H-1,2,4-triazolyl)methyl ]-4-methyl-1,3-dioxane or a salt thereof.

16. A compound as claimed in claim 12 being 2-[p-(phenoxy)-phenyl]-2-[1-(1H-1,2,4 -triazolyi)-methyl]-4-ethyl-1,3-dioxane or a salt thereof.

17. A compound as claimed in claim 12 being 2-[p-(phenoxy)-2'-methylphenyl]-2-[1-(1H-1,2,4-triazolyl)-methyl]-4-ethyl1,3-dioxolane or salt thereof.

18. A compound as claimed in claim 14 being 2-[p-(3',4'-dichlorophenoxy)-phenyl]-2-[1-(1H-1,2,4-triazolyl)-methyl]-4-methoxymethyl-1,3-dioxolane or salt thereof.

19. A compound as claimed in claim 14 being 2-[p-(3',4'-dichlorophenoxy)-phenyl]-2-[1-(1H-1,2,4-triazol)-methyl]4-ethyl-1,3-dioxolane or salt thereof.

20. The compound as claimed in claim 6 being 2-[p-(4'-chlorophenoxy)-phenyl]-2-[1-(1H-1,2,4-triazolyl)-methyl]-4-ethyl-1,3-dioxolane copper sulphate complex.

21. A compound as claimed in claim 12 being 2-[p-(4'-chlorophenoxy)-2'-methylphenyl]-2-[1-(1H-1,2,4-triazolyl)-methyl]-4-methyl-1,3-dioxolane or salt thereof.

22. The compound as claimed in claim 17 being 2-[p-(phenoxy)-2'-methylphenyl]-2-[1-(1H-1,2,4-triazolyl)-methyl]-4-ethyl- 1,3-dioxolane nitric acid salt.

23. The compound as claimed in claim 14 being 2-[p-(4'-chlorophenoxy)-phenyl]-2-[1-(1H-1,2,4-triazolyl)-methyl]-4-ethyl-1,3-dioxolane or salt thereof.

24. The compound as claimed in claim 14 being 2-[p-(3'-chlorophenoxy)-phenyl]-2-(1-imidazolylmethyl)-4-ethyl-1,3-dioxolane or a salt thereof.

25. The compound as claimed in claim 14 being 2-[p-(4'-chlorophenoxy)-phenyl]-2-(1-imidazolylmethyl)-4-ethyl-1,3-dioxolane or a salt thereof.

26. The compound as claimed in claim 12 being 2-[p-(phenoxy)-2'-methylphenyl]-2-(1-imidazolylmethyl)-4-ethyl-1,3-dioxolane or a salt thereof.

27. The compound as claimed in claim 12 being 2-[p-(4'-chloro-phenoxy)-2'-methylphenyll-2-(1-imidazolyl-methyl)-4-methyl1,3-dioxolane or a salt thereof.

28. The compound as claimed in claim 12 being 2-[p-(4'-fluoro-phenoxy-2'-methylphenyl]-2-(1 -imidazolyl-methyl)-4-methyl1,3-dioxolane or a salt thereof.

29. The compound as claimed in claim 14 being 2-[p-(phenoxy)-phenyl]-2-[1-(1H-1,2,4 -triazolyl)methyl]-4-hydroxymethyl1,3-dioxolane or a salt thereof.

30. The compound as claimed in claim 14 being 2-[p-(4'-chlorophenoxy)-phenyl]-2-[1-(1H-1,2,4-triazolyl)-methyll-4-methoxymethyl-1,3-dioxolane or a salt thereof.

31. The compound as claimed in claim 14 being 2-[p-(4'-chlorophenoxy)-phenyl]-2-[l-(2 '-methylimidazolyl)-methyl]-4-ethyl1,3-dioxolane or a salt thereof.

32. The compound as claimed in claim 14 being 2-[p-(phenoxy)-phenyl]-2-[1-(1H-1,2,4-triazolyl)-methyl]-4-methyl-1,3dioxolane or a salt thereof.

33. The compound as claimed in claim 14 being 2-[p-(phenoxy)-phenyl]-2-[1-(1H-1,2,4-triazolyl)-methyl]-4-ethyl-1,3dioxolane or a salt thereof.

34. The compound as claimed in claim 12 being 2-[p-(phenoxy)-phenyl]-2-[1-(1H-1,2,4-triazolyl)-methyl]-4,5-dimethyl-1,3-dioxolane or a salt thereof.

35. The compound as claimed in claim 14 being 2-[p-(phenoxy)-phenyl]-2-[1-(1H-1,2,4-triazolyl)-methyl]-1,3-dioxane or a salt thereof.

36. The compound as claimed in claim 14 being 2-[p-(phenoxy)-phenyl]-2-(1-imidazolylmethyl)-4-ethyl-1,3-dioxolane or a salt thereof.

37. The compound as claimed in claim 14 being 2-[p-(2',4'-di-methylphenoxy)-phenyl]-2-(1-imidazolyl-methyl 4-ethyl-1,3dioxolane or a salt thereof.

38. The compound as claimed in claim 12 being 2-[p-(3'-trifluoromethylphenoxy)-phenyl]-2-( 1-imidazolyl-methyl)-4-ethyl-1,3-dioxolane or a salt thereof.

39. The compound as claimed in claim 14 being 2-[p-(4'-chloro3-methyl-phenoxy)-phenyl]-2-(1-imidazolyl-methyl)-4-ethyl-1,3-dioxolane or a salt thereof.

40. The compound as claimed in claim 14 being 2-[p-(3',4'-dichlorophenoxy)-phenyl]-2-(1 -imidazolylmethyl)4-ethyl-1,3dioxolane or a salt thereof.

41. The compound as claimed in claim 14 being 2-[p-(2',5'-dichlorophenoxy)-phenyl]-2-(1-imidazolylmethyl)-4-ethyl1,3-dioxolane or a salt thereof.

42. The compound as claimed in claim 14 being 2-[p-(3',4'-dichlorophenoxy)-phenyl]-2-(1-imidazolylmethyl) 4-methoxymethyl-1,3-dioxolane or a salt thereof.

43. The compound as claimed in claim 14 being 2-[p-(4'-fluorophenoxy)-phenyl]-2-( 1-imidazolylmethyl)-4-ethyl-1,3-dioxolane or a salt thereof.

44. The compound as claimed in claim 12 being 2-[p-(4'-fluorophenoxy)-phenyl]-2-( 1-imidazolylmethyl)-4,5-dimethyl-1,3-dioxolane or a salt thereof.

45. The compound as claimed in claim 14 being 2-[p-(4'-chloro-2-methyl-phenoxy)-phenyl]-2-( 1-imidazolylmethyl)-4-methoxymethyl-1,3-dioxolane or a salt thereof.

46. The compound as claimed in claim 14 being 2-[p-(4'-fluorophenoxy)-phenyl]-2-( 1-imidazolylmethyl)-4-hydroxymethyl-1,3-dioxolane or a salt thereof.

47. The compound as claimed in claim 14 being 2-[p-(4'-fluorophenoxy)-phenyl]-2-[1-( 1H-1,2,4-triazolyl)-methyl]-1,3dioxolane or a salt thereof.

48. The compound as claimed in claim 12 being 2-[p-(4'-chlorophenoxy)-2'-chlorophenyl]-2-[1-(1H-1,2,4-triazolyl)-methyl]-4-ethyl-1,3-dioxolane or a salt thereof.

49. The compound as claimed in claim 12 being 2-[p-(phenoxy)- 2'-methylphenyl]-2-(1-imidazolylmethyl)-4-ethyl-1,3dioxolane or a salt thereof.

50. The compound as claimed in claim 49 being 2-[p-(phenoxy)-2'-methylphenyl]-2-(1-imidazolylmethyl)-4-ethyl1,3-dioxolane hydrochloric acid salt.

51. The compound as claimed in claim 49 being 2-[p-(phenoxy)-2'-methylphenyl]-2-( 1-imidazolylmethyl)-4-ethyl-1,3-dioxolane sulfuric acid salt.

52. The compound as claimed in claim 49 being 2-[p-(phenoxy)-2'-methylphenyl]-2-( 1-imidazolylmethyl)-4-ethyl-1,3-dioxolane sulfonic acid salt.

53. The compound as claimed in claim 49 being 2-[p-(phenoxy)-2'-methylphenyl]-2-( 1-imidazolylmethyl)-4-ethyl-1,3-dioxolane nitric acid salt.

54. A pharmaceutical preparation containing at least one compound as,claiiqed in claim 1 in admixture with one or more conventional pharmaceutical carriers or excipients.

55. A pesticidal composition containing at least one compound as claimed in claim 1, and an agriculturally acceptable carrier.

56. A method of prophylactically or therapeutically combatting noxious microorganisms which comprises applying to the locus to be protected a microbicidally effective amount of a compound as claimed in claim 1.

57. A method for treatment of mycotic infestations, depressive, anxiety and/or epileptic diseases, which comprises administering a therapeutically effective amount of a compound claimed in claim 1 to a warm-blooded organism in need of such treatment.

* * * * *